United States Patent [19]
Landry

[11] Patent Number: 5,948,658
[45] Date of Patent: Sep. 7, 1999

[54] ANTI-COCAINE CATALYTIC ANTIBODY

[75] Inventor: Donald W. Landry, South New York, N.Y.

[73] Assignee: The Trustees of Columbia University in the City of New York, New York, N.Y.

[21] Appl. No.: 08/672,345

[22] Filed: Jun. 25, 1996

[51] Int. Cl.$^6$ .................................................. C12N 9/00
[52] U.S. Cl. ......................................................... 435/188.5
[58] Field of Search ........................................... 435/188.5

[56] References Cited

U.S. PATENT DOCUMENTS

| | | | |
|---|---|---|---|
| 3,888,866 | 6/1975 | Leute et al. | 200/292 |
| 3,917,582 | 11/1975 | Soffer et al. | 200/121 |
| 4,045,420 | 8/1977 | Soffer et al. | 200/112 |
| 4,197,237 | 4/1980 | Leute et al. | 200/112 B |
| 4,203,802 | 5/1980 | Rubenstein et al. | 435/188 |
| 4,235,864 | 11/1980 | Kaul et al. | 424/1 |
| 4,659,567 | 4/1987 | Tramontano et al. | 424/85 |
| 4,792,446 | 12/1988 | Kim et al. | 424/85.8 |
| 4,963,355 | 10/1990 | Kim et al. | 424/85.8 |
| 5,030,717 | 7/1991 | Tramontano et al. | 530/387 |
| 5,079,152 | 1/1992 | Benkovic et al. | 435/125 |
| 5,202,270 | 4/1993 | Ungemach et al. | 430/537 |
| 5,463,028 | 10/1995 | Landry et al. | 530/405 |

OTHER PUBLICATIONS

Yang, G., et. al. (1996) J. Am. Chem. Soc. 118, 5881–5890.
Landry, D.W., et. al. (1993) Science 259, 1899–1901.
Abraham, et al. (1992) "N–Modified Analogues of Cocaine: Synthesis and Inhibition of Binding to the Cocaine Receptor." *J. Med. Chem.* 35:141–144.
Ambre, J., et al. (1984), Urinary execretion of ecgonine methyl ester, a metabolite of cocaine in humans, *J. Anal Toxicol.*, 8:23–.
Ambre, J., et al. (1985), The urinary execretion of cocaine and metabolites in humans: a kinetic analysis of published data, *J. Anal., Toxicol.,* 9:241–245.
Chandrakumar, et al., (1993), Phenylphosphonate monoester analogs of cocaine, *Bioorg. & Medic. Chem. Let.,* 3:309–312.
Landry, et al. (1993), "Antibody–Catalyzed Degradation of Cocaine." *Science* 259:1899–1901.
*J. Med. Chem.* 35:135–140.
Schultz, P.G., (1988), The interplay between chemistry and biology in the design of enzymatic catalysts, *Science* 240:426–433.
Tramontano, et al., (1986), Catalytic antibodies, *Science,* 234:1566–1570.
Tramontano, A., et al., (1988), Antibody catalysis approaching the activity of enzymes, *J. Am. Chem. Soc.,* 110:2282–2286; and.
Tramontano, A., et al., (1986), Chemical reactivity at an antibody binding site elicited by mechanistic design of a synthetic anti–gen, *Proc. Natl. Acad. Sci. USA,* 83:6736–6740.

*Primary Examiner*—Charles L. Patterson, Jr.
*Attorney, Agent, or Firm*—John P. White; Cooper & Dunham LLP

[57] ABSTRACT

Disclosed are catalytic antibodies and polypeptides capable of degrading cocaine. Said catalytic antibodies and polypeptides are characterized by the amino acid sequence of their complementarity determining regions and framework regions. The present invention also discloses a pharmaceutical composition and a method for decreasing the concentration of cocaine in a subject. Finally, the invention discloses pharmaceutical compositions and methods for treating cocaine overdose and addiction in subjects.

14 Claims, 27 Drawing Sheets

Scheme 4

FIG. 6

LAMBDA LIGHT CHAIN ALIGNMENT

```
9A(lam9) vari   1:-------TWPGETVTLTCRSSTGTITTSNYANWVQEKPDHLFSGLIGINNNRPPGVP
19G(lam5) vari  1:-------.R..............A.........................V.......
15A10L Vari     1:AVVTQESALT.S................SD...................V.Y....
G7(lam4) vari   1:-------.RA..............S...AN..GS........T....VS...G...
                         *         ******           **       *****   ****

9A(lam9) vari   61:ARFSGSLIGDKAVLTITGAQTEDEAIYFCALWYSNHWVFGGGTKLTVLG
19G(lam5) vari  61:............T.A.................................
15A10 Vari      61:............T...................N..F............
G7(lam4) vari   61:.........................G......................
                    ************ *  *****************  **  *********
```

FIG. 7    KAPPA LIGHT CHAIN ALIGNMENT

```
3B9 K vari    1:DIVMTQDELSNPVTSGESVSISCRSSRSLLYRDGKTYLNWFLQRPGRPSPQLLIYLMSTRS
6A12 k vari   1:.M..........................................................A
12H(L2) k vari 1:.M.........................................................A
2A k vari     1:...I.........................K....E.................Q.H....A
E2(L7) k Vari 1:.EL...SP.TLS..I.QPA....K..Q....S......F...Q..KR...V.KLD
                 * **                    * *      ***             *    *****

3B9 K vari    61:SGVSDRFSGSGSGTDFTLEISRVKAEDVGVYYC-QHFVDYPFTFGSGTKLEIKR
6A12 k vari   61:.................................................
12H(L2) k vari 61:................................E..................
2A k vari     61:.................................A..-.Q..E.........R.
E2(L7) k Vari 61:...P..T....K....K....E...L..V.GY-TF.L...A......L...*
                    *   *    *    *      *   **            ***** *****
```

FIG. 8

HEAVY CHAIN ALIGNMENT

```
3B9 vari    1:DVQLQESGPGLVKPSQSLSLTCTVTGNSITSDYAWTWIRQFPGNKLEWMGYIR-HIYGTR
6A12 heavy  1:............................................................
12H H vari  1:............................................................
2AH-3 vari  1:----------------E...........................K......L.........
9(H-3) vari 1:----------E......GA.VK.S.KAS.YPF.-...NMY.VK.SH.KS...I...-YSGI..
19H6-3 vari 1:EIH..Q....E......GA.VK.S.KAS.Y.F.-...NMY.VK.SH.KS...I...DPSNG.IF
15A10 vari  1:E.........E......GA.VKVS.KAS.Y.F.-...NMY.VK.SH.KS...I...DP.NG.IF
E2(H8) vari 1:VQL.E-...AE..M.GA.VKMS.KAS.YTF.-...NMY.VK.NH.ES...IA..DPSNGD.F
G7(H8) Vari 1:VQL.E-...AE.....GA.VE.S.RTS.YTF.-T.YIY.VK.R..QG...IT.DLSDTY.G
                                                                  I.GMNPGNGV.Y
                 *          *   **  *       *    *    *  *   *  * ***

3B9 vari    61:YNPSLISRISITRDISKNQFFLQLDSVTAEDTATYYCVRYHYYGSAYWGQGILVTVSA
6A12 heavy  61:.........................................................
12H H vari  61:.........................................................
2AH-3 vari  61:........K.....N..T........I...YGN......TL.GLP
9(H-3) vari 61:...QKFKG.ATL.V.K.S.TA.MH.N.L.S..S.V...A.GGGL-F........E
19H6-3 vari 61:...QKFKG.ATL.V.K.S.TA.MH.N.L.S..S.V...A.GGGL-F...R....
15A10 vari  61:...QKFQGKATV.L.K.SSTA.MH.N.L.S..S.V...A.GGGL-F.F......
E2(H8) vari 61:...QNFKG.ATL.L.E.S.TAYM..S.L.S..S.V...S.RG---FD......TL...S
G7(H8) Vari 61:F.FKFKN.ATI.V.R.SSIAYM..S.L.S..S.V..T.VGNL-F...R........
                                                         *   ** ***        *
```

FIG. 9

```
           10        20        30        40        50        60
GCTGTTGTTACTCAGGAGTCTGCTCTAACTACATCACCTGGTGAAACAGTCACACTCACT
 A  V  V  T  Q  E  S  A  L  T  T  S  P  G  E  T  V  T  L  T 70        80        90       100       110       120
TGTCGCTCAAGTACTGGGACTATTACAAGTGATAACTATGCCAACTGGGTCCAAGAAAAA
 C  R  S  S  T  G  T  I  T  S  D  N  Y  A  N  W  V  Q  E  K 130       140       150       160       170       180
CCAGATCATTTATTCAGTGGTCTAATAGGTGTTAATAATTACCGACCTCCAGGTGTTCCT
 P  D  H  L  F  S  G  L  I  G  V  N  N  Y  R  P  P  G  V  P 190       200       210       220       230       240
GCCAGATTCTCAGGCTCCCTGACTGGAGACAAGGCTGTCCTCACCATCACAGGGGCACAG
 A  R  F  S  G  S  L  T  G  D  K  A  V  L  T  I  T  G  A  Q 250       260       270       280       290       300
ACTGAGGATGAGGCAATATATTTCTGTGCTCTATGGTACAGCAACCACTGGGTGTTCGGT
 T  E  D  E  A  I  Y  F  C  A  L  W  Y  S  N  H  W  V  F  G 310       320       330       340       350       360
GGAGGAACCAAACTGACTGTCCTAGGCCAGCCCAAGTCTTCGCCATCAGTCACCCTGTTT
 G  G  T  K  L  T  V  L  G
```

FIG. 10

```
           10         20         30         40         50         60
TCTGGACCTGAGCTGGTGAAGCCTGGGGCTTCAGTGAAGGTATCCTGTAAGGCTTCTGGT
 S  G  P  E  L  V  K  P  G  A  S  V  K  V  S  C  K  A  S  G 70         80         90        100        110        120
TATTCATTCACTGACTACAATATGTACTGGGTGAAGCAGAACCATGGAGAGAGCCTTGAA
 Y  S  F  T  D  Y  N  M  Y  W  V  K  Q  N  H  G  E  S  L  E 130        140        150        160        170        180
TGGATTGCATATATTGATCCTTCCAATGGTGATACTTTCTACAACCAGAAATTCCAGGGC
 W  I  A  Y  I  D  P  S  N  G  D  T  F  Y  N  Q  K  F  Q  G 190        200        210        220        230        240
AAGGCCACAGTGACTCTTGACAAGTCCTCCAGTACAGCCTTCATGCATCTCAACAGCCTG
 K  A  T  V  T  L  D  K  S  S  S  T  A  F  M  H  L  N  S  L 250        260        270        280        290        300
ACATCTGAGGACTCTGCAGTCTATTACTGTGCAAGAGGGGGGGGCCTGTTTGCTTTCTGG
 T  S  E  D  S  A  V  Y  Y  C  A  R  G  G  G  L  F  A  F  W 310        320        330
GGGCAAGGGACTCTGGTCACTGTCTCTGCA
 G  Q  G  T  L  V  T  V  S  A
```

FIG. 11

```
         10        20        30        40        50        60
GTCGCATGCTCCCGGNCGNCATGGNCGCGGGATTGGGAATTCCACGAGGCCGGGGGAGAC
                                                T  R  P  G  E  T 70        80        90       100       110       120
AGTCACACTCACTTGTCGTTCAAGTGCTGGGACTATTACAACTAGTAACTATGCCAACTG
 V  T  L  T  C  R  S  S  A  G  T  I  T  T  S  N  Y  A  N  W 130       140       150       160       170       180
GGTCCAAGAAAAACCAGATCATTTATTCAGTGGTCTAATAGGTGTTAACAACAACCGACC
 V  Q  E  K  P  D  H  L  F  S  G  L  I  G  V  N  N  N  R  P 190       200       210       220       230       240
TCCAGGTGTTCCTGCCAGATTCTCAGGCTCCCTGATTGGAGACACGGCTGCCCTCACCAT
  P  G  V  P  A  R  F  S  G  S  L  I  G  D  T  A  A  L  T  I 250       260       270       280       290       300
CACAGGGGCACAGACTGAGGATGAGGCAATATATTTCTGTGCTCTATGGTACAGCAACCA
  T  G  A  Q  T  E  D  E  A  I  Y  F  C  A  L  W  Y  S  N  H 310       320       330       340       350       360
CTGGGTGTTCGGTGGAGGAACCAAACTGACTGTCCTAGGCCAGCCCAAGTCTTCGNCATC
  W  V  F  G  G  G  T  K  L  T  V  L  G
```

FIG. 12

```
         10         20         30         40         50         60
GAATTCGGCACGAGCAGGAACTACAGGTGTCCACTCTGAGATCCACCTGCAGCAGTCTGG
                                        E  I  H  L  Q  Q  S  G 70         80         90        100        110        120
ACCTGAGCTGGTGAAGCCTGGGGCTTCAGTGAAGTTATCCTGCAAGGCTTCTGGTTACTC
 P  E  L  V  K  P  G  A  S  V  K  L  S  C  K  A  S  G  Y  S 130        140        150        160        170        180
ATTCACTGACTACAACATGTACTGGGTGAAACAGAGCCATGGAAAGAGCCTTGAGTGGAT
 F  T  D  Y  N  M  Y  W  V  K  Q  S  H  G  K  S  L  E  W  I 190        200        210        220        230        240
TGGATATATTGATCCTCACAATGGTGGTATTTTCTACAACCAGAAGTTCAAGGGCAGGGC
 G  Y  I  D  P  H  N  G  G  I  F  Y  N  Q  K  F  K  G  R  A 250        260        270        280        290        300
CACATTGACTGTTGACAAGTCCTCCAACACAGCCTTCATGCATCTCAACAGCCTGACATC
 T  L  T  V  D  K  S  S  N  T  A  F  M  H  L  N  S  L  T  S 310        320        330        340        350        360
TGAGGACTCTGCAGTCTATTACTGTGCAAGAGGGGGGGGCCTGTTTGCTTACTGGGGCCG
 E  D  S  A  V  Y  Y  C  A  R  G  G  G  L  F  A  Y  W  G  R 370        380        390        400        410        420
AGGGACTCTGGTCACTGTCTCTGCAGCCAAAACGACACCCCCATCTGTCTATCCACTGGC
 G  T  L  V  T  V  S  A
```

FIG. 13

```
         10        20        30        40        50        60
GTCGCATGCTCCCGGNCGCCATGGNCGCGGGATTGGGAATTCCACGTGGCCGGGGGAGAC
                                              T  W  P  G  E  T 70        80        90       100       110       120
AGTCACACTCACTTGTCGCTCAAGTACTGGGACTATTACAACTAGTAACTATGCCAACTG
 V  T  L  T  C  R  S  S  T  G  T  I  T  T  S  N  Y  A  N  W 130       140       150       160       170       180
GGTCCAAGAAAAACCAGATCATTTATTCAGTGGTCTGATAGGTATTAACAACAACCGACC
 V  Q  E  K  P  D  H  L  F  S  G  L  I  G  I  N  N  N  R  P 190       200       210       220       230       240
TCCAGGTGTTCCTGCCAGATTCTCAGGCTCCCTGATTGGAGACAAGGCTGTCCTCACCAT
 P  G  V  P  A  R  F  S  G  S  L  I  G  D  K  A  V  L  T  I 250       260       270       280       290       300
CACAGGGGCACAGACTGAGGATGAGGCAATATATTTCTGTGCTCTATGGTACAGCAACCA
 T  G  A  Q  T  E  D  E  A  I  Y  F  C  A  L  W  Y  S  N  H 310       320       330       340       350       360
CTGGGTGTTCGGTGGAGGAACCAAACTGACTGTCCTAGGCCAGCCCAAGTCTTCGNCATC
 W  V  F  G  G  G  T  K  L  T  V  L  G
```

FIG. 14

```
           70        80        90       100       110       120
GGTCCAGCTGCTCGAGTCTGGACCTGAGCTGGTGAAGCCTGGGGCTTCAGTGAAGTTATC
     S   G   P   E   L   V   K   P   G   A   S   V   K   L   S 130       140       150       160       170       180
CTGCAAGGCTTCTGGTTACCCATTCACTGACTACAACATGTACTGGGTGAAGCAGAGCCA
 C   K   A   S   G   Y   P   F   T   D   Y   N   M   Y   W   V   K   Q   S   H 190       200       210       220       230       240
TGGAAAGAGCCTTGAGTGGATTGGATATATTGATCCTTCCAATGGTGGTATTTTTTACAA
 G   K   S   L   E   W   I   G   Y   I   D   P   S   N   G   G   I   F   Y   N 250       260       270       280       290       300
CCAGAAGTTCAAGGGCAGGGCCACATTGACTGTTGACAAGTCCTCCAACACAGCCTTCAT
 Q   K   F   K   G   R   A   T   L   T   V   D   K   S   S   N   T   A   F   M 310       320       330       340       350       360
GCATCTCAACAGCCTGACATCTGAGGACTCTGCAGTCTATTACTGTGCAAGAGGGGGGGG
 H   L   N   S   L   T   S   E   D   S   A   V   Y   Y   C   A   R   G   G   G 370       380       390       400       410       420
CCTGTTTGCTTACTGGGGCCAAGGGACTCTGGTCACTGTCTCTGAAGCCAAAACGAAACC
 L   F   A   Y   W   G   Q   G   T   L   V   T   V   S   E
```

FIG. 15

```
         70        80        90       100       110       120
AGGCGGCCGCACTAGTGATTGGGAATTCCACGAGGGCGGGGGAGACAGTCACACTCACTT
                             T  R  A  G  E  T  V  T  L  T  C 130       140       150       160       170       180
GTCGCTCAAGTAGTGGGACTATTACAGCTAATAACTATGGCAGCTGGGTCCAGGAAAAGC
 R  S  S  S  G  T  I  T  A  N  N  Y  G  S  W  V  Q  E  K  P 190       200       210       220       230       240
CAGATCATTTATTCACTGGTCTAATAGGTGTTAGCAACAACCGAGGTCCAGGTGTTCCTG
 D  H  L  F  T  G  L  I  G  V  S  N  N  R  G  P  G  V  P  A 250       260       270       280       290       300
CCAGATTCTCAGGCTCCCTAATTGGAGACAAGGCTGTCCTCACCATCACGGGGGGGCAGA
 R  F  S  G  S  L  I  G  D  K  A  V  L  T  I  T  G  G  Q  T 310       320       330       340       350       360
CTGAGGATGAGGCAATTTATTTCTGTGCTCTATGGAACAGCAACCATTTCGTGTTCGGTG
 E  D  E  A  I  Y  F  C  A  L  W  N  S  N  H  F  V  F  G  G 370       380       390       400       410       420
GAGGAACCAAACTGACTGTCCTAGGGCAGACCAAGTCTTTCGGCATCAAGCACCCTGTTT
 G  T  K  L  T  V  L  G  Q
```

FIG. 16

```
          10        20        30        40        50        60
CCATTGGGCCCGACGTCGCATGCTCCCGGCCGCCATGGCCGCGGGATTAGGTCCAACTTC
                                            V  Q  L  L 70        80        90        100       110       120
TCGAGTCTGGGGCTGAACTGGTGAAGCCTGGGGCTTCAGTGGAGTTGTCCTGCAGGACTT
 E  S  G  A  E  L  V  K  P  G  A  S  V  E  L  S  C  R  T  S 130       140       150       160       170       180
CTGGCTACACCTTCACCACCTACTATATTTACTGGGTAAAACAGAGGCCTGGACAAGGCC
 G  Y  T  F  T  T  Y  Y  I  Y  W  V  K  Q  R  P  G  Q  G  L 190       200       210       220       230       240
TTGAGTGGATTGGGGGGATGAATCCTGGCAATGGTGTTACTTACTTCAATGAAAAATTCA
 E  W  I  G  G  M  N  P  G  N  G  V  T  Y  F  N  E  K  F  K 250       260       270       280       290       300
AGAACAGGGCCACACTGACTGTGGACAGATCCTCCAGCATTGCCTACATGCAACTCAGCA
 N  R  A  T  L  T  V  D  R  S  S  S  I  A  Y  M  Q  L  S  S 310       320       330       340       350       360
GCCTGACATCTGAGGACTCTGCGGTCTATTACTGTACACGGGTGGGTAACCTCTTTGCTT
 L  T  S  E  D  S  A  V  Y  Y  C  T  R  V  G  N  L  F  A  Y 370       380       390       400       410       420
ACTGGGGCCGAGGGACTCTGGTCACTGTCTCTGCAGCCAAAACGACACCCCACTTTCTAT
 W  G  R  G  T  L  V  T  V  S  A
```

FIG. 17

```
          10        20        30        40        50        60
GATATTGTGATGACCCAGGATGAACTCTCCAATCCTGTCACTTCTGGAGAATCAGTTTCC
 D  I  V  M  T  Q  D  E  L  S  N  P  V  T  S  G  E  S  V  S 70        80        90       100       110       120
ATCTCCTGCAGGTCTAGTAGGAGTCTCCTATATAGGGATGGGAAGACATACTTGAATTGG
 I  S  C  R  S  S  R  S  L  L  Y  R  D  G  K  T  Y  L  N  W 130       140       150       160       170       180
TTTCTGCAGAGACCAGGACGATCTCCTCAACTCCTGATCTATTTGATGTCCACCCGTTCA
 F  L  Q  R  P  G  R  S  P  Q  L  L  I  Y  L  M  S  T  R  S 190       200       210       220       230       240
TCAGGAGTCTCAGACCGGTTTAGTGGCAGTGGGTCAGGAACAGATTTCACCCTGGAAATC
 S  G  V  S  D  R  F  S  G  S  G  S  G  T  D  F  T  L  E  I 250       260       270       280       290       300
AGTAGAGTGAAGGCTGAGGATGTGGGTGTGTATTACTGTCAACACTTTGTAGACTATCCA
 S  R  V  K  A  E  D  V  G  V  Y  Y  C  Q  H  F  V  D  Y  P 310       320       330
TTCACGTTCGGCTCGGGGACAAAGTTGGAGATAAAACGG
 F  T  F  G  S  G  T  K  L  E  I  K  R
```

FIG. 18

```
         10        20        30        40        50        60
GATGTGCAGCTTCAGGAGTCGGGACCTGGCCTGGTGAAACCTTCTCAGTCTCTGTCCCTC
 D  V  Q  L  Q  E  S  G  P  G  L  V  K  P  S  Q  S  L  S  L 70        80        90       100       110       120
ACCTGCACTGTCACTGGCAATTCAATCACCAGTGATTATGCCTGGACCTGGATCCGGCAG
 T  C  T  V  T  G  N  S  I  T  S  D  Y  A  W  T  W  I  R  Q 130       140       150       160       170       180
TTTCCAGGAAACAAACTGGAGTGGATGGGCTACATAAGGCACATTTATGGCACTAGGTAC
 F  P  G  N  K  L  E  W  M  G  Y  I  R  H  I  Y  G  T  R  Y 190       200       210       220       230       240
AACCCTTCTCTCATAAGTCGAATCTCTATCACTCGAGACACGTCCAAGAACCAGTTCTTC
 N  P  S  L  I  S  R  I  S  I  T  R  D  T  S  K  N  Q  F  F 250       260       270       280       290       300
CTGCAGTTGGATTCTGTGACTGCTGAGGACACAGCCACATATTATTGTGTAAGATATCAT
 L  Q  L  D  S  V  T  A  E  D  T  A  T  Y  Y  C  V  R  Y  H 310       320       330       340       350       360
TACTACGGTTCGGCTTACTGGGGCCAAGGGACTCTGGTCACTGTCTCTGCAGCCAAAACG
 Y  Y  G  S  A  Y  W  G  Q  G  T  L  V  T  V  S  A  A  K  T

ACACCC
 T  P
```

FIG. 19

```
         10        20        30        40        50        60
GATATGGTGATGACGCAAGATGAACTCTCCAATCCTGTCACTTCTGGAGAATCAGTTTCC
 D  M  V  M  T  Q  D  E  L  S  N  P  V  T  S  G  E  S  V  S 70        80        90       100       110       120
ATCTCCTGCAGGTCTAGTAGGAGTCTCCTATATAGGGATGGGAAGACATACTTGAATTGG
 I  S  C  R  S  S  R  S  L  L  Y  R  D  G  K  T  Y  L  N  W 130       140       150       160       170       180
TTTCTGCAGAGACCAGGACGATCTCCTCAACTCCTGATCTATTTGATGTCCACCCGTGCA
 F  L  Q  R  P  G  R  S  P  Q  L  L  I  Y  L  M  S  T  R  A 190       200       210       220       230       240
TCAGGAGTCTCAGACCGGTTTAGTGGCAGTGGGTCAGGAACAGATTTCACCCTGGAAATC
 S  G  V  S  D  R  F  S  G  S  G  S  G  T  D  F  T  L  E  I 250       260       270       280       290       300
AGTAGAGTGAAGGCTGAGGATGTGGGTGTGTATTACTTTCAACACTTTGAAGACTATCCA
 S  R  V  K  A  E  D  V  G  V  Y  Y  F  Q  H  F  E  D  Y  P 310       320       330       340       350       360
TTCACGTTCGGCTCGGGGACAAAATTGGAGATAAAACGGGCTGATGCTGCACCAACTGTA
 F  T  F  G  S  G  T  K  L  E  I  K  R

TCCATCTT
```

FIG. 20

```
         10        20        30        40        50        60
GACGTGCAGTTGCAGGAGTCGGGACCTGGCCTGGTGAAACCTTCTCAGTCTCTGTCCCTC
 D  V  Q  L  Q  E  S  G  P  G  L  V  K  P  S  Q  S  L  S  L 70        80        90       100       110       120
ACCTGCACTGTCACTGGCAATTCAATCACCAGTGATTATGCCTGGACCTGGATCCGGCAG
 T  C  T  V  T  G  N  S  I  T  S  D  Y  A  W  T  W  I  R  Q 130       140       150       160       170       180
TTTCCAGGAAACAAACTGGAGTGGATGGGCTACATAAGGCACATTTATGGCACTAGGTAC
 F  P  G  N  K  L  E  W  M  G  Y  I  R  H  I  Y  G  T  R  Y 190       200       210       220       230       240
AACCCTTCTCTCATAAGTCGAATCTCTATCACTCGAGACACGTCCAAGAACCAGTTCTTC
 N  P  S  L  I  S  R  I  S  I  T  R  D  T  S  K  N  Q  F  F 250       260       270       280       290       300
CTGCAGTTGGATTCTGTGACTGCTGAGGACACAGCCACATATTATTGTGTAAGATATCAT
 L  Q  L  D  S  V  T  A  E  D  T  A  T  Y  Y  C  V  R  Y  H 310       320       330       340       350       360
TACTACGGTTCGGCTTACTGGGGCCAAGGGACTCTGGTCACTGTCTCTGCAGCCAAAACG
 Y  Y  G  S  A  Y  W  G  Q  G  T  L  V  T  V  S  A  A  K  T

ACACCC
 T  P
```

FIG. 21

```
         10        20        30        40        50        60
GATATGGTGATGACGCAAGACGAACTCTCCAATCCTGTCACTTCTGGAGAATCAGTTTCC
 D  M  V  M  T  Q  D  E  L  S  N  P  V  T  S  G  E  S  V  S 70        80        90       100       110       120
ATCTCCTGCAGGTCTAGTAAGAGTCTCCTATATGAGGATGGGAAGACATACTTGAATTGG
 I  S  C  R  S  S  K  S  L  L  Y  E  D  G  K  T  Y  L  N  W 130       140       150       160       170       180
TTTCTGCAGAGACCAGGACAATCTCCTCACCTCCTGATCTATTTGATGTCCACCCGTGCA
 F  L  Q  R  P  G  Q  S  P  H  L  L  I  Y  L  M  S  T  R  A 190       200       210       220       230       240
TCAGGAGTCTCAGACCGGTTTAGTGGCAGTGGGTCAGGAACAGATTTCACCCTGGAAATC
 S  G  V  S  D  R  F  S  G  S  G  S  G  T  D  F  T  L  E  I 250       260       270       280       290       300
AGTAGAGTGAAGGCTGAGGATGTGGGTGCGTATTACTGTCAACAATTTGTAGAGTATCCA
 S  R  V  K  A  E  D  V  G  A  Y  Y  C  Q  Q  F  V  E  Y  P 310       320       330       340       350       360
TTCACGTTCGGCTCGGGGACAAAGTTGGAAATAAGACGGGTTGATGCCGCACCAACTGTA
 F  T  F  G  S  G  T  K  L  E  I  R  R

TCCATCTT
```

FIG. 22

```
         10         20         30         40         50         60
CATTGGGCCCACGTCGAATGNTCCCGGNCGNCATGGNCGNGGGATTGANAGGGGGNCGGA
                                                           E 70         80         90        100        110        120
GCTGGTGAAGCCTTCTCAGTCTCTGTCCCTCACCTGCACTGTCACTGGCTACTCAATCAC
 L  V  K  P  S  Q  S  L  S  L  T  C  T  V  T  G  Y  S  I  T 130        140        150        160        170        180
CAGTGATTATGCCTGGAACTGGATCCGGCAGTTTCCAGGAAACAGACTGGAGTGGATGGG
  S  D  Y  A  W  N  W  I  R  Q  F  P  G  N  R  L  E  W  M  G 190        200        210        220        230        240
CTACATAAGGTACAGTGGTATCACTAGGTACAACCCATCTCTCAAAAGTCGAATCTCTAT
  Y  I  R  Y  S  G  I  T  R  Y  N  P  S  L  K  S  R  I  S  I 250        260        270        280        290        300
CACTCGAGACACATCCAAGAACAAGTTCTTCCTGCAGTTAAATTCTGTGACTACTGAGGA
  T  R  D  T  S  K  N  K  F  F  L  Q  L  N  S  V  T  T  E  D 310        320        330        340        350        360
CACAGCCACTTATTACTGTGTAAGAATTCATTACTACGGCTACGGCAACTGGGGGCAAGG
  T  A  T  Y  Y  C  V  R  I  H  Y  Y  G  Y  G  N  W  G  Q  G 370        380        390        400        410        420
CACCACTCTCACAGGTCTTCCTCAAGAGTCTGGGAAGAAATCCCACCCATCTTCCCCACT
  T  T  L  T  G  L  P
```

FIG. 23

```
         10        20        30        40        50        60
NCCTTGGGCCGANGGCGCATGCTCCCGGCCGCCATGGCCGCGGGATTAGAGCGATATGGT
                                                         D  M  V 70        80        90       100       110       120
GATGACGCAGGATGAACTCTCCAATCCTGTCACTTCTGGAGAATCAGTTTCCATCTCCTG
 M  T  Q  D  E  L  S  N  P  V  T  S  G  E  S  V  S  I  S  C 130       140       150       160       170       180
CAGGTCTAGTAGGAGTCTCCTATATAGGGATGGGAAGACATACTTGAATTGGTTTCTGCA
 R  S  S  R  S  L  L  Y  R  D  G  K  T  Y  L  N  W  F  L  Q 190       200       210       220       230       240
GAGACCAGGACGATCTCCTCAACTCCTGATCTATTTGATGTCCACCCGTGCATCAGGAGT
 R  P  G  R  S  P  Q  L  L  I  Y  L  M  S  T  R  A  S  G  V 250       260       270       280       290       300
CTCAGACCGGTTTAGTGGCAGTGGGTCAGGAACAGATTTCACCCTGGAAATCAGTAGAGT
 S  D  R  F  S  G  S  G  S  G  T  D  F  T  L  E  I  S  R  V 310       320       330       340       350       360
GAAGGCTGAGGATGTGGGTGTGTATTACTGTCAACACTTTGTAGACTATCCATTCACGTT
 K  A  E  D  V  G  V  Y  Y  C  Q  H  F  V  D  Y  P  F  T  F 370       380       390       400       410       420
CGGCTCGGGGACAAAGTTGGAGATAAAACGGGTTGATGCTGNANCAACTGTATCCATCTT
 G  S  G  T  K  L  E  I  K  R
```

FIG. 24

```
          70        80        90        100       110       120
CTAGTGATTGCTCTAGAGCGACGTGCAGTTGCAGGAGTCGGGACCTGGACTGGTGAAACC
                    D  V  Q  L  Q  E  S  G  P  G  L  V  K  P 130       140       150       160       170       180
TTCTCAGTCTCTGTCCCTCACCTGCACTGTCACTGGTAATTCAATCACCAGTGATTATGC
 S  Q  S  L  S  L  T  C  T  V  T  G  N  S  I  T  S  D  Y  A 190       200       210       220       230       240
CTGGACCTGGATCCGGAAGTTTCCAGGAAACAAACTGGAGTGGTTGGGCTACATAAGGCA
 W  T  W  I  R  K  F  P  G  N  K  L  E  W  L  G  Y  I  R  H 250       260       270       280       290       300
CATTTATGGCACTAGGTACAACCCTTCTCTCATAAGTCGAATCTCTATCACTCGAGACAC
 I  Y  G  T  R  Y  N  P  S  L  I  S  R  I  S  I  T  R  D  T 310       320       330       340       350       360
GTCCAAGAACCAGTTCTTCCTGCAGTTGGATTCTGTGACTGCTGAGGACACAGCCACATA
 S  K  N  Q  F  F  L  Q  L  D  S  V  T  A  E  D  T  A  T  Y 370       380       390       400       410       420
TTATTGTGTAAGATATCATTACTACGGGTCGGCTTACTGGGGGCAAGGGACTCTGGTCAC
 Y  C  V  R  Y  H  Y  Y  G  S  A  Y  W  G  Q  G  T  L  V  T 430       440       450       460       470       480
TGTCTCTGCAGGCAAAACGANACCCCATCTGTCTATCCACTGGCCCCGGAACGCCGCCAG
 V  S  A
```

FIG. 25

```
          10        20        30        40        50        60
TTNAAGGCCCNGACGCCGCATAGCTCNCGGCCGCCATGGCCGNGGGATTCCAGTTCCGAG
                                                            E 70        80        90       100       110       120
CTCGTGATGACACAGTCTCCACTCACTTTGTCGGTAACCATTGGACAACCAGCCTCTATC
 L  V  M  T  Q  S  P  L  T  L  S  V  T  I  G  Q  P  A  S  I 130       140       150       160       170       180
TCTTGCAAGTCAAGTCAGAGCCTCTTATATAGTGATGGAAAAACCTATTTGAATTGGTTC
 S  C  K  S  S  Q  S  L  L  Y  S  D  G  K  T  Y  L  N  W  F 190       200       210       220       230       240
TTCCAGAGGCCAGGCCAGTCTCCAAAGCGCCTAATCTATCTGGTGTCTAAACTGGACTCT
 F  Q  R  P  G  Q  S  P  K  R  L  I  Y  L  V  S  K  L  D  S 250       260       270       280       290       300
GGAGTCCCTGACAGGTTCACTGGCAGTGGATCAGGAAAAGATTTTACACTGAAAATCAGC
 G  V  P  D  R  F  T  G  S  G  S  G  K  D  F  T  L  K  I  S 310       320       330       340       350       360
AGAGTGGAGGCTGAGGATTTGGGACTTTATTACTGCGTTCAAGGGTACACATTTCCGCTC
 R  V  E  A  E  D  L  G  L  Y  Y  C  V  Q  G  Y  T  F  P  L 370       380       390       400       410       420
ACGTTCGGTGCTGGGACCAAGCTGGAGCTGAAACGGGTGATGCTGACCAACTTGTTTCAT
 T  F  G  A  G  T  K  L  E  L  K  R
```

FIG. 26

```
         10        20        30        40        50        60
TTGGGCCCGGACGTCGCATGCTCCCGGCCGCCATGGNCGNGGGATTAGGTCCAACTTCTC
                                                 V  Q  L  L 70        80        90       100       110       120
GAGTCTGGGGCTGAGCTTGTGATGCCTGGGGCTTCAGTGAAGATGTCCTGCAAGGCTTCT
 E  S  G  A  E  L  V  M  P  G  A  S  V  K  M  S  C  K  A  S 130       140       150       160       170       180
GGCTACACATTCACTGACCACTGGATGCACTGGGTGAAGCAGAGGCCTGGACAAGGCCTT
 G  Y  T  F  T  D  H  W  M  H  W  V  K  Q  R  P  G  Q  G  L 190       200       210       220       230       240
GAGTGGATCGGAACGATTGATCTTTCTGATACTTATACTGGCTACAATCAAAACTTCAAG
 E  W  I  G  T  I  D  L  S  D  T  Y  T  G  Y  N  Q  N  F  K 250       260       270       280       290       300
GGCAGGGCCACATTGACTCTCGACGAATCCTCCAACACAGCCTACATGCAGCTCAGCAGC
 G  R  A  T  L  T  L  D  E  S  S  N  T  A  Y  M  Q  L  S  S 310       320       330       340       350       360
CTGACATCTGAGGACTCTGCGGTCTATTACTGTTCAAGAAGGGGCTTTGACTACTGGGGG
 L  T  S  E  D  S  A  V  Y  Y  C  S  R  R  G  F  D  Y  W  G 370       380       390       400       410       420
CAAGGCACCACTCTCACAGTCTCCTCAGGCAAAACGACAACCCCATCTTGTCTNTCCACT
 Q  G  T  T  L  T  V  S  S
```

FIG. 27

```
NdeI                                        H1
|MEVQLQESGPELVKPSQSLSLTCTVTGNSIT|SDYAWT|WIRQFP
              H2
GNKLEWMG|YIRHIYGTRYNPSLIS|RISITRDTSKNQFFLQLDS
                                       SphI
           H3                           |——linker
VTAEDTATYYCVR|YHYYGSAY|WGQGTLVTVSAGMQSGGGGSG
     NcoI
  ————||                                  L1
GGGSGGAMDIVMTQDELSNPVTSGESVSISC|RSSRSLLYRDGK
                    L2
TYLN|WFLQRPGRPPQLLIY|LMSTRSS|GVSDRFSGSGSGTDFTL
             L3
EISRVKAEDVGVYYC|QHFVDYPFT|FGSGTKLEIKRADGAPTVS
      Flag       6 x His
IFPPSL|DYKDDDDKLE|HHHHHH|
```

ANTI-COCAINE CATALYTIC ANTIBODY

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Catalytic antibodies have unique potential for the treatment of cocaine addiction and overdose. Cocaine reinforces self-administration by inhibiting a dopamine re-uptake transporter (1) in the mesolimbocortical "reward pathway". No antagonist to cocaine is known (2), perhaps reflecting the difficulties inherent in blocking a blocker. As an alternative to receptor-based therapeutics, a circulating agent could interrupt the delivery of cocaine to its binding site in the brain (3). An agent such as an antibody that merely bound the drug could be depleted stoichiometrically by complex formation but an enzyme that bound drug, transformed it and released product would be available for additional binding. Catalytic antibodies, a novel class of artificial enzyme, are inducible for a wide array of reactions and their substrate specificity is programmable to small molecules such as cocaine (4).

Cocaine detoxification is particularly well suited for a catalytic antibody approach. First, hydrolysis of the benzoyl ester of cocaine yields the biologically inactive products (5) ecgonine methyl ester and benzoic acid (FIG. 1). The plasma enzyme butyrylcholinesterase deactivates cocaine in humans (6) by means of this reaction. Second, acyl hydrolysis is the best studied of all antibody-catalyzed transformations (7,8). Esterase activity approaching that of natural enzymes has been reported (7) for catalytic antibodies and the large hydrophobic surface of the benzoyl ester is particularly well suited to elicit antibodies with strong binding and catalysis.

It has previously described (9) the first catalytic antibodies to degrade cocaine, Mab 3B9 and Mab 6A12. The antibodies were elicited by an immunogenic conjugate (TSA 1) of a phosphonate monoester transition-state analog. The rate acceleration of these first artificial cocaine esterases ($10^2$–$10^3$) corresponded in magnitude to their relative stabilization of the ground-state to the transition-state (~$K_m$/$K_i$). Catalytic antibodies with more potent catalytic mechanisms and with higher turnover rates are possible and would reduce the amount of antibody required for clinical application. Increased activity can be pursued either through repeated hybridoma generation or through mutagenesis of catalytic antibodies in hand. However, sequencing of the variable domains of Mab's 3B9 and 6A12 revealed 93% homology at the complementarity determining regions (see below). Such a lack of diversity has been noted previously for catalytic antibodies (10) and limits the opportunities for improving activity since a particular class of homologous catalytic antibodies may fail to optimize to the desired activity. A potential solution to this problem, that would not compromise the core structure of the analog, would be to vary the surfaces of the analog rendered inaccessible by attachment to carrier protein and thereby present distinct epitopes for immunorecognition.

The syntheses of three analogs of cocaine hydrolysis with identical phosphonate replacements but differing constructions for the immunoconjugates is now reported. Seven new catalytic antibodies with the capacity to degrade cocaine (bringing the total of such antibodies to nine) are reported. The kinetics and the structural diversity of the nine catalytic antibodies elicited by these analogs have been characterized. Mabs 15A10 abd 8G4G display a rate of acceleration ($K_{cat}/K_{uncap}$ much greater than the estimated transition-state analog (~$K_m$/$K_i$) indicating that these artificial enzymes employ a potent chemical catalysis mechanism.

SUMMARY OF THE INVENTION

The following standard abbreviations are used throughout the specification to indicate specific amino acids:

E represents Glutamic acid
S represents Serine
R represents Arginine
G represents Glycine
T represents Threonine
I represents Isoleucine
N represents Asparagine
Y represents Tyrosine
C represents Cysteine
P represents Proline
L represents Leucine
W represents Tryptophan
H represents Histidine
D represents Aspartic acid
F represents Phenylalanine
Q represents Glutamine
V represents Valine
K represents Lysine
M represents Methionine
A represents Alanine
X represents any amino acid The invention provides catalytic antibody capable of degrading cocaine characterized by comprising a light chain wherein the amino acid sequence of complementarity determining region 1 is RSSXGTITXXNYAN (Seq ID No: 73), the amino acid sequence of complementarity determining region 2 is XNNYRPP (Seq ID No: 74) and the amino acid sequence of complementarity determining region 3 is ALWYSNHWV (Seq ID No: 75) and a heavy chain wherein the amino acid sequence of complementarity determining region 1 is DYNMY (Seq ID No: 76), the amino acid sequence of complementarity determining region 2 is YIDPXNGXXFYNQKFXG (Seq ID No. 78) and the amino acid sequence of complementarity determining region 3 is GGGLFAX (Seq ID No: 78), wherein X can be any amino acid. In a preferred embodiment, this invention provides the above family of catalytic antibodies comprising antibodies designated 15A10, 19G8 or 9A3.

The present invention also provides a catalytic antibody capable of degrading cocaine comprising a light chain wherein the amino acid sequence of complementarity determining region 1 is RSSSGTITANNYGS (Seq ID No. 40), the amino acid sequence of complementarity determining region 2 is VSNNRGP (Seq ID No: 41) and the amino acid sequence of complementarity determining region 3 is ALWNSNHFV (Seq ID No: 42) and a heavy chain wherein the amino acid sequence of complementarity determining region 1 is TYYIY (Seq ID No: 67), the amino acid sequence of complementarity determining region 2 is GMNPGNGVTYFNEKFKN (Seq ID No: 68) and the amino acid sequence of complementarity determining region 3 is VGNLFAY (Seq ID No: 69). In a preferred embodiment, the catalytic antibody is designated 8G4G.

The present invention also provides a catalytic antibody capable of degrading cocaine comprising a light chain wherein the amino acid sequence of complementarity determining region 1 is RSSXSLLYXDGKTYLN (Seq ID No: 79), the amino acid sequence of complementarity determining region 2 is LMSTRXS (Seq ID No: 80) and the amino acid sequence of complementarity determining region 3 is QXFXXYPFT (Seq ID No: 81) and a heavy chain wherein the amino acid sequence of complementarity determining region 1 is SDYAWX (Seq ID No: 82), the amino acid sequence of complementarity determining region 2 is YIRXXXXTRYNPSLXS (Seq ID No: 83) and the amino acid sequence of complementarity determining region 3 is XHYYGXXX (Seq ID No: 84). In a preferred embodiment, this invention provides the preceding family of catalytic antibodies comprising antibodies designated 3B9, 6A12, 2A10 or 12H1.

The present invention also provides a catalytic antibody capable of degrading cocaine comprising a light chain wherein the amino acid sequence of complementarity determining region 1 is KSSQSLLYSDGKTYLN (Seq ID: 44), the amino acid sequence of complementarity determining region 2 is LVSKLDS (Seq. ID: 45) and the amino acid sequence of complementarity determining region 3 is VQGYTFPLT (Seq ID: 46) and a heavy chain wherein the amino acid sequence of complementarity determining region 1 is DHWMH (Seq ID: 71), the amino acid sequence of complementarity determining region 2 is TIDLSD-TYTGYNQNFKG (Seq ID: 72) and the amino acid sequence of complementarity determining region 3 is RGFDY (Seq ID: 73). In a preferred embodiment, the catalytic antibody is designated 8G4E.

In another embodiment, the present invention provides a polypeptide comprising a heavy chain domain with complementarity determining region 1 having amino acid sequence DYNMY (Seq ID No: 76), complementarity determining region 2 having amino acid sequence YIDPXNGXIFYN-QKFXG (Seq ID No. 78) and complementarity determining region 3 having amino acid sequence GGGLFAX (Seq ID No: 78), interposed between appropriate framework region, said heavy chain domain being linked to a light chain domain with complementarity determining region 1 having amino acid sequence RSSXGTITXXNYAN (Seq ID No: 73), complementarity determining region 2 having amino acid sequence XNNYRPP (Seq ID No: 74) and complementarity determining region 3 having amino acid sequence ALWYSNHWV (Seq ID No: 75) interposed between appropriate framework regions such that said polypeptide assumes a conformation suitable for degrading cocaine. In a preferred embodiment, the complementarity determining regions are derived from the antibodies, 15A10, 19G8 or 9A3.

In another embodiment, the invention provides a polypeptide comprising a heavy chain domain with complementarity determining region 1 having amino acid sequence TYYIY (Seq ID No: 67), complementarity determining region 2 having amino acid sequence GMNPGNGVTYFNEKFKN (Seq ID No: 68) and complementarity determining region 3 having amino acid sequence VGNLFAY (Seq ID No: 69) interposed between appropriate framework regions, said heavy chain domain being linked to a light chain domain with complementarity determining region 1 having amino acid sequence RSSSGTITANNYGS (Seq ID No. 40), complementarity determining region 2 having amino acid sequence VSNNRGP (Seq ID No: 41), complementarity determining region 3 having amino acid sequence ALWN-SNHFV (Seq ID No: 42) interposed between appropriate framework regions such that the polypeptide assumes a conformation suitable for degrading cocaine. In a preferred embodiment, the complementary determining region is derived from the antibody 8G4G.

In another embodiment, the invention provides a polypeptide comprising a heavy chain domain with complementarity determining region 1 having amino acid sequence SDYAWX (Seq ID No: 82), complementarity determining region 2 having amino acid sequence YIRXXXXTRYNPSLXS (Seq ID No: 83) and complementarity determining region 3 having amino acid sequence XHYYGXXX (Seq ID No: 84) interposed between appropriate framework regions, said heavy chain domain being linked to a light chain domain with complementarity determining region 1 having amino acid sequence RSSXS-LLYXDGKTYLN (Seq ID No: 79), complementarity determining region 2 having amino acid sequence LMSTRXS (Seq ID No: 80) and complementarity determining region 3 having amino acid sequence QXFXXYPFT (Seq ID No: 81) interposed between appropriate framework regions such that the polypeptide assumes a conformation suitable for degrading cocaine. In a preferred embodiment, the complementarity determining regions are derived from the antibodies 3B9, 6A12, 2A10 or 12H1.

In another embodiment, the invention provides a polypeptide comprising a heavy chain domain with complementarity determining region 1 having amino acid sequence DHWMH (Seq ID No: 72), complementarity determining region 2 having amino acid sequence TIDLSDTYTGYNQNFKG (Seq ID No: 71) and complementarity determining region 3 having amino acid sequence RGFDY (Seq ID No: 72) interposed between appropriate framework regions, said heavy chain domain being linked to a light chain domain with complementarity determining region 1 having amino acid sequence KSSQSLLYSDGKTYLN (Seq ID No: 43), complementarity determining region 2 having amino acid sequence LVSKLDS (Seq ID No: 44) and complementarity determining region 3 having amino acid sequence VQGYT-FPLT (Seq ID No: 45) interposed between appropriate framework regions such that the polypeptide assumes a conformation suitable for degrading cocaine. In a preferred embodiment, the complementarity determining region is derived from the antibody 8G4E.

The invention further provides a humanized catalytic antibody capable of degrading cocaine. The invention further provides a humanized catalytic polypeptide capable of degrading cocaine.

The invention provides an isolated nucleic acid molecule encoding the light chain of the above-described antibody. Further, the invention provides an isolated nucleic acid molecule encoding the heavy chain of the above-described antibody.

The invention further provides a nucleic acid molecule encoding a single chain polypeptide capable of degrading cocaine.

The present invention further provides a pharmaceutical composition for decreasing the concentration of cocaine in a subject which comprises an amount of the above-described antibody effective to degrade cocaine in the subject's blood and a pharmaceutically acceptable carrier.

The present invention further provides a method of decreasing the concentration of cocaine in a subject which comprises administering to the subject an amount of the above-described antibody effective to degrade cocaine in the subject's blood.

The present invention further provides a pharmaceutical composition for treating cocaine overdose in a subject which comprises an amount of the above-described antibody effective to degrade cocaine in the subject's blood and a pharmaceutically acceptable carrier.

The present invention further provides a method for treating cocaine overdose in a subject which comprises administering to the subject an amount of the above-described antibody effective to degrade cocaine in a subject's blood and reduce cocaine overdose in the subject.

The present invention further provides a pharmaceutical composition for treating cocaine addiction in a subject by diminishing an achievable concentration of cocaine which comprises an amount of the above-described antibody effective to degrade cocaine in the subject and a pharmaceutically acceptable carrier.

The present invention further provides a method for treating cocaine addiction in a subject by diminishing the achievable concentration of cocaine which comprises administering to the subject an amount of the above-described antibody effective to degrade cocaine and thereby diminishing the achievable concentration of cocaine in the subject.

BRIEF DESCRIPTION OF THE FIGURES

FIG. 6. Alignment of amino acid sequences of Lambda light chains.

Figure 1:
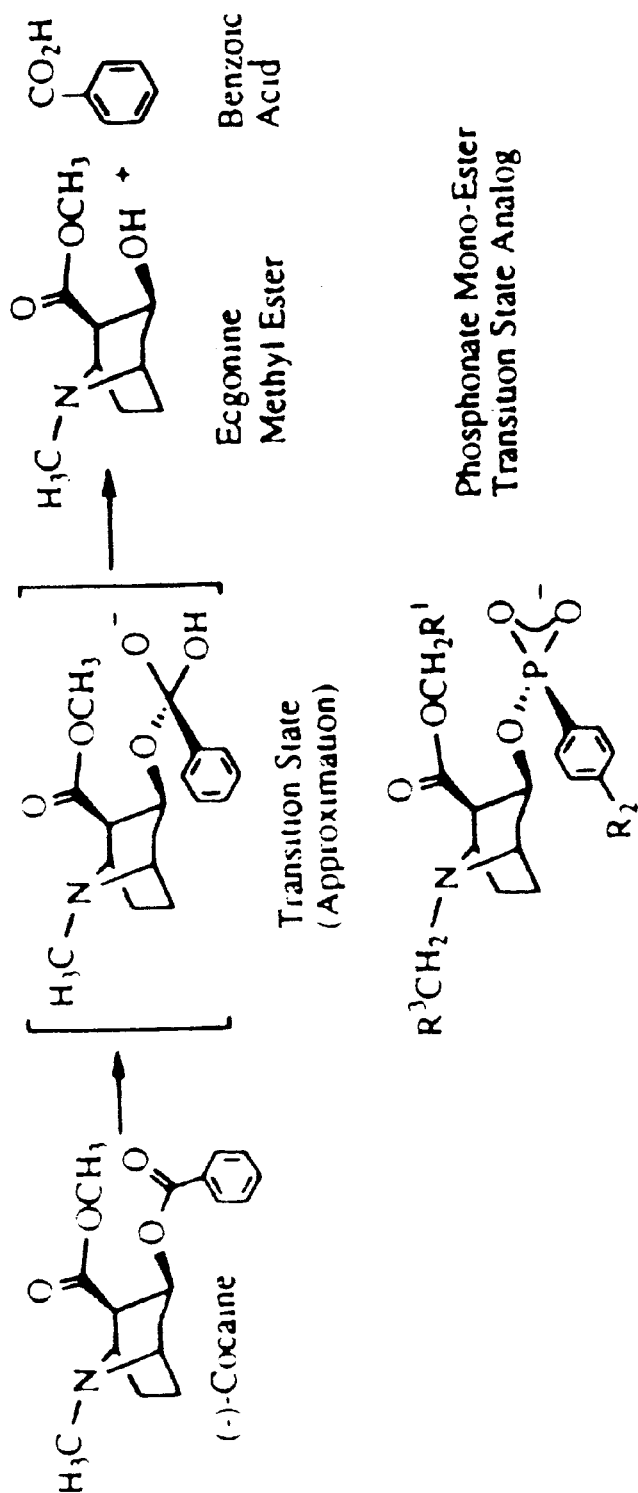
FIG. 1 Hydrolysis of the benzoyl ester of cocaine. Presumed tetrahydral intermediate formed along the reaction pathway is shown. General structure of a phosphonate monoester analogs of the benzoyl ester: TSA 1, TSA 2, TSA 3. TSA 4.

9A(lam9)vari (SEQ ID NO:91:) indicates the amino acid sequence of the variable domain of the Lambda light chain of the antibody 9A3;

19G(lam5) vari (SEQ ID NO:92:) indicates the amino acid sequence of the variable domain of the Lambda light chain of the antibody 19G8;

15A10L Vari (SEQ ID NO:93:) indicates amino acid sequence of the variable domain of the Lambda light chain of the antibody 15A10; and G7(lam4) vari (SEQ ID NO:94:) indicates the amino acid sequence of the variable domain of the Lambda light chain of the antibody 8G4G;

FIG. 7. Alignment of amino acid sequences of Kappa light chains.

3B9 K vari (SEQ ID NO:95:) indicates the amino acid sequence of the variable domain of the Kappa light chain of the antibody 3B9;

6A12 K vari (SEQ ID NO:96:) indicates the amino acid sequence of the variable domain of the Kappa light chain of the antibody 6A12;

12H(L2)k vari (SEQ ID NO:97:) indicates the amino acid sequence of the variable domain of the Kappa light chain of the antibody 12H1;

2A k vari (SEQ ID NO:98:) indicates the amino acid sequence of the variable domain of the Kappa light chain of the antibody 2A10; and E2(L7) k Vari (SEQ ID NO:99:) indicates the amino acid sequence of the variable domain of the Kappa light chain of the antibody 8G4E.

FIG. 8. Alignment of Amino acid sequence of Heavy chains.

3B9 vari (SEQ ID NO:100:) indicates the amino acid sequence of the variable domain of the heavy chain of the antibody 3B9;

6A12 heavy (SEQ ID NO:101:) indicates the amino acid sequence of the variable domain of the heavy chain of the antibody 6A12;

12H H vari (SEQ ID NO:102:) indicates the amino acid sequence of the variable domain of the heavy chain of the antibody 12H1;

2AH-3 (SEQ ID NO:103) indicates the amino acid sequence of the variable domain of the heavy chain of the antibody 2A10;

9(H-3)vari (SEQ ID NO:104:) indicates the amino acid sequence of the variable domain of the heavy chain of the antibody 9A3;

19h6-3 vari (SEQ ID NO:105:) indicates the amino acid sequence of the variable domain of the heavy chain of the antibody 19G8;

15A10 Vari (SEQ ID NO:106:) indicates amino acid sequence of the variable domain of the heavy chain of the antibody 15A10;

E2(H8) Vari (SEQ ID NO:107:) indicates the amino acid sequence of the variable domain of the heavy chain of the antibody 8G4E; and G7(H8) vari (SEQ ID NO:108:) indicates the amino acid sequence of the variable domain of the heavy chain of the antibody 8G4G.

FIG. 9. Nucleotide sequence of the light chain of the anti-cocaine catalytic antibody 15A10 (Sequence ID NO:1).

FIG. 10. Nucleotide sequence of the heavy chain of the anti-cocaine catalytic antibody 15A10 (Sequence ID NO:2).

FIG. 11. Nucleotide sequence of the light chain of the anti-cocaine catalytic antibody 19G8 (Sequence ID NO:3).

FIG. 12. Nucleotide sequence of the heavy chain of the anti-cocaine catalytic antibody 19G8 (Sequence ID NO:4).

FIG. 13. Nucleotide sequence of the light chain of the anti-cocaine catalytic antibody 9A3 (Sequence ID NO:5).

FIG. 14. Nucleotide sequence of the heavy chain of the anti-cocaine catalytic antibody 9A3 (Sequence ID NO:6).

FIG. 15. Nucleotide sequence of the light chain of the anti-cocaine catalytic antibody 8G4G (Sequence ID NO:7).

FIG. 16. Nucleotide sequence of the heavy chain of the anti-cocaine catalytic antibody 8G4G (Sequence ID NO:8).

FIG. 17. Nucleotide sequence of the light chain of the anti-cocaine catalytic antibody 3B9 (Sequence ID NO:9).

FIG. 18. Nucleotide sequence of the heavy chain of the anti-cocaine catalytic antibody 3B9 (Sequence ID NO:10).

FIG. 19. Nucleotide sequence of the light chain of the anti-cocaine catalytic antibody 6A12 (Sequence ID NO:11).

FIG. 20. Nucleotide sequence of the heavy chain of the anti-cocaine catalytic antibody 6A12 (Sequence ID NO:12).

FIG. 21. Nucleotide sequence of the light chain of the anti-cocaine catalytic antibody 2A10 (Sequence ID NO:13).

FIG. 22. Nucleotide sequence of the heavy chain of the anti-cocaine catalytic antibody 2A10 (Sequence ID NO:14).

FIG. 23. Nucleotide sequence of the light chain of the anti-cocaine catalytic antibody 12H1 (Sequence ID NO:15).

FIG. 24. Nucleotide sequence of the heavy chain of the anti-cocaine catalytic antibody 12H1 (Sequence ID NO:16).

FIG. 25. Nucleotide sequence of the, light chain of the anti-cocaine catalytic antibody 8G4E (Sequence ID NO:17).

FIG. 26. Nucleotide sequence of the heavy chain of the anti-cocaine catalytic antibody 8G4E (Sequence ID NO:18).

FIG. 27. The scFv of 3B9 catalytic monoclonal antibody. H1 indicates the complementarity determining region 1 of the heavy chain of the antibody 3B9; H2 indicates the complementarity determining region 2 of the heavy chain of the antibody 3B9; H3 indicates the complementarity determining region 3 of the heavy chain of the antibody 3B9; L1 indicates the complementarity determining region 1 of the light chain of the antibody 3B9; L2 indicates the complementarity determining region 2 of the light chain of the antibody 3B9, L3 indicates the complementarity determining region 3 of the light chain of the antibody 3B9; FLAG indicates an epitope recognized by a known antibody; 6 x His is capable of binding to the metal Nickle; both of the Flag and 6 x His are useful for purifying the scFv.

DETAILED DESCRIPTION OF THE INVENTION

The invention provides catalytic antibody capable of degrading cocaine characterized by comprising a light chain wherein the amino acid sequence of complementarity determining region 1 is RSSXGTITXXNYAN (Seq ID No: 73), the amino acid sequence of complementarity determining region 2 is XNNYRPP (Seq ID No: 74) and the amino acid sequence of complementarity determining region 3 is ALWYSNHWV (Seq ID No: 75) and a heavy chain wherein the amino acid sequence of complementarity determining region 1 is DYNMY (Seq ID No: 76), the amino acid sequence of complementarity determining region 2 is YIDPXNGXXFYNQKFXG (Seq ID No. 78) and the amino acid sequence of complementarity determining region 3 is GGGLFAX (Seq ID No: 78). In a preferred embodiment, this invention provides a family of antibodies comprising 15A10, 19G8 or 9A3.

The present invention also provides a catalytic antibody capable of degrading cocaine comprising a light chain wherein the amino acid sequence of complementarity determining region 1 is RSSSGTITANNYGS (Seq ID No. 40), the amino acid sequence of complementarity determining region 2 is VSNNRGP (Seq ID No: 41) and the amino acid sequence of complementarity determining region 3 is ALWNSNHFV (Seq ID No: 42) and a heavy chain wherein the amino acid sequence of complementarity determining region 1 is TYYIY (Seq ID No: 67), the amino acid sequence of complementarity determining region 2 is GMNPGNGVTYFNEKFKN (Seq ID No: 68) and the amino acid sequence of complementarity determining region 3 is VGNLFAY (Seq ID No: 69). In a preferred embodiment, the catalytic antibody is designated 8G4G.

The present invention also provides a catalytic antibody capable of degrading cocaine comprising a light chain wherein the amino acid sequence of complementarity determining region 1 is RSSXSLLYXDGKTYLN (Seq ID No: 79), the amino acid sequence of Complementarity determining region 2 is LMSTRXS (Seq ID No: 80) and the amino acid sequence of Complementarity determining region 3 is QXFXXYPFT (Seq ID No: 81) and a heavy chain wherein the amino acid sequence of complementarity determining region 1 is SDYAWX (Seq ID No: 82), the amino acid sequence of complementarity determining region 2 is YIRXXXXTRYNPSLXS (Seq ID No: 83) and the amino acid sequence of complementarity determining region 3 is XHYYGXXX (Seq ID No: 84). In a preferred embodiment, this invention provides a family of antibodies comprising 3B9, 6A12, 2A10 or 12H1.

The present invention provides a catalytic antibody capable of degrading cocaine comprising a light chain wherein the amino acid sequence of complementarity determining region 1 is KSSQSLLYSDGKTYLN (Seq ID No: 43), the amino acid sequence of complementarity determining region 2 is LVSKLDS (Seq ID No: 44) and the amino acid sequence of complementarity determining region 3 is VQGYTFPLT (Seq ID No: 45) and a heavy chain wherein the amino acid sequence of complementarity determining region 1 is DHWMH (Seq ID No: 72), the amino acid sequence of complementarity determining region 2 is TIDLSDTYTGYNQNFKG (Seq ID No: 71) and the amino acid sequence of complementarity determining region 3 is RGFDY (Seq ID No: 72). In a preferred embodiment, the catalytic antibody is designated 8G4E.

There are five classes of human antibodies. Each has the same basic structure consisting of two identical polypeptides called heavy chains (molecular weight approximately 50,000 Daltons and two identical light chains, (molecular weight approximately 25,000 Daltons).

Each of the five antibody classes has a similar set of light chains and a distinct set of heavy chains.

A light chain is composed of one variable and one constant domain, while a heavy chain is composed of one variable and three or more constant domains. The combined variable domains of a paired light and heavy chain are known as the Fv region. The Fv determines the specificity of the immunoglobulin, the constant regions have other functions. Amino acid sequence data indicate that each variable domain comprises three hypervariable regions or loops, called complementarity determining regions flanked by four relatively conserved framework regions (24). The hypervariable regions are responsible for the binding specificity of individual antibodies and to account for the diversity of binding of antibodies as a protein class.

In another embodiment, the present invention provides a polypeptide comprising a heavy chain domain with complementarity determining region 1 having amino acid sequence DYNMY (Seq ID No: 76), complementarity determining region 2 having amino acid sequence YIDPXNGXIFYNQKFXG (Seq ID No. 78) and complementarity determining region 3 having amino acid sequence GGGLFAX (Seq ID No: 78), interposed between approprioate framework regions, said heavy chain domain being linked to a light chain domain with complementarity determining region 1 having amino acid sequence RSSXGTITXXNYAN (Seq ID No: 73), complementarity determining region 2 having amino acid sequence XNNYRPP (Seq ID No: 74) and complementarity determining region 3 having amino acid sequence ALWYSNHWV (Seq ID No: 75) interposed between appropriate framework regions such that said polypeptide assumes a conformation suitable for degrading cocaine. In a preferred embodiment, the complementarity determining regions are derived from the antibodies, 15A10, 19G8 or 9A3.

In another embodiment, the invention provides a polypeptide comprising a heavy chain domain with complementarity determining region 1 having amino acid sequence TYYIY (Seq ID No: 67), complementarity determining region 2 having amino acid sequence GMNPGNGVTYFNEKFKN (Seq ID No: 68) and complementarity determining region 3 having amino acid sequence VGNLFAY (Seq ID No: 69) interposed between appropriate framework regions, said heavy chain domain being linked to a light chain domain with complementarity determining region 1 having amino acid sequence RSSSGTITANNYGS (Seq ID No. 40), complementarity determining region 2 having amino acid sequence VSNNRGP (Seq ID No: 41), complementarity determining region 3 having amino acid sequence ALWN-SNHFV (Seq ID No: 42) interposed between appropriate framework regions such that the polypeptide assumes a conformation suitable for degrading cocaine. In a preferred embodiment, the complementarity determining regions are derived from the antibody 8G4G.

In another embodiment, the invention provides a polypeptide comprising a heavy chain domain with complementarity determining region 1 having amino acid sequence SDYAWX (Seq ID No: 82), complementarity determining region 2 having amino acid sequence YIRXXXXTRYNPSLXS (Seq ID No: 83) and complementarity determining region 3 having amino acid sequence XHYYGXXX (Seq ID No: 84) interposed between appropriate framework regions, said heavy chain domain being linked to a light chain domain with complementarity determining region 1 having amino acid sequence RSSXS-LLYXDGKTYLN (Seq ID No: 79), complementarity determining region 2 having amino acid sequence LMSTRXS (Seq ID No: 80) and complementarity determining region 3 having amino acid sequence QXFXXYPFT (Seq ID No: 81) interposed between appropriate framework regions such that the polypeptide assumes a conformation suitable for degrading cocaine. In a preferred embodiment, the complementarity determining regions are derived from the antibody 3B9, 6A12, 2A10 or 12H1.

In another embodiment, the invention provides a polypeptide comprising a heavy chain domain with complementarity determining region 1 having amino acid sequence DHWMH (Seq ID No: 72), complementarity determining region 2 having amino acid sequence TIDLSDTYTGYNQNFKG (Seq ID No: 71) and complementarity determining region 3 having amino acid sequence RGFDY (Seq ID No: 72) interposed between appropriate framework regions, said heavy chain domain being linked to a light chain domain with complementarity determining region 1 having amino acid sequence KSSQSLLYSDGKTYLN (Seq ID No: 43), complementarity determining region 2 having amino acid sequence LVSKLDS (Seq ID No: 44) and complementarity determining region 3 having amino acid sequence VQGYT-FPLT (Seq ID No: 45) interposed between appropriate framework regions such that the polypeptide assumes a conformation suitable for degrading cocaine. In a preferred embodiment, the complementarity determining regions are derived from the antibody 8G4E.

The complementarity determining region of the variable domain of each of the heavy and light chains of native immunoglobulin molecules are responsible for antigen recognition and binding.

It has also been discovered that biosynthetic domains mimicking the structure of the two chains of an immunoglobulin binding site may be connected by a polypeptide linker while closely approaching, retaining and often improving their collective binding properties.

The binding site of the polypeptide comprises two domains, one domain comprises variable domain of an immunoglobulin light chain and the other domain comprises variable domain of an immunoglobulin heavy chain. The two domains are linked by a polypeptide. The polypeptide linker holds the immunoglobulin domains in proper conformation to degrade cocaine.

In a preferred embodiment, the invention provides a hybrid single polypeptide chain comprising variable fragment of a light chain and a variable fragment of an heavy chain, wherein the complementarity determining regions and the framework regions come from separate immunoglobulins.

In another preferred embodiment, the present invention a humanized single chain polypeptide the framework regions are of human or mammalian origin.

Mouse monoclonal antibodies are presently employed as therapeutic agents in human (for example, monoclonal antibody OKT3). However, use of non-human antibodies have certain drawbacks, particularly if repeated administrations is required. Such antibodies contains stretches of amino acid sequences that will be immunogenic when injected into human patient. Studies have shown that, after injection of a foreign antibody, the immune response elicited by a patient against an antibody can be quite strong, essentially eliminating the antibody's therapeutic utility after an initial treatment.

The present invention thus provides hybrid antibodies such as the "humanized" antibodies (e.g. mouse variable regions joined to human or to other mammalian constant regions) by using recombinant DNA technology, capable of degrading cocaine. The claimed hybrid antibodies have one or more complementarity determining regions from one mammalian source, and framework regions from human or other mammalian source.

The hybrid antibodies of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for human-like antibody framework regions and a second sequence set coding for the desired antibody complementarity determining regions can be produced synthetically or by combining appropriate DNA and genomic DNA segments.

In order to decrease the immunogenicity of the hybrid antibody of the present invention, the human-like immunoglobulin, called acceptor, is selected to have one of the most homologous sequences to the corresponding parts of the immunoglobulin donor. The human-like immunoglobulin framework sequence will typically have about 65% to 70% homology or more to the donor immunoglobulin framework sequences.

When combined into an hybrid antibody, the humanized light and heavy chains or complementarity determining regions and framework regions, of the present invention will be substantially non-immunogenic in humans and retain the capacity of degrading cocaine as the donor antibody.

The present invention further provides a pharmaceutical composition for decreasing the concentration of cocaine in a subject which comprises an amount of the claimed antibody effective to degrade cocaine in the subject's blood and a pharmaceutically acceptable carrier.

The present invention further provides a method of decreasing the concentration of cocaine in a subject which comprises administering to the subject an amount of the claimed antibody effective to degrade cocaine in the subject's blood.

The present invention further provides a pharmaceutical composition for treating cocaine overdose in a subject which comprises an amount of the claimed antibody effective to degrade cocaine in the subject's blood and a pharmaceutical acceptable carrier.

The present invention further provides a method for treating cocaine overdose in a subject which comprises administering to the subject an amount of the claimed antibody effective to degrade cocaine in a subject's blood and reduce cocaine overdose in the subject.

The present invention further provides a pharmaceutical composition for treating cocaine addiction in a subject by diminishing an achievable concentration of cocaine which comprises an amount of the claimed antibody effective to degrade cocaine in the subject's blood and a pharmaceutical acceptable carrier.

The present invention further provides a method for treating cocaine addiction in a subject by diminishing the achievable concentration of cocaine which comprises administering to the subject an amount of the claimed antibody effective to degrade cocaine and thereby diminishing the achievable concentration of cocaine in the subject's blood.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

General Methods

Unless otherwise noted, reactions were carried out in oven-dried glassware under an atmosphere of argon. Reagent and solvent transfers were made with oven-dried syringes and needles. Dichloromethane, tetrahydrofuran (THF), and benzene were continuously distilled from calcium hydride; a fumehood was used for procedures requiring benzene or chloroform. $^3H_{phenyl}$-cocaine was prepared as previously reported (8); radiolabeled materials were handled with appropriate caution. All reagents were purchased from Aldrich Chemical Co. All chromatography solvents were obtained commercially and used as received. Reactions were monitored by analytical thin-layer chromatographic methods (TLC) with the use of E. Merck silica gel 60F glass plates (0.25 mm). Flash chromatography was carried out with the use of E. Merck silica gel-60 (230–400 mesh) as described by Still (29). High-pressure liquid chromatography (HPLC) was performed on a system of Waters 590 using a Dynamax-$C_8$ (21.4×250 mm) column and a detector set at 220 nm. Solvent system was acetonitrile-water (0.1% trifluoroacetic acid).

All carbon NMR spectra were obtained at ambient temperature on either a Bruker AMX-500 (500 MHz) spectrometer equipped with a 5 mm broad band inverse probe, Varian VXR-300 (300 MHz) or a Varian Gemini Varian (50 MHz). All proton NMR spectra (400 MHz) were obtained at ambient temperature on a Bruker AM-400 spectrometer, chemical shifts ($\delta$) are reported in parts per million relative to internal tetramethylsilane (0.00 ppm).

FAB high resolution mass spectrometric analysis were performed at Michigan State University, Mass Spectrometry Facility. EI Mass spectrometric analysis were performed at Columbia University, Mass Spectrometry Facility on a JEOL DX303 HF instrument. All results were within 5 ppm of calculated values.

Free TSA 4

Ecgonine methyl ester free base was generated by passing a MeOH solution of ecgonine methyl ester hydrochloride through an Amerlite IRN methoxide-exchange column (Polyscience, Inc). To ecgonine methyl ester (0.049 g, 0.25 mmol) in $CH_2Cl_2$ (10 ml) at 0° C. were added phenylphosphonic dichloride (0.042 ml, 0.30 mmol), 1H-tetrazole (catalytic) and N,N-diisopropylethyl amine (0.11 ml, 3.4 mmol). The reaction was allowed to warn to room temperature. After stirring for 12 h , MeOH (0.150 ml) was added and after 4 h the reaction was concentrated in vacuo. Chromatographic purification ($SiO_2$, $CHCl_3$/MeOH 99:1) afforded the mixed diester 4 (0.042 g, 52%) as an oil. To the methyl ester of 4 (0.030 g, 0.095 mmol) dissolved in $CH_2Cl_2$ (3 ml) was added trimethylsilyl bromide (0.05 ml, 0.38 mmol) at room temperature for 2 h. The reaction was concentrated in vacuo. Water (5 ml) was added and the reaction was extracted with $CHCl_3$ (5 ml×2). The organic portions were extracted with another 5 ml of water. The combined aqueous fractions were concentrated in vacuo. The residue was taken up in MeOH (5 ml) and propylene oxide (excess) was added. After concentration in vacuo, the free TSA 4 (29 mg, 90%) was precipitated as a white solid from a solution of the crude product in $CHCl_3$. $^1H$ NMR (400 MHz, $D_2O$) $\delta$ 7.51 (m, 2H), 7.32 (m, 3H), 4.37 (m, 1H), 3.83 (m, 1H), 3.67 (m. 1H), 3.54 (s, 3H), 2.95 (m, 1H), 2.54 (s, 3H), 2.14–1.92 (m, 3H), 1.91–1.74 (m, 3H). $^{13}C$ NMR (300 MHz, $D_2O$) $\delta$ 179.21, 139.31, 136.92, 136.43, 136.30. 134.00, 133.81, 69.24, 69.04, 68.57, 58.45, 53.49, 43.96, 40.17, 28.95, 27.83; high resolution mass spectrum (FAB) for $C_{16}H_{23}NO_5$ P (M+1) calcd 340.1314, found 340.1319.

Compound 5

To ecgonine HCl (0.35 g, 1.6 mmol) in MeOH (4 ml) were added DMF (40 ml), $Me_4NOH$ (2.7 ml, 6.4 mmol), and 1-azido-4-iodobutane (1.8 g, 8 mmol). The reaction was stirred at 50° C. for 12 h and then concentrated in vacuo. Chromatographic purification ($SiO_2$, EtOAc/MeOH/$_4$NH OH 9:0.9:0.1) afforded the ester (0.35 g, 78%) as an oil: $^1H$ NMR (400 MHz, $CDCl_3$) $\delta$ 4.23 (m, 1H), 4.12 (m, 1H), 3.81 (m, 1H), 3.58 (m, 1H), 3.26 (t, 2H, J=7.0 Hz), 3.18 (m, 1H), 2.74 (t, 1H, J=4.7 Hz), 2.19 (s, 3H), 2.03 (m, 2H), 1.98–1.63 (m, 6H), 1.61–1.47 (m, 2H); $^{13}C$ NMR (500 MHz, $CDCl_3$) $\delta$ 173.73, 64.37, 64.29, 63.56, 61.58, 51.74, 50.94, 41.23, 40.26, 25.92, 25.61, 25.51, 24.82; high resolution mass spectrum (FAB) for $C_{13}H_{23}N_4O_3$ (M+1) calcd 283.1770, found 283.1783.

Compound 6

To alcohol 5 (0.43 g, 1.5 mmol) in benzene (10 ml) at 0° C., were added phenylphosphonic dichloride (0.27 ml, 1.7 mmol), 1H-tetrazole (8 mg), and N,N-diisopropylethyl amine (0.6 ml, 3.4 mmol). The reaction was allowed to warm to room temperature and a precipitate was observed after 15 min. After stirring for 12 h, MeOH (0.1 ml) was added and after 4 h the reaction was concentration in vacuo. Chromatographic purification ($SiO_2$, $CH_3Cl$/MeOH/$_4$NH OH 9.5:0.5:0.02), afforded the mixed diester as a mixture of diastereomers (0.53 g, 89%) as an oil: $^1H$ NMR (400 MHz, $CDCl_3$) $\delta$ 7.73 (m, 2H), 7.60 (m, 1H), 7.49 (m, 2H), 5.09 (m, 1/2H), 4.98 (m, 1/2H), 4.24 (m, 2H), 4.15–3.96 (m, 2H), 3.71 (d, 3/2H, J=14.6 Hz), 3.68 (d, 2H, J=14.6 Hz), 3.35–3.15 (m, 3H), 2.91 (s, 3/2H), 2.89 (s, 3/2H), 2.87 (t, 1/2H, J=7.5 Hz), 2.59 (t, 1/2H, J=7.5 Hz), 2.43–2.22 (m, 5/2H), 2.17–1.95 (m, 5/2H), 1.71–1.57 (m, 2H), 1.39 (m, 2H); $^{13}C$ NMR (500 MHz, $CDCl_3$) $\delta$ 161.55, 149.12, 134.32, 132.55, 129.80, 129.66, 66.72, 66.54, 66.45, 66.28, 64.80, 63.90, 63.81, 53.81, 51.60, 51.50, 49.58, 49.15, 40.30, 35.60, 35.27, 26.35, 26,06, 26.02, 25.82, 25.10, 23.98; high resolution mass spectrum (FAB) for $C_{20}H_{30}N_4O_5$ (M+1) calcd 437.1954, found 437.1953.

Compound 7

$Me_3P$ (1.1 ml, 1M in THF, 1.1 mmol) was added to azide 6 (0.217 g, 0.5 mmol) in 6 ml THF/MeOH/$H_2O$ (9:9:2) and the reaction was stirred at room temperature for 5 h. After concentration in vacuo, the crude unstable amine (36 mg, 0.084 mmol) was taken up in dry $CH_2Cl_2$ (5 ml) and 1, 4-$^{14}C$-succinic anhydride (9 mg, 0.093 mmol) was added. The reaction was stirred under Ar for 12 h and then concentrated. For purification, the crude acid 7 (44 mg, 0.087 mmol) was esterified in $CH_2Cl_2$ (10 ml) with DCC (36 mg, 0.17 mmol), benzyl alcohol (36 μl, 0.35 mmol), and DMAP (cat). The reaction was stirred for 12 h and concentrated. Chromatographic purification (SiO$_2$, 0.5:99.5 MeOH/CHCl$_3$ and 2:98 MeOH/CHCl$_3$) afforded the benzyl ester of 7 as a mixture of diastereomers (32 mg, 59%) as an oil. $^1$H NMR (400 MHz, CDCl$_3$) δ 7.73 (m, 2H), 7.62 (m, 1H), 7.49 (m, 2H), 7.33 (m, 5H), 6.64 (br. s, 1/2H), 6.56 (br. s, 1/2H), 5.10 (s, 2H), 4.96 (m, 1/2H), 4.89 (m, 1/2H), 4.38–3.85 (m, 4H), 3.74 (d, 3/2H, J=15.2 Hz), 3.68 (d, 3/2H, J=15.2 Hz), 3.32–3.12 (m, 3H), 2.89 (s, 3/2H), 2.87 (s, 3/2H), 2.70–2.59 (m, 3H), 2.52–2.26 (m, 4H), 2.10–1.97 (m, 2H), 1.68 (m, 1H), 1.55 (m, 1H), 1.38 (m, 2H); $^{13}$C NMR (500 MHz, CDCl$_3$) δ 173.55, 172.66, 171.37, 161.62, 161.28, 136.59, 134.17, 132.37, 129.56, 129.24, 128.88, 128.71, 67.04, 66.81, 66.64, 66.25, 64.66, 63.75, 53.74, 49.37, 49.00, 40.11, 39.42, 35.55, 35.26, 31.35, 30.31, 26.19, 26.06, 24.89, 23.91; high resolution mass spectrum (FAB) for C$_{31}$H$_{42}$N$_2$O$_8$P (M+1) calcd 601.2679, found 601.2682.

The benzyl ester of 7 (17 mg, 0.028 mmol) in methanol (10 ml) was stirred with a catalytic amount of Pd on C (10%) under H$_2$ (1 atm) for 4 h. The reaction mixture was filtered and concentrated in vacuo to provide acid 7 quantitatively. $^1$H NMR (400 MHz, CD$_3$OD) δ 7.69 (m, 2H), 7.60 (m, 1H), 7.51 (m, 2H), 4.99 (m, 1H), 4.20–4.08 (m, 2H), 3.89 (m, 1H), 3.73 (d, 3/2H, J=21.5 Hz), 3.66 (d, 3/2H, J=21.5 Hz), 3.62 (m, 1H), 3.22 (m, 1H), 3.10 (m, 1H), 3.01 (m, 1H), 2.76 (s, 3/2H), 2.75 (s, 3/2H), 2.50 (m, 2H), 2.38–2.28 (m, 5H), 2.04 (m, 2H), 1.61 (m, 1H), 1.50 (m, 1H), 1.34 (m, 3H); $^{13}$C NMR (500 MHz, CD$_3$OD) δ 176.22, 174.52, 173.47, 162, 22, 134.97, 132.79, 130.18, 67.66, 67.53, 66.99, 65.47, 64.44, 53.89, 39.63, 39.33, 35.99, 31.50, 30.23, 26.71, 24.65, 23.67; high resolution mass spectrum (EI) for C$_{24}$H$_{36}$N$_2$O$_8$P calcd 511.2209 (M+1), found 511.2218.

Compound 8

To the acid 7 (40 mg, 0.078 mmol) dissolved in acetonitrile (5 ml) was added N-hydroxyphthalimide (14 mg, 0.086 mmol) and DCC (32 mg, 0.16 mmol). After 1 h at room temperature a white precipitate formed. The reaction was concentrated in vacuo. The crude activated ester was taken up in CH$_2$Cl$_2$ (5 ml) and trimethylsilyl bromide (100 μl, 0.78 mmol) was added. The reaction was stirred for 1 h and concentrated in vacuo. The crude reaction mixture was taken up in acetonitrile (5 ml) and amylamine (100 μl, 0.78 mmol) was added. A bright orange color developed immediately and faded to light yellow in 1 h. Another portion of amylamine (100 μl) was added. The reaction was stirred for 12 h at room temperature and concentrated in vacuo. Water (3 ml) was added and the reaction was extracted with CHCl$_3$ (5 ml×2). The organic portions were extracted with another 5 ml of water. The combined aqueous fractions were concentrated in vacuo. High pressure liquid chromatography on a Dynamax 300 Å, 12 μ, C-8 (10×250 mm) column eluting with 4%–40% CH$_3$CN/H$_2$O gradient (0.1% trifluoroacetic acid) provided the amide 8 (16 mg, 36% yield). $^1$H NMR (400 MHz, CD$_3$OD) δ 7.72(m, 2H), 7.56(m, 1H), 7.47(m, 2H), 4.12(m, 3H), 3.87(m, 1H), 3.23(m, 2H), 3.14(m, 3H), 2.77(m, 4H), 2.58(m, 4H), 2.34(m, 3H), 2.16(m, 1H), 1.97 (m, 2H), 1.55–1.48(m, 6H), 1.26(m, 4H), 0.846(t, 3H, J=6.3 Hz); $^{13}$C NMR (500 MHz, CD$_3$OD) δ 175.76, 173.62, 133.83, 132.23, 131.01, 129.07, 66.56, 66.52, 65.26, 64.33, 41.13, 40.36, 39.33, 35.93, 31.13, 29.91, 29.48, 28.95, 26.57, 26.28, 24.73, 23.66, 23.22; high resolution mass spectrum (FAB) for C$_{28}$H$_{45}$N$_3$O$_7$P calcd 566.2995 (M+1), found 566.2997.

TSA 1

Acid 7 (14 mg, 0.027 mmol) in CH$_3$CN (5 ml), was stirred at room temperature with N-hydroxyphthalimide (4.8 mg, 0.029 mmol) and DCC (11 mg, 0.053 mmol). A red color developed immediately. After 2.5 h, the reaction was partially concentrated in vacuo, filtered through a small cotton plug and then fully concentrated. The crude, unstable activated ester (0.027 mmol assumed) was taken up in CH$_2$Cl$_2$ (5 ml) and trimethylsilyl bromide (20 μl, 0.15 mmol) was added. The reaction was stirred for 1 h and concentrated in vacuo. BSA (5 mg) or ovalbumin (5 mg) in NaHCO$_3$ (5 ml, 1 N, pH 8.0) at 0° C. was added and the mixture vigorously stirred. The reaction was allowed to warm to room temperature and, after 1 h, terminated by gel filtration chromatography (Sephadex G-25 M, pH 7.4 PBS). Protein-containing fractions were combined and dialyzed against PBS at 4° C. overnight (pH=7.4, 3×1000 ml). The coupling efficiency was estimated to be 6:1 for BSA and 15:1 for ovalbumin based on incorporation of radiolabel.

Compound 9a

To 2-(p-bromophenyl)ethanol (1.3 g, 6.5 mmol) were added methylene chloride (20 ml), t-butyldimethylsilyl chloride (1.07 g, 7.1 mmol) and imidazole (660 mg, 9.7 mmol). The reaction was stirred at room temperature for 12 h, filtered and concentrated in vacuo. Chromatographic purification (SiO$_2$ 95:5 hexane: CHCl$_3$) afforded the silyl ether (1.28 g, 66%). To the ether (792 mg, 2.51 mmol) in THF (25 ml) under Ar at −78° C. was added n-BuLi (1.2 ml, 2.3 M hexanes, 2.76 mmol) dropwise. The reaction was stirred for 30 min and a solution of diethylchlorophosphate (370 μl, 2.5 M THF, 0.93 mmol) was added. The reaction was stirred at −78° C. for an additional 5 min and allowed to warm to room temperature. Aqueous NH$_4$Cl (20 ml) was added and the reaction was extracted with EtOAc (3×10 ml). The combined organic layers were washed with brine, dried with anhydrous MgSO$_4$, filtered, and concentrated in vacuo. THF (10 ml) and aq Bu$_4$NF (2.5 ml, 1 M, 2.5 mmol) were added to the residue. This solution was stirred at room temperature for 30 min and concentrated in vacuo. Chromatographic purification (SiO$_2$, 9:1 EtOAc/MeOH), provided the alcohol 9a (229 mg, 35%). $^1$H NMR (400 MHz, CDCl$_3$) δ 7.74 (dd, 2H, J=12.5, 7.1 Hz), 7.33 (dd, 2H, J=12.5, 4.5 Hz), 4.11 (m, 4H), 2.92 (t, 2H, J=6.5 Hz), 2.89 (t, 2H, J=6.5 Hz), 1.32 (t, 6H, J=7.8 Hz). $^{13}$C NMR (50 MHz, CDCL$_3$) δ 144.32, 132.51, 129.78, 129.47, 63.61, 62.69, 39.74, 16.98; high resolution mass spectrum (EI) for C$_{12}$H$_{20}$O$_4$P calcd 259.1099 (M+1), found 259.1092.

Compound 9b

To alcohol 9a (193 mg, 0.75 mmol) were added CH$_2$Cl$_2$ (7.5 ml), Et$_3$N (115 μl, 0.83 mmol), TsCl (145 mg, 0.75 mmol), DMAP (catalytic). The reaction was stirred at room temperature for 12 h. Concentration and purification (SiO$_2$, 3:1 EtOAc:hexane) provided the tosylate (251 mg, 81.5%) and to a portion of this product (232 mg, 0.56 mmol) were added benzene (3 ml), water (3 ml), tricaprylmethyl ammonium chloride (cat.), and NaN$_3$ (150 mg, 2.25 mmol). The reaction was refluxed at 65° C. for 12 h. Saturated aq NH$_4$Cl (5 ml) was added, and the reaction was extracted with EtOAc. The combined organic layers were treated with MgSO$_4$, filtered, and dried in vacuo. Chromatography (SiO$_2$, 1:1 hexane:EtOAc) afforded the azide 9b (137 mg, 86%). $^1$H NMR (400 MHz, CDCl$_3$) δ 7.74 (dd, 2H, J=12.5, 7.1 Hz), 7.32 (dd, 2H, J=12.5, 4.5 Hz), 4.09 (m, 4H), 3.86 (t, 2H, J=7.5 Hz), 2.92 (t, 2H, J=7.5 Hz), 1.32 (t, 6H, J=7.3 Hz). $^{13}$C NMR (50 MHz, CDCl$_3$) δ 143.31, 132.65, 129.50, 129.20, 125.31, 62.58, 52.47, 35.89, 16.94; high resolution mass spectrum (EI) for C$_{12}$H$_{19}$N$_3$O$_3$ P calcd 284.1164 (M+1), found 284.1168.

Compound 10

Diethyl phosphonate ester 8b (600 mg, 2.12 mmol) in CH$_2$Cl$_2$ (5 ml) were stirred with trimethylsilyl bromide (1 ml, 11 mmol) and warmed to 45° C. After 20 min, it was concentrated in vacuo. The residue was dissolved in $CH_2Cl_2$ (3.2 ml), oxalyl chloride (3.2 ml, 2M in $CH2Cl_2$, 6.36 mmol) and one drop of DMF were added. After stirring 20 min at room temperature, the volatiles was removed in vacuo. The unstable phosphonic dichloride was used directly.

Compound 11

Ecgonine methyl ester free base was generated as described for compound 4. To ecgonine methyl ester (170 mg, 0.854 mmol) in benzene (20 ml) at 0° C. was added N,N-diisopropylethylamine (0.74 ml, 4.26 mmol), 1H-tetrazole (catalytic) and the phosphonic dichloride 10 (225 mg, 0.854 mmol). The reaction was allowed to warm to room temperature and stirred for 12 h. Methanol (3 ml) was added and after 20 min the reaction mixture was concentrated in vacuo. Chromatographic purification ($SiO_2$, 1:9 $MeOH:CHCl_3$) afforded the mixed diester as a mixture of diastereomers (108 mg, 30%). $^1$H NMR (400 MHz, $CDCl_3$) δ 7.71 (m, 2H), 7.29 (m, 2H), 4.63 (m, 1H), 3.73 (s, 3/2H), 3.70 (s, 3/2H), 3.63 (d, 3/2H, J=11.4 Hz), 3.62 (d, 3/2H, J=11.4 Hz), 3.51 (t, 2H, J=7.2 Hz), 3.48–3.39 (m, 1H), 3.23–3.15 (m, 1H), 3.05 (m, 1/2H), 2.91 (t, 2H, J=7.2 Hz), 2.75 (m, 1/2H), 2.57–2.26 (m, 1H), 2.14 (s, 3H) 2.09–1.52 (m, 5H). $^{13}$C NMR (50 MHz, $CDCl_3$) δ 170.91, 170.65, 143.27, 132.80, 132.61, 129.45, 129.11, 125.08, 78.22, 77.73, 76.95, 70.15, 65.31, 62.14, 52.50, 52.84, 52.15, 41.56, 37.84, 35.97, 25.70, 25.58; high resolution mass spectrum (EI) for $C_{19}H_{27}N_4O_5P$ calcd 422.1719 (M$^+$), found 422.1714.

Compound 12

To azide 11 (370 mg, 0.877 mmol) was added THF (9 ml) and triphenylphosphine (400 mg, 1.75 mmol). After stirring at r.t. for 12 h, water (1 ml) was added. The mixture was stirred for 3 h and concentrated in vacuo. To the crude amine (200 mg, 0.51 mmol) were added $CH_2Cl_2$ (7.5 ml) and succinic anhydride (3.5 mg, 0.35 mmol). The reaction was stirred for 12 h and concentrated in vacuo. The crude acid 12 (290 mg, 0.51 mmol) was dissolved in $CH_2Cl_2$ (10 ml) and DCC (200 mg, 0.97 mmol), DMAP (catalytic) and benzyl alcohol (0.2 ml, 1.9 mmol) were added. The reaction was stirred at room temperature for 12 h and concentrated in vacuo. Chromatography $SiO_2$, 10:10:0.4 $CHCl_3:EtOAc:NH_4OH$) afforded the benzyl ester of 12 (197 mg, 65%) as a mixture of diastereomers. $^1$H NMR (400 MHz, $CDCl_3$) δ 7.79–7.61 (m, 4H), 7.33–7.25 (m, 5H), 5.11 (s, 2H), 4.69–4.58 (m, 1H), 3.73 (s, 3/2H), 3.69 (d, 3/2H, J=18.1 Hz), 3.62 (d, 3/2H, J=18.1 Hz), 3.59 (s, 3/2H), 3.46 (m, 2H), 3.27–3.03 (m, 3H), 2.81 (t, 2H, J=7.2 Hz), 2.69 (t, 2H, J=6.8 Hz), 2.42 (t, 2H, J=6.8 Hz), 2.15 (s, 3H), 2.08–1.80 (m, 3H), 1.69–1.51 (m, 3H). $^{13}$C NMR (50 MHz, $CDCl_3$) δ 173.35, 171.42, 132.38, 132.11, 129.99, 129.93, 129.80, 129.67, 129.61, 129.56, 129.48, 129.94, 128.66, 128.49, 67.07, 66.16, 66.43, 63.40, 53.28, 50.49, 50.18, 50.06, 49.64, 49.36, 49.21, 48.79, 39.58, 36.14, 31.14, 30.07, 24.73; high resolution mass spectrum (EI) for $C_{30}H_{39}N_2O_8P$ calcd 586.2444 (M$^+$), found 586.2428.

Acid 12 was quantitatively regenerated from the benzyl ester as described for acid 7 as a mixture of diastereomers. $^1$H NMR(400 MHz, $CDCl_3$) δ 7.74 (m, 2H), 7.60 (m, 1H), 7.49 (m, 2H), 5.02 (m, 1/2H), 4.92 (m, 1/2H), 4.24 (m, 2H), 3.83 (s, 3/2H), 3.74 (d, 3/2H, J=12 Hz), 3.67 (d, 3/2H, J=12 Hz), 3.51 (s, 3/2H), 2.79 (m, 1H), 2.75 (s, 3/2H), 2.74 (s, 3/2H), 2.45 (m, 1H), 2.35 (m, 6H), 2.02 (m, 2H), 1.20 (m, 4H); $^{13}$C NMR (300 MHz, $CD_3$ OD) δ 175.92, 174.33, 173.72, 147.06, 132.85, 132.72, 130.62, 130.41, 129.56, 129.29, 67.31, 65.28, 64.37, 53.69, 53.43, 53.24, 41.25, 39.21, 36.42, 35.83, 35.70, 31.35, 30.58, 30.07, 24.52, 23.50; high resolution mass spectrum (EI) for $C_{23}H_{34}N_2O_8P$ calcd 497.2053 (M+1), found 497.2064.

Compound 13

To the acid 12 (23 mg, 0.049 mmol) dissolved in acetonitrile (5 ml) was added N-hydroxyphthalimide (9 mg, 0.054 mmol) and DCC (20 mg, 0.097 mmol). Reaction with trimethylsilyl bromide (0.65 ml, 0.49 mmol) and amylamine (0.57 ml, 0.47 mmol) proceeded by the protocols developed for compound 8 to yield amide 13 (8 mg, 30% yield). $^1$H NMR: (400 MHz, $CD_3OD$) 7.69 (m, 2H), 7.32 (m, 2H), 4.75 (m, 1H), 4.08 (m, 1H), 3.86 (m, 1H), 3.71 (s, 3H), 3.39 (m, 3H), 3.14 (m, 2H), 2.82 (m, 5H), 2.42 (s, 3H), 2.38–2.22 (m, 4H), 2.13–2.00 (m, 3H), 1.49 (m, 2H), 1.32 (m, 4H), 0.91 (t, 3H, J=1.5Hz) $^{13}$C NMR (500 MHz, $CD_3OD$) δ 173.39, 159.53, 159.22, 144.10, 132.23, 130.95, 129.61, 117.04, 64.83, 64.62, 64.12, 63.92, 62.53, 40.89, 39.54, 36.83, 36.23, 34.31, 31.21, 30.52, 30.14, 29.24, 27.94, 23.95, 21.47; high resolution mass spectrum EI for $C_{27}H_{43}N_3O_7P$ calcd 552.2839 (M+1), found 552.2863.

TSA 2

To acid 12 (70 mg, 0.14 mmol) were added DMF (4 ml), DCC (116 mg, 0.57 mmol), and N-hydroxyphthalimide (92 mg, 0.57 mmol) at r.t. The reaction was stirred for 12 h at 4° C., concentrated in vacuo and filtered through a small cotton plug rinsing with $CHCl_3$ (10 ml). To an aliquot of this solution (2 ml) was added bromotrimethylsilane (0.1 ml, 0.76 mmol). Work-up and coupling proceeded by the protocol developed for TSA 1. The coupling efficiency to BSA was 15 to 1; to ovalbumin 10 to 1.

Compound 14

To N-norcocaine (206 mg, 0.713 mmol) and N,N-diisopropyethylamine (186 μl, 1.07 mmol) in THF (30 ml) was added 1-azido-4-iodobutane (160 mg, 0.713 mmol) at r.t. The reaction mixture was heated to 60° C. for 2 days. Concentration in vacuo and chromatographic purification ($SiO_2$ 1:9 EtOAc hexane) yielded the ecgonine ester 14 (205 mg, 75%) as a colorless oil. $^1$H NMR (400 MHz, $CDCl_3$) δ 8.02 (d, 2H, J=6.0 Hz), 7.58 (t, 1H, J=6.1 Hz), 7.41 (t, 2H, J=7.0 Hz), 5.25 (m, 1H), 3.70 (s, 3H), 3.68 (m, 1H), 3.50 (m, 1H), 3.28 (t, 2H, J=7.4 Hz), 3.03 (m, 2H), 2.43 (m, 1H), 2.26 (m, 2H), 2.04–2.00 (m, 2H), 1.86 (m, 1H), 1.73–1.65 (m, 4H), 1.47 (m, 2H); $^{13}$C NMR (500 MHz, $CDCl_3$) δ 171.47, 166.96, 133.77, 131.24, 130.59, 129.16, 68.10, 63.55, 61.24, 52.89, 52.21, 52.05, 53.13, 36.49, 27.29, 26.95, 26.86, 26.34; high resolution mass spectrum (FAB) for $C_{20}H_{27}N_4O_4$ (M+1) calcd 387.2032, found 387.2041.

Compound 15

N-substituted cocaine 14 (205 mg, 0.53 mmol) was hydrolyzed with aq HCl (10 ml, 0.7 N) at 90° C. for 4 h. The mixture was extracted with ether, concentrated and dissolved in MeOH (25 ml) saturated with HCl(g). After 2 h at 60°, solvent was removed under vacuum, and the residue was dissolved in MeOH and passed through an Amberlite IRN methoxide-exchange column (Polysciences, Inc) (1 ml) to generate the crude free base. Chromatographic purification ($SiO_2$ 5:95 $MeOH:CHCl_3$) afforded alcohol 15 (102 mg, 72%). $^1$H NMR (400 MHz, $CDCl_3$) δ 3.80 (m, 1H), 3.69 (s, 3H), 3.03 (m, 1H), 3.66 (m, 2H), 3.24 (t, 2H, J=7.2 Hz), 3.18 (m, 1H), 2.75 (t, 1H, J=5.1 Hz), 2.21 (m, 1H), 1.95–1.78 (m, 4H), 1.61–1.38 (m, 6H); $^{13}$C NMR (500 MHz, $CDCl_3$) δ 169.58, 65.55, 62.89, 61.27, 53.10, 52.61, 52.26, 52.18, 41.20, 27.36, 27.08, 27.02, 25.83; high resolution mass spectrum (FAB) for $C_{13}H_{23}N_4O_3$ (M+1) calcd 283.1770, found 283.1779.

Compound 16

To the ecgonine derivative 15 (102 mg, 0.37 mmol) in benzene (15 ml) at 0° C. were added 1H-tetrazole(catalytic), N,N-diisopropylethyl amine (0.163 ml, 0.94 mmol) and phenylphosphonic dichloride (0.67 ml, 0.47 mmol). The reaction mixture was allowed to warm to room temperature overnight. Excess MeOH was added and the mixture was stirred at room temperature for 3 h. Chromatographic purification ($SiO_2$ 5:95 of 4% $NH_4OH$ in MeOH and a 1:1 mixture of hexane and $CHCl_3$) and prep-TLC (2.5:97.5 MeOH: $CH_2Cl_2$) afforded the mixed diester 16 as a mixture of diastereomers (78 mg, 49%). $^1$H NMR (400 MHz, $CDCl_3$) δ 7.66 (m, 2H), 7.62 (m, 1H), 7.49 (m, 2H), 5.08 (m, 1/2H), 4.97 (m, 1/2H), 4.32 (m, 1H), 4.18 (m, 1H), 3.88 (s, 3/2H), 3.75 (d, 3/2H, J=16.4 Hz), 3.71 (d, 3/2H, J=16.4 Hz), 3.49 (s, 3/2H), 3.45–3.25 (m, 4H), 2.98 (m, 1H), 2.63–2.22 (m, 4H), 2.19–2.01 (m, 2H), 1.92–1.63 (m, 4H); $^{13}$C NMR (500 MHz, $CDCl_3$) δ 160.10, 159.72, 133.37, 133.23, 131.61, 131.53, 131.46, 130.29, 128.86, 128.76, 128.64, 66.76, 63.74, 63.58, 62.55, 62.43, 54.46, 54.17, 52.64, 51.67, 49.11, 48.79, 36.57, 36.28, 26.91, 25.58, 25.18, 24.18; high resolution mass spectrum (FAB) for $C_{20}H_{30}N_4O_5P$ (M+1) calcd 437.1954, found 437.1928.

Compound 17

$Me_3P$ (0.156 ml, 1 M, in THF, 0.157 mmol) was added to azide 16 (12 mg, 0.026 mmol) in MeOH (5 ml) and the reaction was stirred at room temperature for 2 h. After concentration in vacuo, the crude amine was taken up in $CH_2Cl_2$ (5 ml), succinic anhydride (2.6 mg, 0.026 mmol) was added. The reaction mixture was stirred at room temperature overnight and concentrated. The crude acid 17 was dissolved in $CH_2Cl_2$ (10 ml) and benzyl alcohol (0.05 ml, 0.048 mmol), DCC (10 mg, 0.048 mmol), and DMAP (catalytic) was added. The reaction was stirred overnight at r.t. and concentrated. Column chromatography ($SiO_2$, 5:95 MeOH:$CHCl_2$) and prep-TLC (5:95 MeOH $CH_2Cl_2$) afforded the benzyl ester as a mixture of diastereomers (11 mg, 70% from 13). $^1$H NMR (400 MHz, $CDCl_3$) δ 7.76 (m, 2H), 7.63 (m, 1H), 7.51 (m, 2H), 7.32 (m, 5H), 7.01 (br s, 1H), 5.09 (s, 2H), 5.03 (m, 1/2H), 4.94 (m, 1/2H), 4.29–4.09 (m, 2H), 3.83 (s, 3/2H), 3.77 (d, 3/2H, J=17.1 Hz), 3.69 (d, 3/2H, J=17.1 Hz), 3.49 (s, 3/2H), 3.38–3.22 (m, 4H), 3.01 (m, 2H), 2.69–2.33 (m, 8H), 2.04–1.60 (m, 6H); $^{13}$C NMR (500 MHz, $CDCl_3$) δ 172.94, 172.68, 172.09, 135.86, 133.30, 131.64, 128.90, 128.78, 128.65, 128.54, 128.17, 128.82, 66.24, 65.81, 62.71, 62.54, 61.16, 61.03, 52.95, 51.49, 47.69, 37.64, 35.18, 30.41, 29.39, 25.67, 24.00, 23.54, 21.95; high resolution mass spectrum (FAB) for $C_{31}H_{42}N_2O_8P$ (M+1) calcd 601.2679, found 601.2676.

Acid 17 was quantitatively regenerated from the benzyl ester as described for acid 7. $^1$H NMR(400 MHz, $CDCl_3$) δ 7.74 (m, 2H), 7.60 (m, 1H), 7.48 (m, 2H), 5.02 (m, 1/2H), 4.92 (m, 1/2H), 4.33–4.09 (m, 2H), 3.83 (s, 3/2H), 3.74 (d, 3/2H, J=23 Hz), 3.67 (d, 3/2H, J=23 Hz), 3.51 (s, 3/2H), 3.33–3.19 (m, 6H), 2.98 (m, 1H), 2.63 (m, 2H), 2.49 (m, 4H), 2.34 (m, 2H), 2.06–1.96 (m, 2H), 1.81–1.76 (m, 2H), 1.57 (m, 2H); $^{13}$C NMR (300 MHz, $CDCl_3$) δ 175.23, 173.41, 172.06, 133.21, 131.65, 128.90, 128.58, 65.87, 62.75, 60.89, 53.30, 52.98, 51.54, 48.16, 47.75, 37.61, 31.02, 30.33, 25.76, 24.15, 23.54, 21.92; high resolution mass spectrum (EI) for $C_{28}H_{36}N_2O_8P$ calcd 511.2209 (M+1), found 511.2213.

Compound 18

To acid 17 (6 mg, 0.012 mmol) dissolved in $CH_3CN$ (3 ml) was added N-hydroxyphthalimide (2.2 mg, 0.013 mol) and DCC (5 mg, 0.024 mmol). Reaction with trimethylsilyl bromide (0.016 ml, 0.12 mmol) and the amylamine (0.14 ml, 0.012 mmol) proceeded by the protocols developed for compound 8 to yield amide 4 (4.4 mg, 65%). $^1$H NMR: (400 MHz, $CD_3OD$) δ 7.81 (m, 2H), 7.56–7.38 (m, 3H), 5.95 (m, 1H), 5.39 (m, 1H), 5.05 (m, 1H), 4.79 (s, 3H), 4.29–4.12 (m, 6H), 3.61–3.04 (m, 10H), 2.83–2.34 (m, 11H), 0.94 (t, 3H, J=7.2 Hz). $^{13}$C NMR (300 MHz). δ 175.12, 174.98, 174.39, 132.49, 129.36, 129.21, 65.79, 64.72, 62.26, 53.33, 52.52, 40.44, 39.01, 36.78, 32.17, 31.91, 30.23, 30.14, 27.39, 24.69, 24.32, 23.45, 23.22, 14.36; high resolution mass spectrum (FAB) for $C_{28}H_{45}N_3O_7P$ (M+1) calcd 566.2995, found 566.2997.

TSA 3

To the acid 17 (12 mg, 0.023 mmol) and N-hydroxyphthalimide (16 mg, 0.096 mmol) in DMF (2 ml) was added DCC (19 mg, 0.096 mmol). The reaction was stirred at 4° C. overnight, concentrated in vacuo, and filtered with $CHCl_3$ (10 ml) The activated ester was kept as a $CHCl_3$ solution (10 ml) at −20° C. and used without purification. Trimethylsilyl bromide (0.050 ml, 0.379 mmol) was added to a 5 ml aliquot of the activated ester at room temperature. Work-up and coupling proceeded by the protocol developed for TSA 1. The coupling ratio to BSA was 11:1; to ovalbumin 12:1.

Hybridoma Generation

As previously described (9), BALB/c mice were immunized with the analog-carriers and the immune response was followed by ELISA. Hybridomas were prepared by standard methods (9,17).

Hybridoma cells (~2×10$^6$) were placed either into a mouse peritoneum that had been pretreated with pristane or into T-150 flask cell culture. The harvested ascites or cell culture super natents were subjected to affinity chromatography on a preparative protein A HPLC column (Bio-Rad) (purity>90% by SDS-polyacrylamide gel electrophoresis). Samples of catalytically active antibodies were purified by anion exchange HPLC with an analytic DEAE column (TOSOH HASS TSK-gel) using 0.02 M Tris and a linear gradient pH 8.8/0.0 M NaCl to pH 7.0/0.3 M NaCl without loss of cocaine esterase activity.

Protocol for Binding Studies (CIEIA)

Plates were coated with the TSA (tethered to ovalbumin) that elicited the catalytic antibody intended for CIEIA. Free TSA 4 or the TSA-related amides 8, 13, or 14, were tested for inhibition of antibody binding to the eliciting TSA by published protocols (20b).

Protocol for Kinetic Measurements

Catalytic antibody in 50 mM phosphate-buffered saline pH 8.0 (except 2A10 and 6A12 at pH 7.0) was incubated with $^3$H-cocaine typically at five concentrations. At three time intervals, aliquots were acidified with cold HCl (aqueous) to a final pH of 2 and partitioned with hexane-diethyl ether (1:1), and the organic phase was assayed by scintillation counting. Background hydrolysis was determined in otherwise identical reactions without antibody, and observed rates were corrected. Assays were performed in triplicate with standard error <10%. As a control, the release of benzoic acid was confirmed by HPLC (Perkin-Elmer) using an analytical reverse-phase $C_{18}$ column (VYDAC) with an acetonitrile-water (0.1% trifluoroacetic acid) gradient and the detector set at 220 nm.

HPLC analysis of a reaction mixture without antibody showed that the methyl ester of cocaine spontaneously hydrolyzes to benzoyl ecgonine with a $t_{1/2}$=20 hours (pH 7). Thus, benzoyl ecgonine is not available as a benzoyl esterase substrate at the early reaction times of the $^3$H-cocaine hydrolysis assay and the release of benzoic acid is attributed solely to cocaine hydrolysis.

Amino Acid Sequencing

Light and heavy chains were separated by SDS-polyacrylamide gel electrophoresis and then electroblotted to a polyvinylidenedifluoride membrane (30) for direct $NH_2$-terminal sequencing by automated Edman degradation on an Applied Biosystems 470A or 477A sequencer. To obtain internal sequence, separated bands from 2A10, 19G7, 9A3 and 15A10 were reduced with dithiothreitol, alkylated with iodoacetamide, and cleaved with trypsin (31), 0.05 M $NH_4HCO_3$, pH 8.0. The peptide fragments were extracted from the membrane, separated by HPLC (Hewlett-Packard) on a reverse-phase C18 column (VYDAC) using an acetonitrile-water (0.07% trifluoroacetic acid) gradient and sequenced.

Pcr Cloning of Variable Domains

Mouse hybridoma cell lines producing catalytic antibodies were grown to $1 \times 10^8$ cells and total RNA was prepared using a microadaptation of the guanidine thiocyanate/phenol procedure (32) and selection on a oligo (dT) cellulose column.

Degenerate and non-degenerate oligonucleotide PCR primers were designed using amino acid sequences (2A10, 15A10) or the data base of Kabat et al. (24). Restriction endonuclease sites were incorporated into the primers at their 5' prime end to facilitate cloning. The restriction sites utilized were Eco RI, Spe I, Xba I, or Xho I. The sense and antisense oligonucleotide primers for light chain (LC) and heavy chain (HC) of each hybridoma line were as follows: For 9A3, 19G8, 15A10, 8G4E and 8G4G LC: 5'-GGAATTCCACIA/TC/GICCIGGIGAA/GACIG-3' and 5'GCTCGAGCC/TTCA/GTGIGTIACITGA/GCA-3'. For 3B9, 6A12 and 12H1 LC: 5'-CCAGTTCCGAGCTCCAGATGACCCAGTCTCCA-3' and 5'-GCGCCGTCTAGAATTAACACTCA TTCCTGT TGAA-3'. For 2A10 LC: 5'-GCTCTAGAGCGAT/ CATIGTIATGACICAA/GGAT/CGA-3' and 5'-GGAATTCCA/GTTA/GTGICT/CT/CTCA/GTAT/ CTCA/GTC-3'. For 3B9, 6A12, 12H1, 9A3, 19G8, 8G4E and 84G4G HC: 5'-AGGTCCAGCTGC TCGAGTCTGG-3' and 5'-AGGCTTACTAGTACAATCCCTGGGCACAAT-3'. For 2A10 HC: 5'-TCCCAGGTCCAACTGCAGCAGCC-3' and 5'-ATAACCCTTGACCAGGCATCC-3'. For 15A10 HC: 5'-CCAGTTCCGAGCTCGTGATGACACAGTCTCC-3' and 5'-AGCGCCGTCTAGAATTAACACTCATTCCTGTTGAA-3'.

DNA templates were synthesized using 0.5 μg of hybridoma mRNA and Moloney murine leukemia virus reverse transcriptase. Amplifications were carried out in a Perkin-Elmer/Cads thermal cycler for 30 cycles of denaturation (96° C., 1 min), annealing (50° C., 1 min), and extension (72° C., 3 min). The PCR products were purified by electrophoresis in 1.5% agarose gel. Isolated PCR products from each reaction were subcloned into Bluescript plasmid and analyzed by DNA sequence analysis for the presence of open reading frame. Nucleotide sequences were assembled using the IBI MacVector 3.0 program.

EXPERIMENTAL RESULTS

Synthesis of Transition-state Analogs

Phosphonate monoesters, which stably mimic the geometry and charge distribution of the transition-state for 2nd-order ester hydrolysis by hydroxide, have yielded, in some instances, catalytic antibodies of high activity (8). However, such analogs are also known to idiosyncratically fail to elicit any catalytic antibodies and so the rules for analog construction must be defined empirically (11). Strategies to improve analog efficiency have been devised, including "bait and switch" (11) and substrate attenuation (12), but the cost of such expedients is a divergence between analog and substrate structure which results on average in catalytic antibodies with higher values for $K_m$. Inhalation of vaporized cocaine yields a peak pulmonary vein concentration (13) of 10–30 μM and this is less than the $K_m$ of most catalytic antibodies with esterase activity. At a sub-saturating concentration of cocaine, a higher $K_m$ would result in a lower turnover rate and increase the already limiting requirement for a high $k_{cat}$. Thus, the construction of a high fidelity analog that differed from cocaine only by a phosphonate replacement at the acyl group and by the incorporation of a tether for construction of an immunogenic conjugate has been chosen. Based on their distances from the locus of reaction and their separation from each other, three tether sites were chosen: at the methyl ester for analog 1, the 4'-position of the phenyl group for analog 2, and the tropane nitrogen for analog 3 (FIG. 1). The "free TSA" corresponded to the untethered structure 4.

Figure 2:
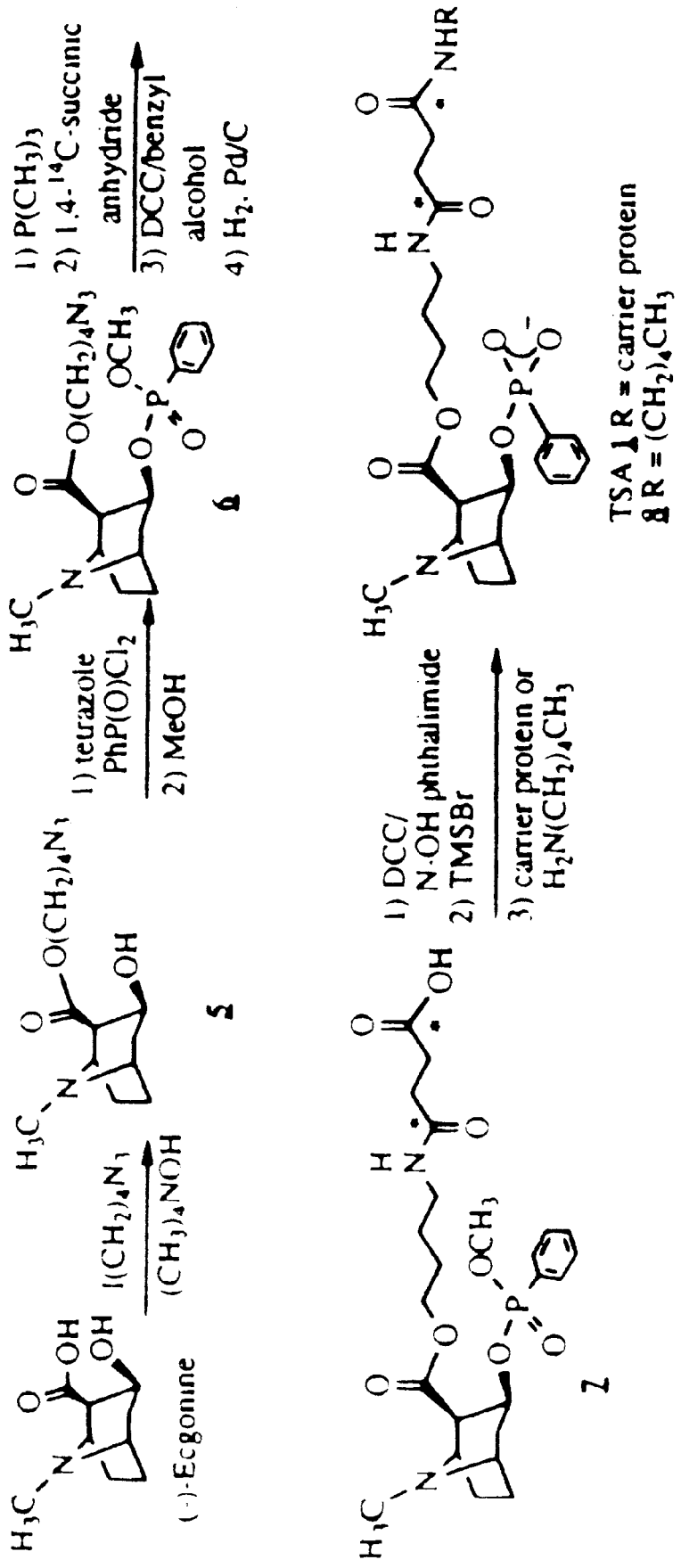
FIG. 2. Synthesis of TSA-1.

The synthesis of TSA 1 began with the commercially available starting material (−)-ecgonine (FIG. 2). Selective alkylation of the carboxylate salt of (−)-ecgonine with 4-azido-1-iodo-butane yielded ester 5 in 78% yield. The absence of epimerization at C-2 was confirmed by $^1$H-nmr spectroscopy. The base labile and sterically hindered alcohol of alkyl ecgonine 5 reacted smoothly with phenylphosphonic dichloride using the procedure for 1H-tetrazole catalysis (14) and addition of methanol provided the phosphonate diester 6 in 89% yield. The tether was elaborated at the azido moiety by reduction to the unstable amine with $P(CH_3)_3$ and acylation with 1,4-$^{14}$C-succinic anhydride. The hemisuccinate was purified and characterized as the benzyl ester, obtained in 70% yield from 6, and the acid was quantitatively regenerated by catalytic hydrogenolysis. Acid 7 was activated as the N-hydroxyphthalimide ester and selectively deesterified at the phosphonate methyl ester with trimethylsilyl bromide (15). The unstable monophosphonate product was immediately coupled to carrier protein to yield TSA-1. The analog:carrier coupling ratio was 6:1 for bovine serum albumin (BSA) and 15:1 for ovalbumin based on the incorporation of radiolabel into protein. In support of our assignment of structure to the carrier-bound analog, an aliquot of the monophosphonate was coupled to n-amylamine to yield the expected amide 8.

Figure 3:
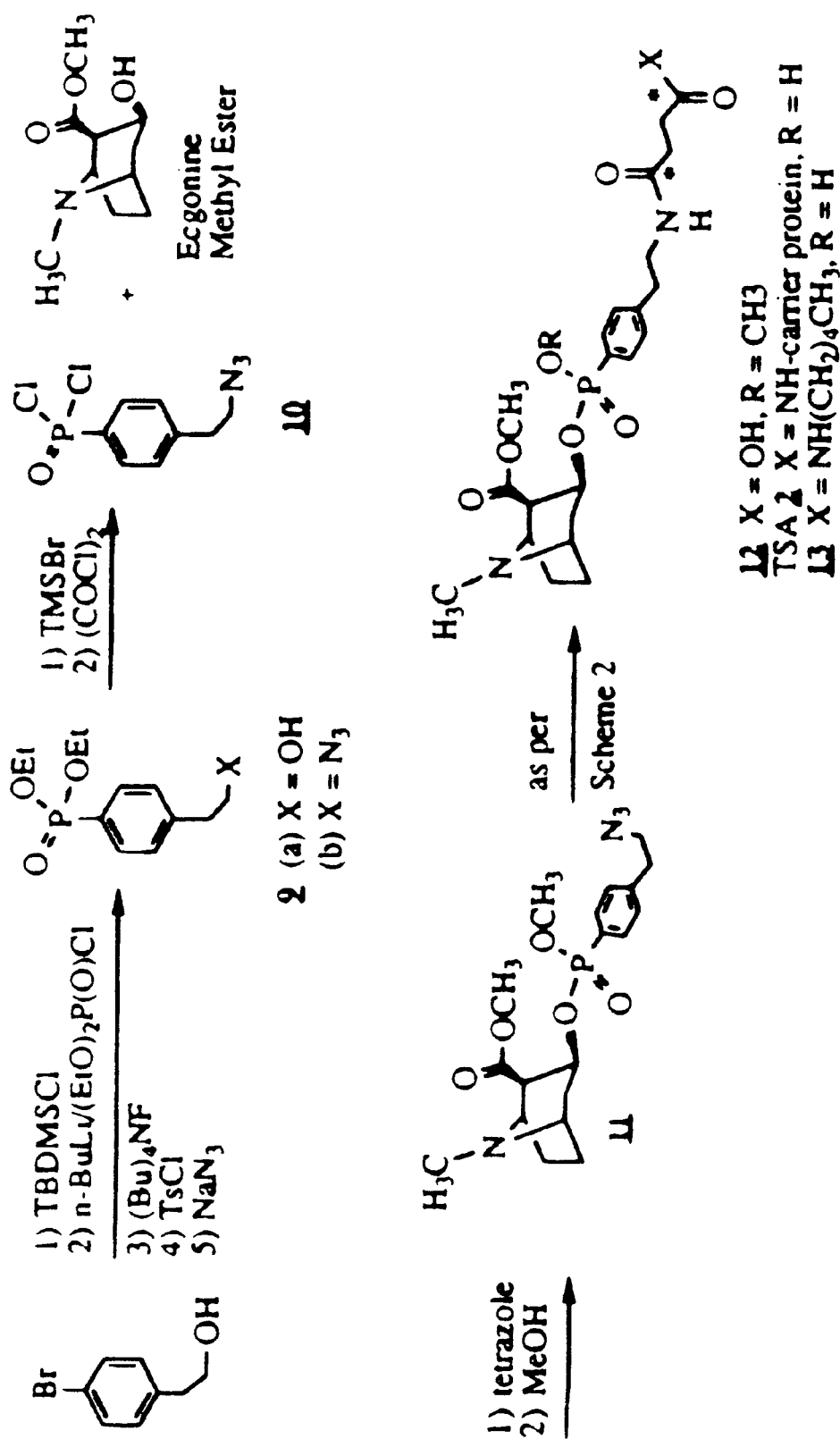
FIG. 3. Synthesis of TSA-2.

Synthesis of TSA-2 required a phenylphosphonic dichloride appropriately substituted at the 4' position for elaboration of a tether (FIG. 3). Silylation of 2-(p-bromophenyl) ethanol followed by transmetallation with n-butyl lithium, quenching with diethyl chlorophosphate and desilylation provided alcohol 9a in 23% yield. The tosylate of 9a was displaced by azide and transesterification with trimethylsilyl bromide, followed by reaction with oxalyl chloride (16), provided the required phenylphosphonic dichloride 10. Using the tetrazole catalysis method described above, chloride 10 was coupled with ecgonine methyl ester and, after the addition of methanol, the mixed diester 11 was obtained in 25% yield. The tether was elaborated from the azide by a sequence of reactions identical to that employed for TSA-1.

Figure 4:
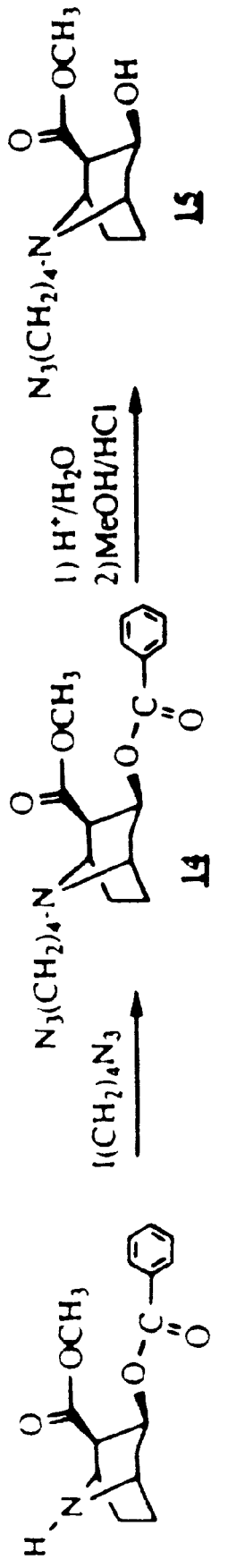
FIG. 4. Synthesis of TSA-3.
Figure 4:
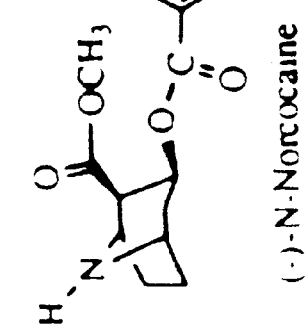
Figure 4:
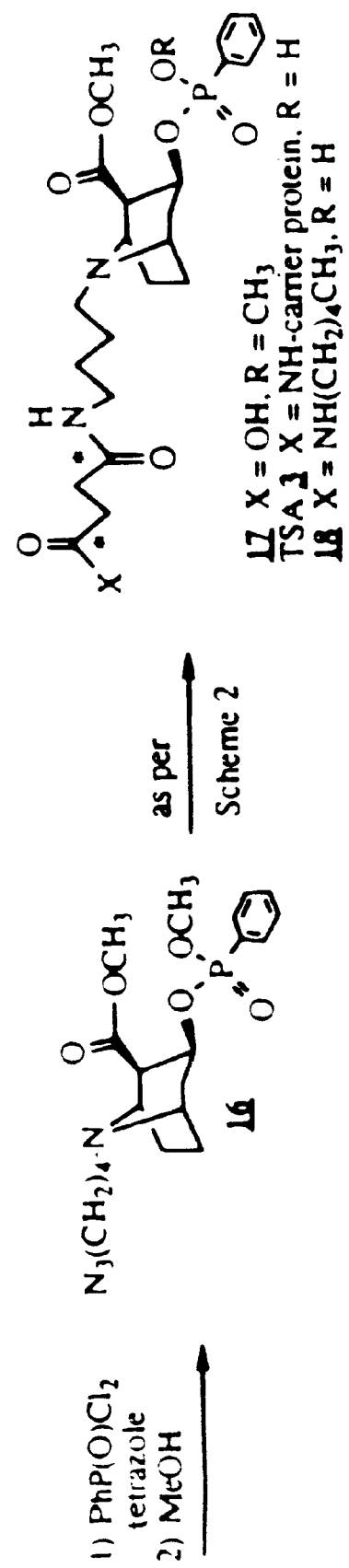
Figure 5:
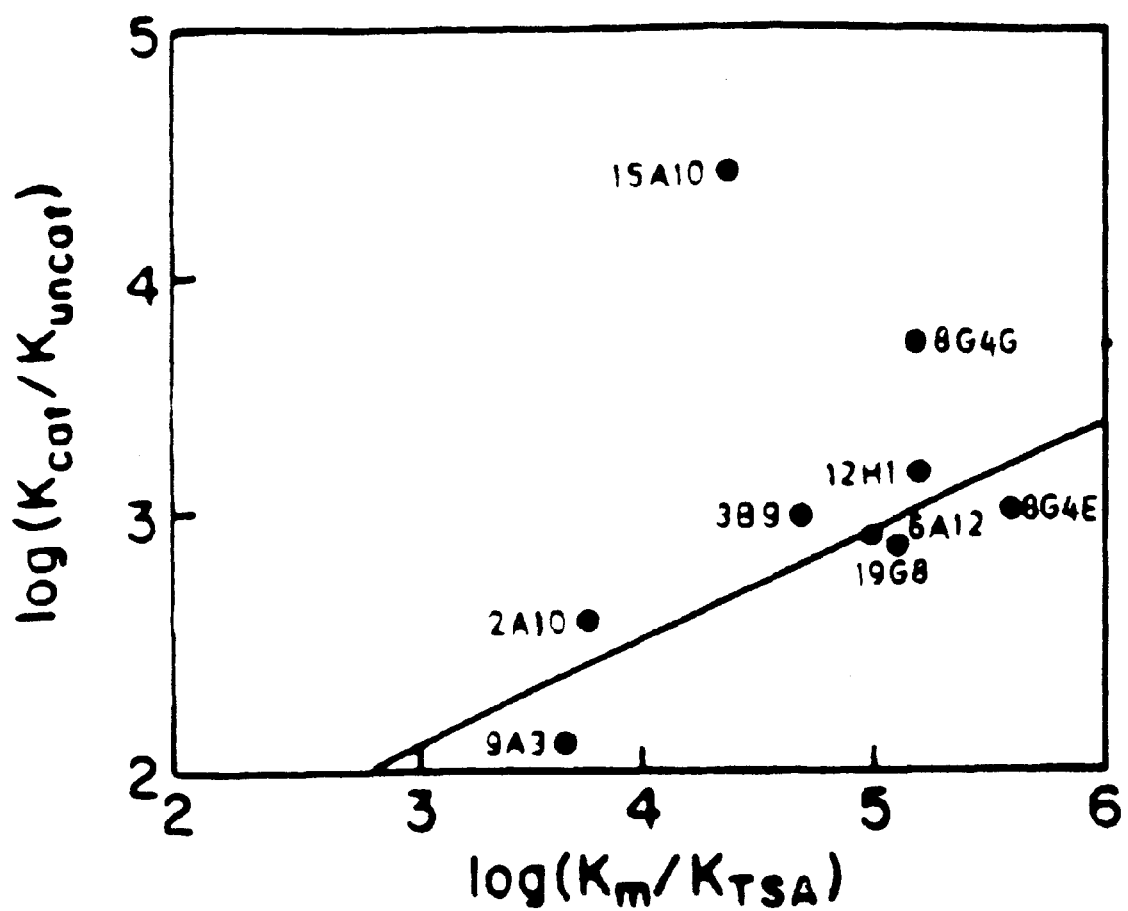
FIG. 5. Plot of log ($K_m/K_{TSA4}$) versus log ($K_{cat}/K_{uncat}$) for catalytic antibodies generated by TSA1, 2, and 3. Data represented in this figure are from Tables 1 and 2. Linear relationship by least squares method; r=0.85 excluding Mab 15A10 and 8G4G.

For the synthesis of TSA-3, (FIG. 4) N-norcocaine was monoalkylated in 75% yield and acid hydrolysis followed by reesterification with acidic methanol provided alcohol 15 in 72% yield. Tetrazole-catalyzed synthesis of mixed phosphonate diester 16 proceeded in 48% yield and the tether was elaborated from the azido moiety as described above.

Generation of Anti-cocaine Catalytic Antibodies

Balb/C mice were immunized with individual analogs conjugated to BSA and high titer antisera were elicited by each antigen. Monoclonal antibodies were prepared by standard protocols (9,17) and hybridomas secreting analog-specific antibodies as determined by an enzyme-linked immunosorbent assay (ELISA) were selected. All IgG anti-analog antibodies were subcloned, propagated in ascites or cell culture flasks and purified by protein A affinity column chromatography. Catalytic antibodies were identified by their capacity to release $^3$H-benzoic acid from $^3$H$_{phenyl}$-cocaine. The radiolabeled benzoic acid was conveniently partitioned from $^3$H-cocaine by extraction of the acidified reaction mixture into organic solvent. Hydrolysis of cocaine with commercially available carboxyl esterase provided a positive control and the production of benzoic acid was confirmed by high performance liquid chromatography. A total of nine catalytic antibodies out of 107 anti-analog antibodies were identified from 9 fusions with TSA 1 yielding 6 out of 50 and TSA 3 yielding 2 out of 49. TSA-2 generated eight anti-analog antibodies of which one was catalytic. Catalytic antibodies were further purified by DEAE anion exchange chromatography and they retained activity. All enzymes were inhibited completely by 50 $\mu$M free TSA 4 (see below) and the Fab portion of each antibody tested retained catalytic activity; the potent inhibitor of serum esterases, eserine (18) at 1 mM, did not inhibit the activity of any catalytic mAb and 150 $\mu$M free TSA 4 did not inhibit the cocaine esterase activity present in serum (results not shown).

Characterization of Catalytic Antibodies

The rate of hydrolysis of $^3$H$_{phenyl}$-cocaine in the presence and absence of each monoclonal antibody as a function of substrate concentration has been determined. Production of radiolabeled benzoic acid at time points corresponding to <5% reaction provided initial rates. A saturation kinetics and obtained a linear Lineweaver-Burk plot for each artificial enzyme has been observed. The first-order rate constants ($k_{cat}$) and Michaelis constants ($K_m$) of the nine catalytic antibodies ranged from 0.011 to 2.3 min$^{-1}$ and from 150 to 3000 $\mu$M, respectively, as shown in Table 1.

TABLE 1

Kinetic parameters for the hydrolysis of $^3$H-cocaine by Mab's.

| Mab | TSA | $K_m$ ($\mu$M) | $k_{cat}$ (min$^{-1}$) | $k_{cat}/k_o$ |
|---|---|---|---|---|
| 3B9 | 1 | 490 | 0.11 | 1100 |
| 6A12 | 1 | 1020 | 0.072 | 880 |
| 2A10 | 1 | 3000 | 0.011 | 420 |
| 9A3 | 1 | 270 | 0.015 | 140 |
| 19G8 | 1 | 900 | 0.091 | 830 |
| 15A10 | 1 | 220 | 2.3 | 23000 |
| 12H1 | 2 | 150 | 0.16 | 1500 |
| 8G4G | 3 | 530 | 0.60 | 5500 |
| 8G4E | 3 | 1200 | 0.12 | 1100 |

Michaelis, constant Km; catalytic rat constant, $k_{cat}$; and spontaneous rate $k_o$. Assays were performed at the pH that optimized $k_{cat}/k_o$: in general pH 7.8; for 6A12, pH 7.4; for 2A10, pH 7.0.

Michaelis constant Km; catalytic rate constant, $k_{cat}$; and spontaneous rate $k_o$. Assays were performed at the pH that optimized $k_{cat}/k_o$: in general pH 7.8; for 6A12, pH 7.4; for 2A10, pH 7.0.

The rate acceleration of the most active catalytic antibody, Mab 15A10, was higher and the Michaelis constant lower then those previously reported (9) for Mab 3B9; this corresponds to almost two orders of magnitude improvement in activity at sub-saturating concentrations of cocaine. It has also been reported previously that Mab 3B9 displayed a rate acceleration commensurate with the ratio of $K_m$ to the $K_i$ for free TSA 4. This ratio approximates the affinity of antibody for ground-state relative to transition-state and in the case of Mab 3B9 suggested that the rate acceleration resulted primarily from transition-state stabilization (19). The inhibition constant ($K_i$) of free TSA 4 for Mab 15A10 to be 0.23 $\mu$M has been determined; the rate acceleration of this catalytic antibody ($k_{cat}/k_{uncat}$=2.3×10$^4$) significantly exceeded $K_m/K_i$ (9.6×10$^2$).

The dissociation constant $K_{TSA}$ for all the catalytic antibodies by competitive inhibition enzyme immunoassay (20) has been determined (CIEIA) as shown in Table 2.

TABLE 2

Competitive Inhibition Enzyme Immunoassay of catalytic Mab's

| Mab (TSA) | $K_4$ ($\mu$M) | $K_8$ ($\mu$M) | $K_{13}$ ($\mu$M) | $K_{18}$ ($\mu$M) |
|---|---|---|---|---|
| 3B9 (1) | 0.01 | 0.02 | 3 | 100 |
| 6A12 (1) | 0.01 | 0.01 | 4 | 90 |
| 2A10 (1) | 0.5 | 3 | 20 | 150 |
| 12H1 (2) | 0.001 | 0.01 | 2 | 60 |
| 9A3 (1) | 0.05 | 0.02 | — | 0.003 |
| 19G8 (1) | 0.008 | 0.001 | — | 0.001 |
| 15A10 (1) | 0.009 | 0.003 | — | 0.0005 |
| 8G4G (3) | 0.003 | 0.001 | — | 0.001 |
| 8G4E (3) | 0.003 | 0.0005 | — | 0.003 |

Dissociation constants for free TSA 4 and TSA-related amides 8, 13, or 18 were determined for each catalytic Mab by CIEIA through competitive inhibition of Mab binding to the TSA (1, 2 or 3 tethered to ovalbumin) that elicited the Mab.

$K_{TSA}$ determined by CIEIA provides a relative measure of $K_i$ and permits assay at very low concentrations of antibody. As shown in FIG. 1, a log-log plot of $k_{cat}/k_{uncat}$ vs $K_m/K_{TSA}$ displayed a linear relationship (r=0.85) for 7 of the 9 catalytic antibodies; since $K_{TSA}$ is proportional to $K_i$, the relationship $k_{cat}/k_{uncat} \cong K_m/K_i$ for Mab 3B9 is likely true for all seven antibodies. Mab 15A10 deviated from this line, as expected since $k_{cat}/k_{uncat}$ exceeded $K_m/K_i$ as described above; Mab 8G4G also apparently deviated as shown. Thus, the rate acceleration for 15A10, and perhaps 8G4G, appears too great to be solely attributed to transition-state stabilization and the participation of chemical catalysis, such as acid-base or nucleophilic catalysis, is likely.

Mab 15A10 was not inhibited by the product of cocaine hydrolysis, ecgonine methyl ester, at a concentration of 1 mM. Benzoic acid did inhibit with a $K_i$ of 250 $\mu$M. However, in humans, benzoic acid plasma levels are markedly suppressed by a rapid and nearly complete conversion to hippuric acid (21). It was found that 1 mM hippuric acid did not inhibit Mab 15A10. Also, there was no inhibition from 1 mM benzoyl ecgonine, a prominent metabolite of cocaine in man (22). Inactivation of Mab 15A10 by repetitive turnover was not observed; after 6 hrs, and >200 turnovers, the $k_{cat}$ remained >95% of baseline. The presence of minimal product inhibition by ecgonine methylester was fortuitous; heterologous immunization (23) with TSA 1, 2, and 3 and the corresponding 1,2-aminoalcohol analogs of cocaine is planned both for its potential to minimize product inhibition and its capacity to increase the yield of active enzymes.

The rationale for varying the tether sites of TSA to carrier protein (BSA) was to expose unique epitopes and elect catalytic antibodies specific to each immunogen. In order to assess binding specificity, the catalytic antibodies were examined by ELISA with TSA 1, 2, and 3 bound to ovalbumin. Unexpectedly, two groups with broad affinities were identified, a "3B9 group" (Mab's 3B9, 6A12, 2A10, 12H1) that bound all three conjugates and a "9A3 group" (Mab's 9A3, 19G8, 15A10, 8G4G, 8G4E) that bound only TSA-1 and 3.

To estimate the affinities for TSA 1, 2, and 3 within these groups relative $K_d$'s of the corresponding amides 8, 13, and 18 by CIEIA has been determined. As shown in Table 2, CIEIA confirmed the ELISA result, identifying the same two broad groups of catalytic antibodies. The 3B9 group displayed the rank order of affinities: 8>13>18. The relative $K_d$ for the amide of the TSA that elicited each antibody ranged from 0.01 μM for Mab 3B9 and 6A12 to 3 μM for Mab 2A10. Mab 12H1 derived from TSA 2 showed a greater affinity for the TSA1-related amide 8 (0.01 uM) then for the TSA2-related amide 13 (2 uM). TSA 1 could have elicited Mab 12H1 and the affinities of Mab's 3B9, 6A12 and 2A10 for 13 are also probably sufficient for TSA 2 to have elicited them. The very low affinities of the 3B9 group for the TSA3-related amide 18 suggest that TSA 3 could not have elicited this group.

The 9A3 group showed a distinctly different pattern with very high affinity for TSA1-related amide 8 and TSA3-related amide 18 but virtually none for TSA2-related amide 13. Apparently, TSA-1 or TSA-3 could have elicited every member of this group; TSA-2 could not have elicited any.

To assess the structural diversity of the catalytic Mab's, pcr-cloning and sequencing the variable regions of the heavy and light chains of each antibody were performed. Primers were generally derived from published consensus sequences (24). The 600–700 bp pcr fragment from each reaction was cloned into pBluescript and independently prepared clones were sequenced in both directions. The deduced primary amino acid structures contained the N-terminal amino acid sequences derived from authentic catalytic antibody samples. Amino acid sequencing also provided primers for pcr-cloning of Mab's 2A10 and 15A10. The complementarity determining regions (CDR's) were aligned for comparison (Table 3), and several discrete families of anti-cocaine catalytic antibodies were identified.

TABLE 3

Deducted Amino acid sequences of catalytic antibodies light chain CDR's (Panel A) and heavy chain CDR's (Panel B).

A.
| Mab | CDR1 | CDR2 | CDR3 |
|---|---|---|---|
| 3B9 | RSSRSLLYRDGKTYLN | LMSTRSS | QHFVDYPFT |
| 6A12 | RSSKSLLYEDGKTYLN | LMSTRAS | QHFEDYPFT |
| 2A10 | RSSKSLLYRDGKTYLN | LMSTRAS | QQFVEYPFT |
| 12H1 | RSSRSLLYRDGKTYLN | LMSTRAS | QHFEDYPFT |
| 9A3 | RSSTGTI-TTSN-YAN | INNNRPP | ALWYSNHWV |
| 19G8 | RSSAGTI-TTSN-YAN | VNNNRPP | ALWYSNHWV |
| 15A10 | RSSTGTI-TSDN-YAN | VNNYRPP | ALWYSNHWV |
| 8G4G | RSSSGTI-TANN-YGS | VSNNRGP | ALWNSNHFV |
| 8G4E | KSSQSLLYSDGKTYLN | LVSKLDS | VQGYTFPLT |

B.
| Mab | CDR1 | CDR2 | CDR3 |
|---|---|---|---|
| 3B9 | SDYAWT | YIR-HIYGTRYNPSLIS | YHYYGS-AY |
| 6A12 | SDYAWT | YIR-HIYGTRYNPSLIS | YHYYGS-AY |
| 2A10 | SDYAWN | YIR-YSGITRYNPSLKS | IHYYG-YGN |
| 12H1 | SDYAWT | YIR-HIYGTRYNPSLIS | YHYYGS-AY |

TABLE 3-continued

Deducted Amino acid sequences of catalytic antibodies light chain CDR's (Panel A) and heavy chain CDR's (Panel B).

| 9A3 | -DYNMY | YIDPSNGGIFYNQKFKG | -G-GGLFAY |
|---|---|---|---|
| 19G8 | -DYNMY | YIDPHNGGIFYNQKFKG | -G-GGLFAY |
| 15A10 | -DYNMY | YIDPSNGDTFYNQKFQG | -G-GGLFAF |
| 8G4G | T-YYIY | GMNPGNGVTYFNEKFKN | - -VGNLFAY |
| 8G4E | -DHWMH | TIDLSDTYTGYNQNFKG | -R-G- -FDY |

TSA 1 yielded two structural families, 3B9-6A12-2A10 and 9A3-19G8-15A10. The light chain CDR homology for parings within the 3B9 family averaged 96%; within the 9A3 family the average was 93%; whereas between these families the average was 14%. The heavy chain CDR homology within the 3B9 family was high with 3B9 and 6A12 identical and 2A10 67% homologous; within the 9A3 family the average heavy chain CDR homology was 88%; but between the 3B9 and 9A3 families the average was 32%. TSA 3 yielded two single-membered families 8G4G and 8G4E. The light chain CDR homology for 8G4 G showed 68% homology to the 9A3 group and<20% homology to the others; 8G4E showed 56% homology with the 3B9 group and ≦20% to all others. The heavy chain CDR homology between 8G4G and 8G4E was 24%; for each to the 9A3 group 48% and <20% to all others. Mab 12H1, derived from TSA-2, showed high homology (96%) to the light chain CDR's of the 3B9-6A12-2A10 group and was identical to the heavy chain CDR's of 3B9 and 6A12.

Synthesis of a Single Chain Fv Fragment

Single chain Fv fragments for catalytic monoclonal antibody 3B9 was prepared via the following construction. Mab 3B9 DNA of $V_H$ and $V_L$ were subcloned by PCR using following primers $V_H$:

TATCCATATGGAGGTGCAGCTGCAG-
GAGTCTGGACCTGAGCTGGTGAAGCC3' and

5'ATGGGGGTGTCGGCATGCCTGCAGAGAC3';

and the following primers $V_L$:

5'CCCCATGGATATTGTGATGACCCAGGAT3' and

5'TAACTGCTCGAGGGATGGTGGGAA3.

DNA of $V_L$ was digested by Nco I and Xho I and introduced into pET20b (Novagen). DNA of $V_H$ was digested by Nde I and SphI, and introduced into pUC18 containing a following linker sequence:

(SphI)-CATCCGGAGGCGGTGGCTCGGGCGGTG-
GCGGCTCGGGTGGCTCTGC-(NcoI).

This plasmid was digested by NdeI and NcoI, and introduced into pET20b containing $V_L$ DNA. Then, this plasmid was digested by Xho I and a following sequence that codes flag sequence was introduced; TCGATTACAAGGACGAC-GATGACAAGC. The resulting scFv is described in FIG. 27.

The resulting plasmid was transformed into BL21(DE3) pLysS. Cells were grown in LB medium at 37° C. At an $OD_{550}$ of 0.6 IPTG was added to a final concentration of 2 mM, and the cells were further grown for 2 hr before harvest. The cells were suspended in 20 of culture volume of binding buffer (5 mM imidazole/0.5M NaCl/20 mM Tris-HCl, pH 7.9)/6M Urea, disrupted by freezing and thawing and removed debris by centrifugation (10000 g×20 min). Supernatant was applied to HistBind Resin Column (Novagen) and eluted with 6M urea/1M imidazole/0.5M NaCl/20 mM Tris-HCl pH 7.9.

Elisa analysis of the resulting single chain Fv fragment demonstrated binding activity. Enzymatic activity was confirmed by the release of the $^3H$ benzoic acid from the $^3H_{phenyl}$-cocaine.

EXPERIMENTAL DISCUSSION

The clinical application of a catalytic antibody against cocaine relies on a kinetic argument since a 100 mg dose of cocaine if antagonized solely by antibody binding would require 25 g of antibody (assuming an antibody MW of 150 kD and 2:1 cocaine:antibody stoichiometry). Active immunization with cocaine tethered to an immunoconjugate would be unlikely to provide more than a few percent of this requirement (25). Polyclonal gamma globulin can be administered in doses of this magnitude but clearly only enzymatic turnover reduces the antibody requirement to a practical magnitude and, most importantly, allows for the burden of repetitive self-administration—the hallmark of addiction.

The failure of decades of effort to identify classical receptor blockers of cocaine, together with the compelling nature of the cocaine problem, justify an exhaustive strategy (26,27). One impediment to this effort is the limited diversity of the antibodies elicited by a given analog. Clearly, antibody diversity is not necessary if, by chance, a single class of antibodies ultimately yields a member with the desired kinetic parameters. However, the capacity of a given antibody to be optimized to specification cannot be predicted due to the scarcity of structural data on catalytic antibodies. The generation of a diverse group of anti-cocaine catalytic antibodies should improve the prospects for successful optimization whether through repetitive large-scale hydridoma preparation or through mutagenesis.

Using the tetrazole catalysis method for phosphonate ester synthesis, three transition-state analogs of cocaine hydrolysis were synthesized. The core phosphonate monoester structure was identical in each and only the tether sites varied. All three elicited catalytic antibodies and a competitive ELISA and CDR sequencing were used to define functional and structural groupings, respectively.

A comparison of the CDR's of the active antibodies delineated four discrete non-overlapping families that were elicited specifically by TSA 1 (3B9-6A12-2A10 and 9A3-19G8-15A10) and TSA 3 (8G4G and 8G4E). TSA 2 yielded one antibody highly homologous to the 3B9-6A12-2A10 family from TSA 1 and without homology to the antibodies derived from TSA 3. These structural families overlapped in part with two broad groups defined by a CIEIA method in which amides 8, 13, and 18 (representing TSA 1, 2 and 3, respectively) inhibited the binding of each catalytic antibody to its eliciting TSA.

One group defined by CIEIA consisted of Mab's 3B9, 6A12, 2A10 and 12H1. This group displayed high affinity for 8, moderate affinity for 13 and very low affinity for 18. All of the highly homologous members of this group could have been elicited by TSA 1; the one antibody derived from TSA 2, Mab 12H1, bound TSA1-related amide 8 with even greater affinity than TSA2-related amide 13. Nonetheless it is possible that most if not all of the group could have been elicited by TSA 2 since the range of affinities for 13 in this group overlapped with the range of affinities for the amides of the TSA's that elicited each antibody. In contrast, the very low affinity of 18 for every member of this group suggests that TSA 3 could not yield any member of the group. A strategy to obtain catalytic antibodies against cocaine based only on a TSA tethered at the tropane nitrogen (28) would fail to identify this group of antibodies.

The second group defined by CIEIA consisted of five catalytic antibodies from three structural families: 9A3-19G8-15A10 derived from TSA 1; 8G4G and 8G4E from TSA 3. These five antibodies displayed equally high affinity for amides 8 and 18 and in principle either TSA 1 or 3 could have elicited every catalytic antibody in this group. That TSA 1 and 3 did not yield members of a common structural family may reflect the inadequacy of a sample size averaging 3 fusions per analog. None of the five antibodies could have been obtained with TSA 2 and thus three of the four structural families would not have been identified with this conjugate.

TSA 1 elicited the most active catalytic antibody, Mab 15A10. Moreover, based on the high affinity of amide 8 for all nine catalytic antibodies, TSA 1 could plausibly have elicited every antibody described. This result was unexpected but not a definitive endorsement of TSA 1 as the preferred analog. With more aggressive screening, TSA 2 or 3 may ultimately yield a more active antibody not recognized by TSA 1.

Clearly, the failure of a TSA (e.g. TSA 2) to bind to a catalytic antibody (e.g. 15A10) derived from an alternate immunogenic conjugate confirms that the location of the tether limits the catalytic antibodies produced and supports varying the site of attachment to carrier protein. Exhaustive screening of hybridomas from TSA 1, 2 and 3 and detailed structural studies of the catalytic antibodies elicited may clarify the rules for analog construction. The pursuit of high activity anti-cocaine catalytic antibodies provides a compelling justification for this effort.

The results of this work indicate that these antibodies, particularly, 15A10, are the first artificial enzymes to surpass all known natural enzymes in degrading cocaine.

REFERENCES

1. Goeders, N. E.; Smith J. E. *Science* 1983, 221, 773; (b) Kubar, M. J.; Zargin, M. A. *J. Neurochem.* 1975, 31, 251; (c) Horn, A. S. *Prog. Neurobiol.* 1990, 34, 387; (d) Ritz, M. C.; Lamb, R. J.; Goldberg, S. R.; Kuhar, M. J. *Science* 1987, 237, 1219; (e) Shimada, S.; et al., *Science,* 1991, 254, 576; (f) Kitty. J. E.; Lorang, D.; Amara, S. G. *Science,* 1991, 254, 578.
2. Fischman, M. W. *J. Clin. Psychiatry.* 1988, 49, 7.
3. Bonese, K. F.; Wainer, B. H.; Fitch, F. W.; Rothberg R. M.; Schuster, C. R. *Nature,* 1974, 252, 708.
4. Tramontano, A.; Janda, K. D.; Lerner, R. A. *Science,* 1986, 234, 1566; (b) Pollack, S. J.; Jacobs, J. W.; Schultz, P. G. *Science,* 1986, 234, 1570; (c) Lerner, R. A.; Benkovic, S. J.; Schultz, P. G. *Nature,* 1991, 252, 659.
5. Misra, A. L.; Nayak, P. K.; Bloch, R.; Mule, S. J. *Pharm. Pharmacol.* 1975, 27, 784.
6. Gatley, S. J. *Biochem. Pharmacol.* 1991. 41, 1249.
7. Janda, K. D.; Ashley, J. A.; Jones, T. M.; McLeod, D. A.; Schloeder, D. M.; Weinhouse, M. I.; Lerner, R. A.;

Gibbs, R. A.; Benkovic, P. A.; Hilhorst, R.; Benkovic, S. J. *J. Am. Chem. Soc.* 1991, 113, 291; (b) Iverson, B. I.; Lerner, R. A. *Science,* 1989, 243, 1184; (c) Wade, W. S.; Ashley, J. A.; Jahangiri, G. K.; McElhaney, G.; Janda, K. D.; Lerner, R. A. *J. Am. Chem. Soc.,* 1993, 115,4906; (d) Roberts, V. A.; Stewart J.; Benkovic S. J.; Getzoff, E. D. *J. Mol. Biol.* 1994, 235, 1098; (e) Baldwin, E.; Schultz, P. G. *Science,* 19, 245, 1104; (f) Jacobsen, J. R.; Prudent, J. R.; Kochersperger, L.; Yonkovich, S.; Schultz, P. G. *Science,* 1992, 256, 365; (g) Miyashita, H.; Karaki, Y.; Iruchi, M.; Fujii, I. *Proc. Natl. Acad. Sci.,* 1993, 90, 5337; (h) Martin, M. T.; Napper, A. D.; Schultz, P. G.; Ress, A. R. *Biochemistry,* 1991, 30, 9757; (i) Zhou, G. W.; Guo, J.; Huang, W.; Fletterick, R. J.; Scanlan, T. S. *Science,* 1994, 265, 1059; (j) Nakatani, T.; Hiratake, J.; Shinzaki, A.; Umeshita, R.; Suzuki, T.; Nishioka, T.; Nakajima, H.; Oda, J. *Tetrahedron Letters,* 1993, 34, 4945; (k) Janda, K. D.; Schloeder, D.; Benkovic, S. J.; Lerner, R. A. *Science,* 1988, 241, 1188; (1) Tramontano, A.; Janda, K D.; Lerner, R. A. *Proc. Natl. Acad. Sci.,* 1986, 83, 6736; (m) Janda, K. D.; Benkovic, S. J.; Lerner, R. A. *Science,* 1989, 244, 437; (n) Suga, H.; Ersoy, O.; Tsumuraya, T.; Lee, J.; Sinskey, A. J.; Masamune, S. *J. Am. Chem. Soc.,* 1994, 116, 487.

8. Benkovic, S. J.; Adams, J. A.; Borders, C. C. Jr.; Janda, K. D.; Lerner, R. A. *Science,* 1990, 250, 1135; (b) Tramontano, A.; Ammann, A. A.; Lerner, R. A. *J. Am. Chem. Soc.* 1988, 110, 2282.

9. Landry, D. W.; Zhao, K.; Yang, G. X.-Q.; Glickman, M.; Georgiadis, T. M. *Science,* 1993, 259, 1899.

10. Miyashita, H.; Hara, T.; Tanimura, R.; Tanaka, F.; Kikuchi, M.; Fujii, I. *Proc. Natl. Acad. Sci. USA.* 1994, 91, 6045.

11. Janda, K. D.; Weinhouse, M. I.; Danon, T.; Pacelli, K. A.; Schloeder, D. M. *J. Am. Chem. Soc.* 1991, 113, 5427.

12. Janda, K. D.; Benkovic, S. J.; McLeod, D. A.; Schloeder, D. M.; Lerner, R. A. *Tetrahedron* 1991, 47, 2503.

13. Fowler, J. J. et al. *Synapse* 1989, 4, 371.

14. Zhao, K.; Landry, D. W. *Tetrahedron* 1993, 49, 363.

15. McKenna, C. E.; Higa, M. T.; Cheung, N. H.; McKenna, M.-C. *Tetrahedron. Lett.* 1977, 155.

16. Bhongle, N. N.; Notter, R. H.; Turcotte, J. G. *Synth. Commun.* 1987, 1071.

17. Goding, J. W. *Monoclonal Antibodies Principles and Practice;* 1986. Academic Press:London 18. Stewart, D. J.; Inaba, T.; Tang, B.; Kalow, M. *Life Sci.* 1977, 20, 1557.

19. Benkovic, S. J.; Napper, A. D.; Lerner, R. A. *Proc. Natl. Acad. Sci. U.S.A.* 1988, 85, 5355.

20. Rath, S.; Stanley, C. M.; Steward, M. W. *J. Immuno. Methods* 1988, 106, 245. (b) Fujii, I.; Tanaka, F.;Miyashita, H.; Tanimura, R.; Kinoshita, K. *J. Am. Chem. Soc.* 1995 117, 6199.

21. Kubota, K.; Horai, Y.; Kushida, K.; Ishizaki, T. *J. Chromatography* 1988 425, 67. (b) Kubota, K.; Ishizaki, T. *J. Clin. Pharmacol* 1991, 41, 363.

22. Ambre, J. *J. Anal. Toxicol.* 1985, 9, 241.

23. Suga H.; Ersoy, O.; Williams, S. F.; Tsumuraya, T.; Margolies, M. N.; Sinskey, A. J.; Masamune, S. *J. Am. Chem. Soc.* 1994, 116, 6025.

24. Kabat, E. A.; Wu, T. T.; Reid-Miller, M.; Perry, H. M.; and Gottsman, K. S. (*Bethesda, Md.: U.S. Public Health Service*) (1987).

25. Rocio, M.; Carrera, A.; Ashley, J. A.; Parsons, L. H.; Wirsching, P.; Koob, G. F.; Janda, K. D. *Nature* 1995, 378, 727.

26. Tawfik, D. S.; Green, B. S.; Chap, R.; Sela, M.; Eshhar, Z. *Proc. Natl. Acad. Sci. USA* 1993, 90, 373.

27. Stewart, J. D.; Roberts, V. A.; Thomas, N. R.; Getzoff, E. D.; Benkovic, S. J. *Biochem.* 1994, 33, 1994. (b) Baldwin, E.; Schultz, P. G. *Science,* 1989, 245, 1104. (c) Benkovic, C. J. *Annu. Rev. Biochem.* 1992, 61, 29. (d) Jackson, D. Y.; Prudent, J. R.; Baldwin, E. P.; Schultz, P. G. *Proc. Natl. Acad. Sci. USA* 1991, 88, 58.

28. Chandrakumar, N. S.; Carron, C. P.; Meyer, D. M.; Beardsley, P. M.; Nash, S. A.; Tam, L. L.; Rafferty, M. *Bioorgenic & Medicinal Chem. Letters,* 1993, 3, 309.

29. Still, W. C.; Kahn, J.; Mitra, A. *J. Org. Chem.* 1978, 43, 2923.

30. Matsudaira, P. *J. Biol. Chem.* 1987, 262, 10035.

31. Fernandez, J.; Andrews, L.; Mische, S. *Anal. Biochem.* 1994, 218, 112.

32. Chirgwin, J. M.; Przybyla, A. E.; MacDonald, R. J.; Rutter, W. J. *Biochemistry* 1979, 18, 5294.

---

What is claimed is:

1. A catalytic antibody capable of degrading cocaine comprising a light chain wherein the amino acid sequence of complementarity determining region 1 is RSSXGTITXXN-YAN (Seq ID No: 73), the amino acid sequence of complementarity determining region 2 is XNNYRPP (Seq ID No: 74) and the amino acid sequence of complementarity determining region 3 is ALWYSNHWV (Seq ID No: 75) and a heavy chain wherein the amino acid sequence of complementarity determining region 1 is DYNMY (Seq ID No: 76), the amino acid sequence of complementarity determining region 2 is YIDPXNGXXFYNQKFXG (Seq ID No. 78) and the amino acid sequence of complementarity determining region 3 is GGGLFAX (Seq ID No: 78).

2. The catalytic antibody of the claim 1, comprising a light chain wherein the amino acid sequence of complementarity determining region 1 is RSSTGTITSDNYAN (Seq ID No. 37), the amino acid sequence complementarity determining region 2 is VNNYRPP (Seq ID No. 38) and the amino acid sequence complementarity determining region 3 is ALWYSNHWV (Seq ID No. 39) and a heavy chain wherein the amino acid sequence of complementarity determining region 1 is DYNMY (Seq ID No: 64), the amino acid sequence of complementarity determining region 2 is YIDPSNGDTFYNQKFQG (Seq ID No: 65) and the amino acid sequence of complementarity determining region 3 is GGGLFAF (Seq ID No: 66).

3. The catalytic antibody of claim 2, wherein the light chain comprises the amino acid sequence as set forth in Seq ID No:3 and the heavy chain comprises the amino acid sequence as set forth in Seq ID No: 16.

4. The catalytic antibody of claim 1, comprising a light chain wherein the amino acid sequence of complementarity determining region 1 is RSSAGTITTSNYAN (Seq ID No. 34), the amino acid sequence of complementarity determining region 2 is VNNNRPP (Seq ID No. 35) and the amino acid sequence of complementarity determining region 3 is ALWYSNHWV (Seq ID No. 36) and a heavy chain wherein the amino acid sequence of complementarity determining region 1 is DYNMY (Seq ID No: 61), the amino acid sequence of complementarity determining region 2 is YIDPHNGGIFYNQKFKG (Seq ID No. 63) and the amino acid sequence of complementarity determining region 3 is GGGLFAY (Seq ID No: 63).

5. The catalytic antibody of claim 4, wherein the light chain comprises the amino acid sequence as set forth in Seq ID No:2 and the heavy chain comprises the amino acid sequence as set forth in Seq ID No: 15.

6. The catalytic antibody of claim 1, comprising a light chain wherein the amino acid sequence of complementarity determining region 1 is RSSTGTITTSNYAN (Seq ID No. 31), the amino acid sequence of complementarity determining region 2 is INNNRPP (Seq ID No. 32) and the amino acid sequence of complementarity determining region 3 is ALWYSNHWV (Seq ID No. 33) and a heavy chain wherein the amino acid sequence of the of complementarity determining region 1 is DYNMY (Seq ID No: 58), the amino acid sequence of complementarity determining region 2 is YIDPSNGGIFYNQKFKG (Seq ID No: 59) and the amino acid sequence of complementarity determining region 3 is GGGLFAY (Seq ID No: 60).

7. The catalytic antibody of claim 6, wherein the light chain comprises the amino acid sequence as set forth in Seq ID No:1 and the heavy chain comprises the amino acid sequence as set forth in Seq ID No: 14.

8. A catalytic antibody capable of degrading cocaine comprising a light chain wherein the amino acid sequence of complementarity determining region 1 is RSSSGTITAN-NYGS (Seq ID No: 40), the amino acid sequence of complementarity determining region 2 is VSNNRGP (Seq ID No: 41) and the amino acid sequence of complementarity determining region 3 is ALWNSNHFV (Seq ID No: 42) and a heavy chain wherein the amino acid sequence of complementarity determining region 1 is TYYIY (Seq ID No: 67), the amino acid sequence of complementarity determining region 2 is GMNPGNGVTYFNEKFKN (Seq ID No: 68) and the amino acid sequence of complementarity determining region 3 is VGNLFAY (Seq ID No: 69).

9. The catalytic antibody of claim 8, wherein the light chain comprises the amino acid sequence as set forth in Seq ID No:4 and the heavy chain comprises the amino acid sequence as set forth in Seq ID No: 18.

10. A catalytic antibody capable of degrading cocaine comprising a light chain wherein the amino acid sequence of Complementarity determining region 1 is RSSXS-LLYXDGKTYLN (Seq ID No: 79), the amino acid sequence of Complementarity determining region 2 is LMSTRXS (Seq ID No: 80) and the amino acid sequence of Complementarity determining region 3 is QXFXXYPFT (Seq ID No: 81) and a heavy chain wherein the amino acid sequence of complementarity-determining region 1 is SDYAWX (Seq ID No: 82), the amino acid sequence of Complementarity determining region 2 is YIRXXXXTRYNPSLXS (Seq ID No: 83) and the amino acid sequence of Complementarity determining region 3 is XHYYGXXX (Seq ID No: 84) with the proviso that the catalytic antibody is not the catalytic antibody designated "3B9" or "6A12".

11. The catalytic antibody of claim 10, comprising a light chain wherein the amino acid sequence of Complementarity determining region 1 is RSSKSLLYEDGKTYLN (Seq ID No. 25), the amino acid sequence of complementarity determining region 2 is LMSTRAS (Seq ID No. 26) and the amino acid sequence of Complementarity determining region 3 is QQFVEYPFT (Seq ID No. 27) and a heavy chain wherein the amino acid sequence of complementarity determining region 1 is SDYAWN (Seq ID No: 52), the amino acid sequence of complementarity determining region 2 is YIRYSGITRYNPSLKS (Seq ID No: 53) and the amino acid sequence of complementarity determining region 3 is IHYYGYGN (Seq ID No: 54).

12. The catalytic antibody of claim 11, wherein the light chain comprises the amino acid sequence as set forth in Seq ID No:8 and the heavy chain comprises the amino acid sequence as set forth in Seq ID No: 13.

13. A catalytic antibody capable of degrading cocaine comprising a light chain wherein the amino acid sequence of Complementarity determining region 1 is KSSQSLLYS-DGKTYLN (Seq ID No: 43), the amino acid sequence of Complementarity determining region 2 is LVSKLDS (Seq ID No: 44) and the amino acid sequence of Complementarity determining region 3 is VQGYTFPLT (Seq ID No: 45) and a heavy chain wherein the amino acid sequence of Complementarity determining region 1 is DHWMH (Seq ID No: 72), the amino acid sequence of complementarity determining region 2 is TIDLSDTYTGYNQNFKG (Seq ID No: 71) and the amino acid sequence of complementarity determining region 3 is RGFDY (Seq ID No: 72).

14. The catalytic antibody of claim 13, wherein the light chain comprises the amino acid sequence as set forth in Seq ID No:9 and the heavy chain comprises the amino acid sequence as set forth in Seq ID No: 17.

* * * * *

SEQUENCE LISTING (1) GENERAL INFORMATION:

(iii) NUMBER OF SEQUENCES: 108

(2) INFORMATION FOR SEQ ID NO:1:

(i) SEQUENCE CHARACTERISTICS:
      (A) LENGTH: 109 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ala Val Val Thr Gln Glu Ser Ala Leu Thr Thr Trp Pro Gly Glu Thr
 1               5                  10                  15
```

Val Thr Leu Thr Cys Arg Ser Ser Thr Gly Thr Ile Thr Thr Ser Asn
            20                  25                  30

Tyr Ala Asn Trp Val Gln Glu Lys Pro Asp His Leu Phe Ser Gly Leu
            35                  40                  45

Ile Gly Ile Asn Asn Asn Arg Pro Pro Gly Val Pro Ala Arg Phe Ser
            50                  55                  60

Gly Ser Leu Ile Gly Asp Lys Ala Val Leu Thr Ile Thr Gly Ala Gln
65                  70                  75                  80

Thr Glu Asp Glu Ala Ile Tyr Phe Cys Ala Leu Trp Tyr Ser Asn His
            85                  90                  95

Trp Val Phe Gly Gly Gly Thr Lys Leu Thr Val Leu Gly
            100                 105

(2) INFORMATION FOR SEQ ID NO:2:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Ala Val Val Thr Gln Glu Ser Ala Leu Thr Thr Arg Pro Gly Glu Thr
1               5                   10                  15

Val Thr Leu Thr Cys Arg Ser Ser Ala Gly Thr Ile Thr Thr Ser Asn
            20                  25                  30

Tyr Ala Asn Trp Val Gln Glu Lys Pro Asp His Leu Phe Ser Gly Leu
            35                  40                  45

Ile Gly Val Asn Asn Asn Arg Pro Pro Gly Val Pro Ala Arg Phe Ser
            50                  55                  60

Gly Ser Leu Ile Gly Asp Thr Ala Ala Leu Thr Ile Thr Gly Ala Gln
65                  70                  75                  80

Thr Glu Asp Glu Ala Ile Tyr Phe Cys Ala Leu Trp Tyr Ser Asn His
            85                  90                  95

Trp Val Phe Gly Gly Gly Thr Lys Leu Thr Val Leu Gly
            100                 105

(2) INFORMATION FOR SEQ ID NO:3:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ala Val Val Thr Gln Glu Ser Ala Leu Thr Thr Ser Pro Gly Glu Thr
1               5                   10                  15

Val Thr Leu Thr Cys Arg Ser Ser Thr Gly Thr Ile Thr Ser Asp Asn
            20                  25                  30

Tyr Ala Asn Trp Val Gln Glu Lys Pro Asp His Leu Phe Ser Gly Leu
            35                  40                  45

Ile Gly Val Asn Asn Tyr Arg Pro Pro Gly Val Pro Ala Arg Phe Ser
            50                  55                  60

Gly Ser Leu Thr Gly Asp Lys Ala Val Leu Thr Ile Thr Gly Ala Gln
65                  70                  75                  80

```
Thr Glu Asp Glu Ala Ile Tyr Phe Cys Ala Leu Trp Tyr Ser Asn His
            85                  90                  95
Trp Val Phe Gly Gly Gly Thr Lys Leu Thr Val Leu Gly
            100                 105
```

(2) INFORMATION FOR SEQ ID NO:4:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Ala Val Val Thr Gln Glu Ser Ala Leu Thr Arg Ala Pro Gly Glu Thr
1               5                   10                  15
Val Thr Leu Thr Cys Arg Ser Ser Gly Thr Ile Thr Ala Asn Asn
                20                  25                  30
Tyr Gly Ser Trp Val Gln Glu Lys Pro Asp His Leu Phe Thr Gly Leu
            35                  40                  45
Ile Gly Val Ser Asn Asn Arg Gly Pro Gly Val Pro Ala Arg Phe Ser
50                  55                  60
Gly Ser Leu Ile Gly Asp Lys Ala Val Leu Thr Ile Thr Gly Gly Gln
65                  70                  75                  80
Thr Glu Asp Glu Ala Ile Tyr Phe Cys Ala Leu Trp Asn Ser Asn His
            85                  90                  95
Phe Val Phe Gly Gly Gly Thr Lys Leu Thr Val Leu Gly
            100                 105
```

(2) INFORMATION FOR SEQ ID NO:5:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Asp Ile Val Met Thr Gln Asp Glu Leu Ser Asn Pro Val Thr Ser Gly
1               5                   10                  15
Glu Ser Val Ser Ile Ser Cys Arg Ser Ser Arg Ser Leu Leu Tyr Arg
                20                  25                  30
Asp Gly Lys Thr Tyr Leu Asn Trp Phe Leu Gln Arg Pro Gly Arg Ser
            35                  40                  45
Pro Gln Leu Leu Ile Tyr Leu Met Ser Thr Arg Ser Ser Gly Val Ser
50                  55                  60
Asp Arg Phe Ser Gly Ser Gly Ser Gly Thr Asp Phe Thr Leu Glu Ile
65                  70                  75                  80
Ser Arg Val Lys Ala Glu Asp Val Gly Val Tyr Tyr Cys Gln His Phe
            85                  90                  95
Val Asp Tyr Pro Phe Thr Phe Gly Ser Gly Thr Lys Leu Glu Ile Lys
            100                 105                 110
Arg
```

(2) INFORMATION FOR SEQ ID NO:6:

(i) SEQUENCE CHARACTERISTICS:
    (A) LENGTH: 113 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Asp Met Val Met Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Arg
            20                  25                  30

Asp Gly Lys Thr Tyr Leu Asn Trp Phe Leu Gln Arg Pro Gly Arg Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln His Phe
                85                  90                  95

Glu Asp Tyr Pro Phe Thr Phe Gly Ser Gly Thr Lys Leu Glu Ile Lys
                100                 105                 110

Arg
```

(2) INFORMATION FOR SEQ ID NO:7:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Asp Met Val Met Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Arg
            20                  25                  30

Asp Gly Lys Thr Tyr Leu Asn Trp Phe Leu Gln Arg Pro Gly Arg Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln His Phe
                85                  90                  95

Val Asp Tyr Pro Phe Thr Phe Gly Ser Gly Thr Lys Leu Glu Ile Lys Arg
                100                 105                 110

Arg
```

(2) INFORMATION FOR SEQ ID NO:8:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Glu
            20                  25                  30

Asp Gly Lys Thr Tyr Leu Asn Trp Phe Leu Gln Arg Pro Gly Gln Ser
        35                  40                  45

Pro His Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Ala Tyr Tyr Cys Gln Gln Phe
                85                  90                  95

Val Glu Tyr Pro Phe Thr Phe Gly Ser Gly Thr Lys Leu Glu Ile Arg
            100                 105                 110

Arg (2) INFORMATION FOR SEQ ID NO:9:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Glu Leu Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Phe Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Lys Asp Phe Thr Leu Lys Glu
65                  70                  75                  80

Ile Ser Arg Val Glu Ala Glu Asp Leu Gly Leu Tyr Tyr Cys Val Gln
                85                  90                  95

Gly Tyr Thr Phe Pro Leu Thr Phe Gly Ala Gly Thr Lys Leu Glu Leu
            100                 105                 110

Lys Arg (2) INFORMATION FOR SEQ ID NO:10:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
            20                  25                  30

```
Tyr Ala Trp Thr Trp Ile Arg Gln Phe Pro Gly Asn Lys Leu Glu Trp
            35                  40                  45

Met Gly Tyr Ile Arg His Ile Tyr Gly Thr Arg Tyr Asn Pro Ser Leu
 50                      55                  60

Ile Ser Arg Ile Ser Ile Thr Arg Asp Thr Ser Lys Asn Gln Phe Phe
 65                  70                  75                  80

Leu Gln Leu Asp Ser Val Thr Ala Glu Asp Thr Ala Thr Tyr Tyr Cys
                85                  90                  95

Val Arg Tyr His Tyr Tyr Gly Ser Ala Tyr Trp Gly Gln Gly Thr Leu
            100                 105                 110

Val Thr Val Ser Ala
            115

(2) INFORMATION FOR SEQ ID NO:11:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Asp Val Gln Leu Gln Glu Ser Gly Pro Gly Leu Val Lys Pro Ser Gln
 1               5                  10                  15

Ser Leu Ser Leu Thr Cys Thr Val Thr Gly Asn Ser Ile Thr Ser Asp
                20                  25                  30

Tyr Ala Trp Thr Trp Ile Arg Gln Phe Pro Gly Asn Lys Leu Glu Trp
            35                  40                  45

Met Gly Tyr Ile Arg His Ile Tyr Gly Thr Arg Tyr Asn Pro Ser Leu
 50                      55                  60

Ile Ser Arg Ile Ser Ile Thr Arg Asp Thr Ser Lys Asn Gln Phe Phe
 65                  70                  75                  80

Leu Gln Leu Asp Ser Val Thr Ala Glu Asp Thr Ala Thr Tyr Tyr Cys
                85                  90                  95

Val Arg Tyr His Tyr Tyr Gly Ser Ala Tyr Trp Gly Gln Gly Thr Leu
            100                 105                 110

Val Thr Val Ser Ala
            115

(2) INFORMATION FOR SEQ ID NO:12:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Asp Val Gln Leu Gln Glu Ser Gly Pro Gly Leu Val Lys Pro Ser Gln
 1               5                  10                  15

Ser Leu Ser Leu Thr Cys Thr Val Thr Gly Asn Ser Ile Thr Ser Asp
                20                  25                  30

Tyr Ala Trp Thr Trp Ile Arg Lys Phe Pro Gly Asn Lys Leu Glu Trp
            35                  40                  45

Leu Gly Tyr Ile Arg His Ile Tyr Gly Thr Arg Tyr Asn Pro Ser Leu
 50                      55                  60
```

```
Ile Ser Arg Ile Ser Ile Thr Arg Asp Thr Ser Lys Asn Gln Phe Phe
 65                  70                  75                  80

Leu Gln Leu Asp Ser Val Thr Ala Glu Asp Thr Ala Thr Tyr Tyr Cys
                 85                  90                  95

Val Arg Tyr His Tyr Tyr Gly Ser Ala Tyr Trp Gly Gln Gly Thr Leu
                100                 105                 110

Val Thr Val Ser Ala
            115
```

(2) INFORMATION FOR SEQ ID NO:13:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Asp Val Gln Leu Gln Glu Ser Gly Pro Glu Leu Val Lys Pro Ser Gln
 1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Arg Leu Glu Trp
                 35                  40                  45

Met Gly Tyr Ile Arg Tyr Ser Gly Ile Thr Arg Tyr Asn Pro Ser Leu
                 50                  55                  60

Lys Ser Arg Ile Ser Ile Thr Arg Asp Thr Ser Lys Asn Lys Phe Phe
 65                  70                  75                  80

Leu Gln Leu Asn Ser Val Thr Thr Glu Asp Thr Ala Thr Tyr Tyr Cys
                 85                  90                  95

Val Arg Ile His Tyr Tyr Gly Tyr Gly Asn Trp Gly Gln Gly Thr Thr
                100                 105                 110

Leu Thr Gly Leu Pro
            115
```

(2) INFORMATION FOR SEQ ID NO:14:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Asp Val Gln Leu Gln Glu Ser Gly Pro Glu Leu Val Lys Pro Gly Ala
 1               5                  10                  15

Ser Val Lys Leu Ser Cys Lys Ala Ser Gly Tyr Pro Phe Thr Asp Tyr
                 20                  25                  30

Asn Met Tyr Trp Val Lys Gln Ser His Gly Lys Ser Leu Glu Trp Ile
                 35                  40                  45

Gly Tyr Ile Asp Pro Ser Asn Gly Gly Ile Phe Tyr Asn Gln Lys Phe
                 50                  55                  60

Lys Gly Arg Ala Thr Leu Thr Val Asp Lys Ser Ser Asn Thr Ala Phe
 65                  70                  75                  80

Met His Leu Asn Ser Leu Thr Ser Glu Asp Ser Ala Val Tyr Tyr Cys
                 85                  90                  95
```

Ala Arg Gly Gly Gly Leu Phe Ala Tyr Trp Gly Gln Gly Thr Leu Val
            100                 105                 110

Thr Val Ser Glu
        115

(2) INFORMATION FOR SEQ ID NO:15:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Glu Ile His Leu Gln Glu Ser Gly Glu Leu Val Lys Pro Gly Ala Ser
1               5                   10                  15

Val Lys Leu Ser Cys Lys Ala Ser Gly Tyr Ser Phe Thr Ser Asp Tyr
            20                  25                  30

Asn Met Tyr Trp Val Lys Gln Ser His Gly Lys Ser Leu Glu Trp Ile
            35                  40                  45

Gly Tyr Ile Asp Pro His Asn Gly Gly Ile Phe Tyr Asn Gln Lys Phe
    50                  55                  60

Lys Gly Arg Ala Thr Leu Thr Val Asp Lys Ser Ser Asn Thr Ala Phe
65                  70                  75                  80

Met His Leu Asn Val Leu Thr Ser Glu Asp Ser Ala Val Tyr Tyr Cys
                85                  90                  95

Ala Arg Gly Gly Gly Leu Phe Ala Tyr Trp Gly Arg Gly Thr Leu Val
            100                 105                 110

Thr Val Ser Ala
        115

(2) INFORMATION FOR SEQ ID NO:16:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Glu Val Gln Leu Gln Glu Ser Gly Pro Glu Leu Val Lys Pro Gly Ala
1               5                   10                  15

Ser Val Lys Val Ser Cys Lys Ala Ser Gly Tyr Ser Phe Asp Tyr Asn
            20                  25                  30

Met Tyr Trp Val Lys Gln Asn His Gly Glu Ser Leu Glu Trp Ile Ala
            35                  40                  45

Tyr Ile Asp Pro Ser Asn Gly Asp Thr Arg Tyr Asn Gln Lys Phe Gln
    50                  55                  60

Gly Lys Ala Thr Val Thr Leu Asp Lys Ser Ser Ser Thr Ala Phe Met
65                  70                  75                  80

His Leu Asn Ser Leu Thr Ser Glu Asp Ser Ala Val Tyr Tyr Cys Ala
                85                  90                  95

Arg Gly Gly Gly Leu Phe Ala Phe Trp Gly Gln Gly Thr Leu Val Thr
            100                 105                 110

Val Ser Ala
    115

(2) INFORMATION FOR SEQ ID NO:17:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Val Gln Leu Leu Glu Ser Gly Ala Glu Leu Val Met Pro Gly Ala Ser
1               5                   10                  15

Val Lys Met Ser Cys Lys Ala Ser Gly Tyr Thr Phe Thr Asp His Trp
            20                  25                  30

Met His Trp Val Lys Gln Arg Pro Gly Gln Gly Leu Glu Trp Ile Gly
        35                  40                  45

Thr Ile Asp Leu Ser Asp Thr Tyr Thr Gly Tyr Asn Gln Asn Phe Lys
    50                  55                  60

Gly Arg Ala Thr Leu Thr Leu Asp Glu Ser Ser Asn Thr Ala Tyr Met
65                  70                  75                  80

Gln Leu Ser Ser Leu Thr Ser Glu Asp Ser Ala Val Tyr Tyr Cys Ser
                85                  90                  95

Arg Arg Gly Tyr Tyr Gly Phe Asp Tyr Trp Gly Gln Gly Thr Thr Leu
                100                 105                 110

Thr Val Ser Ser
            115
```

(2) INFORMATION FOR SEQ ID NO:18:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Val Gln Leu Leu Glu Ser Gly Ala Glu Leu Val Lys Pro Gly Ala Ser
1               5                   10                  15

Val Glu Leu Ser Cys Arg Thr Ser Gly Tyr Thr Phe Thr Thr Tyr Tyr
            20                  25                  30

Ile Tyr Trp Val Lys Gln Arg Pro Gly Gln Gly Leu Glu Trp Ile Gly
        35                  40                  45

Gly Met Asn Pro Gly Asn Gly Val Thr Tyr Phe Asn Glu Lys Phe Lys
    50                  55                  60

Asn Arg Ala Thr Leu Thr Val Asp Arg Ser Ser Ser Ile Ala Tyr Met
65                  70                  75                  80

Gln Leu Ser Ser Leu Thr Ser Glu Asp Ser Ala Val Tyr Tyr Cys Thr
                85                  90                  95

Arg Val Gly Asn Leu Phe Ala Tyr Trp Gly Arg Gly Thr Leu Val Thr
                100                 105                 110

Val Ser Ala
        115
```

(2) INFORMATION FOR SEQ ID NO:19:

(i) SEQUENCE CHARACTERISTICS:
        (A) LENGTH: 16 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:19:

Arg Ser Ser Arg Ser Leu Leu Tyr Arg Asp Gly Lys Thr Tyr Leu Asn
1               5                   10                  15

(2) INFORMATION FOR SEQ ID NO:20:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Leu Met Ser Thr Arg Ser Ser
1               5

(2) INFORMATION FOR SEQ ID NO:21:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Gln His Phe Val Asp Tyr Pro Phe Thr
1               5

(2) INFORMATION FOR SEQ ID NO:22:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Arg Ser Ser Lys Ser Leu Leu Tyr Glu Asp Gly Lys Thr Tyr Leu Asn
1               5                   10                  15

(2) INFORMATION FOR SEQ ID NO:23:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Leu Met Ser Thr Arg Ala Ser
1               5

(2) INFORMATION FOR SEQ ID NO:24:

(i) SEQUENCE CHARACTERISTICS:
            (A) LENGTH: 9 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:24:

Gln His Phe Glu Asp Tyr Pro Phe Thr
1               5

(2) INFORMATION FOR SEQ ID NO:25:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Arg Ser Ser Lys Ser Leu Leu Tyr Glu Asp Gly Lys Thr Tyr Leu Asn
1               5                   10                  15

(2) INFORMATION FOR SEQ ID NO:26:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:26:

Leu Met Ser Thr Arg Ala Ser
1               5

(2) INFORMATION FOR SEQ ID NO:27:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:27:

Gln Gln Phe Val Glu Tyr Pro Phe Thr
1               5

(2) INFORMATION FOR SEQ ID NO:28:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

Arg Ser Ser Arg Ser Leu Leu Tyr Arg Asp Gly Lys Thr Tyr Leu Asn
1               5                   10                  15

(2) INFORMATION FOR SEQ ID NO:29:

(i) SEQUENCE CHARACTERISTICS:
            (A) LENGTH: 7 amino acids
            (B) TYPE: amino acid
```

-continued

```
            (C) STRANDEDNESS: single
            (D) TOPOLOGY: linear (ii) MOLECULE TYPE: peptide (xi) SEQUENCE DESCRIPTION: SEQ ID NO:29:

Leu Met Ser Thr Arg Ala Ser
1               5

(2) INFORMATION FOR SEQ ID NO:30:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:30:

Gln His Phe Glu Asp Tyr Pro Phe Thr
1               5

(2) INFORMATION FOR SEQ ID NO:31:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:31:

Arg Ser Ser Thr Gly Thr Ile Thr Thr Ser Asn Tyr Ala Asn
1               5                   10

(2) INFORMATION FOR SEQ ID NO:32:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:32:

Ile Asn Asn Asn Arg Pro Pro
1               5

(2) INFORMATION FOR SEQ ID NO:33:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:33:

Ala Leu Trp Tyr Ser Asn His Trp Val
1               5

(2) INFORMATION FOR SEQ ID NO:34:

(i) SEQUENCE CHARACTERISTICS:
            (A) LENGTH: 14 amino acids
            (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO:34:

Arg Ser Ser Ala Gly Thr Ile Thr Thr Ser Asn Tyr Ala Asn
1               5                   10

(2) INFORMATION FOR SEQ ID NO:35:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Val Asn Asn Asn Arg Pro Pro
1               5

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Ala Leu Trp Tyr Ser Asn His Trp Val
1               5

(2) INFORMATION FOR SEQ ID NO:37:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Arg Ser Ser Thr Gly Thr Ile Thr Ser Asp Asn Tyr Ala Asn
1               5                   10

(2) INFORMATION FOR SEQ ID NO:38:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Val Asn Asn Tyr Arg Pro Pro
1               5

(2) INFORMATION FOR SEQ ID NO:39:

(i) SEQUENCE CHARACTERISTICS:
        (A) LENGTH: 9 amino acids
        (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO:39:

Ala Leu Trp Tyr Ser Asn His Trp Val
1               5

(2) INFORMATION FOR SEQ ID NO:40:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:40:

Arg Ser Ser Ser Gly Thr Ile Thr Ala Asn Asn Tyr Gly Ser
1               5                   10

(2) INFORMATION FOR SEQ ID NO:41:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:41:

Val Ser Asn Asn Arg Gly Pro
1               5

(2) INFORMATION FOR SEQ ID NO:42:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:42:

Ala Leu Trp Asn Ser Asn His Phe Val
1               5

(2) INFORMATION FOR SEQ ID NO:43:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:43:

Lys Ser Ser Gln Ser Leu Leu Tyr Ser Asp Gly Lys Thr Tyr Leu Asn
1               5                   10                  15

(2) INFORMATION FOR SEQ ID NO:44:

(i) SEQUENCE CHARACTERISTICS:
            (A) LENGTH: 7 amino acids
            (B) TYPE: amino acid (C) STRANDEDNESS: single
            (D) TOPOLOGY: linear (ii) MOLECULE TYPE: peptide (xi) SEQUENCE DESCRIPTION: SEQ ID NO:44:

Leu Val Ser Lys Leu Asp Ser
1               5

(2) INFORMATION FOR SEQ ID NO:45:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:45:

Val Gln Gly Tyr Thr Phe Pro Leu Thr
1               5

(2) INFORMATION FOR SEQ ID NO:46:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Ser Asp Tyr Ala Trp Thr
1               5

(2) INFORMATION FOR SEQ ID NO:47:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:47:

Tyr Ile Arg His Ile Tyr Gly Thr Arg Tyr Asn Pro Ser Leu Ile Ser
1               5                   10                  15

(2) INFORMATION FOR SEQ ID NO:48:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:48:

Tyr His Tyr Tyr Gly Ser Ala Tyr
1               5

(2) INFORMATION FOR SEQ ID NO:49:

(i) SEQUENCE CHARACTERISTICS:
            (A) LENGTH: 6 amino acids
            (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:49:

Ser Asp Tyr Ala Trp Thr
1               5

(2) INFORMATION FOR SEQ ID NO:50:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Tyr Ile Arg His Ile Tyr Gly Thr Arg Tyr Asn Pro Ser Leu Ile Ser
1               5                   10                  15

(2) INFORMATION FOR SEQ ID NO:51:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

Tyr His Tyr Tyr Gly Ser Ala Tyr
1               5

(2) INFORMATION FOR SEQ ID NO:52:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

Ser Asp Tyr Ala Trp Asn
1               5

(2) INFORMATION FOR SEQ ID NO:53:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Tyr Ile Arg Tyr Ser Gly Ile Thr Arg Tyr Asn Pro Ser Leu Lys Ser
1               5                   10                  15

(2) INFORMATION FOR SEQ ID NO:54:

(i) SEQUENCE CHARACTERISTICS:
        (A) LENGTH: 8 amino acids
        (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO:54:

Ile His Tyr Tyr Gly Tyr Gly Asn
1               5

(2) INFORMATION FOR SEQ ID NO:55:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:55:

Ser Asp Tyr Ala Trp Thr
1               5

(2) INFORMATION FOR SEQ ID NO:56:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:56:

Tyr Ile Arg His Ile Tyr Gly Thr Arg Tyr Asn Pro Ser Leu Ile Ser
1               5                   10                  15

(2) INFORMATION FOR SEQ ID NO:57:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:57:

Tyr His Tyr Tyr Gly Ser Ala Tyr
1               5

(2) INFORMATION FOR SEQ ID NO:58:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:58:

Asp Tyr Asn Met Tyr
1               5

(2) INFORMATION FOR SEQ ID NO:59:

(i) SEQUENCE CHARACTERISTICS:
            (A) LENGTH: 17 amino acids
            (B) TYPE: amino acid (C) STRANDEDNESS: single
            (D) TOPOLOGY: linear (ii) MOLECULE TYPE: peptide (xi) SEQUENCE DESCRIPTION: SEQ ID NO:59:

Tyr Ile Asp Pro Ser Asn Gly Gly Ile Phe Tyr Asn Gln Lys Phe Lys Gly
1               5                   10                  15

(2) INFORMATION FOR SEQ ID NO:60:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:60:

Gly Gly Gly Leu Phe Ala Tyr
1               5

(2) INFORMATION FOR SEQ ID NO:61:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:61:

Asp Tyr Asn Met Tyr
1               5

(2) INFORMATION FOR SEQ ID NO:62:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:62:

Tyr Ile Asp Pro His Asn Gly Gly Ile Phe Tyr Asn Gln Lys Phe Lys
1               5                   10                  15

Gly (2) INFORMATION FOR SEQ ID NO:63:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:63:

Gly Gly Gly Leu Phe Ala Tyr
1               5

(2) INFORMATION FOR SEQ ID NO:64:

(i) SEQUENCE CHARACTERISTICS:

(A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Asp Tyr Asn Met Tyr
1               5

(2) INFORMATION FOR SEQ ID NO:65:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Tyr Ile Asp Pro Ser Asn Gly Asp Thr Phe Tyr Asn Gln Lys Phe Gln
1               5                   10                  15

Gly (2) INFORMATION FOR SEQ ID NO:66:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Gly Gly Gly Leu Phe Ala Phe
1               5

(2) INFORMATION FOR SEQ ID NO:67:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Thr Tyr Tyr Ile Tyr
1               5

(2) INFORMATION FOR SEQ ID NO:68:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Gly Met Asn Pro Gly Asn Gly Val Thr Tyr Phe Asn Glu Lys Phe Lys
1               5                   10                  15

Asn (2) INFORMATION FOR SEQ ID NO:69:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

```
Val Gly Asn Leu Phe Ala Tyr
1               5
```

(2) INFORMATION FOR SEQ ID NO:70:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

```
Asp His Trp Met His
1               5
```

(2) INFORMATION FOR SEQ ID NO:71:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

```
Thr Ile Asp Leu Ser Asp Thr Tyr Thr Gly Tyr Asn Gln Asn Phe Lys
1               5                   10                  15
Gly
```

(2) INFORMATION FOR SEQ ID NO:72:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

```
Arg Gly Phe Asp Tyr
1               5
```

(2) INFORMATION FOR SEQ ID NO:73:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

```
Arg Ser Ser Xaa Gly Thr Ile Thr Xaa Xaa Asn Tyr Ala Asn
```

```
1               5              10
```

(2) INFORMATION FOR SEQ ID NO:74:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

```
Xaa Asn Asn Tyr Arg Pro Pro
1               5
```

(2) INFORMATION FOR SEQ ID NO:75:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Ala Leu Trp Tyr Ser Asn His Trp Val
1               5
```

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Asp Tyr Asn Met Tyr
1               5
```

(2) INFORMATION FOR SEQ ID NO:77:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Tyr Ile Asp Pro Xaa Asn Gly Xaa Xaa Phe Tyr Asn Gln Lys Phe Xaa
1               5                   10                  15
Gly
```

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Gly Gly Gly Leu Phe Ala Xaa
1               5
```

(2) INFORMATION FOR SEQ ID NO:79:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

```
Arg Ser Ser Xaa Ser Leu Leu Tyr Xaa Asp Gly Lys Thr Tyr Leu Asn
1               5                   10                  15
```

(2) INFORMATION FOR SEQ ID NO:80:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

```
Leu Met Ser Thr Arg Xaa Ser
1               5
```

(2) INFORMATION FOR SEQ ID NO:81:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

```
Gln Xaa Phe Xaa Xaa Tyr Pro Phe Thr
1               5
```

(2) INFORMATION FOR SEQ ID NO:82:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
Ser Asp Tyr Ala Trp Xaa
1               5
```

(2) INFORMATION FOR SEQ ID NO:83:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

Tyr Ile Arg Xaa Xaa Xaa Xaa Thr Arg Tyr Asn Pro Ser Leu Xaa Ser
1               5                   10                  15

(2) INFORMATION FOR SEQ ID NO:84:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:84:

Xaa His Tyr Tyr Gly Xaa Xaa Xaa
1               5

(2) INFORMATION FOR SEQ ID NO:85:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

| | | | | | |
|---|---|---|---|---|---|
| TCTGGACCTG | AGCTGGTGAA | GCCTGGGGCT | TCAGTGAAGG | TATCCTGTAA | GGCTTCTGGT | 60 |
| TATTCATTCA | CTGACTACAA | TATGTACTGG | GTGAAGCAGA | ACCATGGAGA | GAGCCTTGAA | 120 |
| TGGATTGCAT | ATATTGATCC | TTCCAATGGT | GATACTTTCT | ACAACCAGAA | ATTCCAGGGC | 180 |
| AAGGCCACAG | TGACTCTTGA | CAAGTCCTCC | AGTACAGCCT | TCATGCATCT | CAACAGCCTG | 240 |
| ACATCTGAGG | ACTCTGCAGT | CTATTACTGT | GCAAGAGGGG | GGGGCCTGTT | TGCTTTCTGG | 300 |
| GGGCAAGGGA | CTCTGGTCAC | TGTCTCTGCA | | | | 330 |

(2) INFORMATION FOR SEQ ID NO:86:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

| | | | | | |
|---|---|---|---|---|---|
| GATATGGTGA | TGACGCAAGA | CGAACTCTCC | AATCCTGTCA | CTTCTGGAGA | ATCAGTTTCC | 60 |
| ATCTCCTGCA | GGTCTAGTAA | GAGTCTCCTA | TATGAGGATG | GGAAGACATA | CTTGAATTGG | 120 |
| TTTCTGCAGA | GACCAGGACA | ATCTCCTCAC | CTCCTGATCT | ATTTGATGTC | CACCCGTGCA | 180 |
| TCAGGAGTCT | CAGACCGGTT | TAGTGGCAGT | GGGTCAGGAA | CAGATTTCAC | CCTGGAAATC | 240 |
| AGTAGAGTGA | AGGCTGAGGA | TGTGGGTGCG | TATTACTGTC | AACAATTTGT | AGAGTATCCA | 300 |
| TTCACGTTCG | GCTCGGGGAC | AAAGTTGGAA | ATAAGACGGG | TTGATGCCGC | ACCAACTGTA | 360 |
| TCCATCTT | | | | | | 368 |

(2) INFORMATION FOR SEQ ID NO:87:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

```
GATGTGCAGC TTCAGGAGTC GGGACCTGGC CTGGTGAAAC CTTCTCAGTC TCTGTCCCTC      60

ACCTGCACTG TCACTGGCAA TTCAATCACC AGTGATTATG CCTGGACCTG GATCCGGCAG     120

TTTCCAGGAA ACAAACTGGA GTGGATGGGC TACATAAGGC ACATTTATGG CACTAGGTAC     180

AACCCTTCTC TCATAAGTCG AATCTCTATC ACTCGAGACA CGTCCAAGAA CCAGTTCTTC     240

CTGCAGTTGG ATTCTGTGAC TGCTGAGGAC ACAGCCACAT ATTATTGTGT AAGATATCAT     300

TACTACGGTT CGGCTTACTG GGGCCAAGGG ACTCTGGTCA CTGTCTCTGC AGCCAAAACG     360

ACACCC                                                                366
```

(2) INFORMATION FOR SEQ ID NO:88:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:88:

```
GATATTGTGA TGACCCAGGA TGAACTCTCC AATCCTGTCA CTTCTGGAGA ATCAGTTTCC      60

ATCTCCTGCA GGTCTAGTAG GAGTCTCCTA TATAGGGATG GGAAGACATA CTTGAATTGG     120

TTTCTGCAGA GACCAGGACG ATCTCCTCAA CTCCTGATCT ATTTGATGTC CACCCGTTCA     180

TCAGGAGTCT CAGACCGGTT TAGTGGCAGT GGGTCAGGAA CAGATTTCAC CCTGGAAATC     240

AGTAGAGTGA AGGCTGAGGA TGTGGGTGTG TATTACTGTC AACACTTTGT AGACTATCCA     300

TTCACGTTCG GCTCGGGGAC AAAGTTGGAG ATAAAACGG                            339
```

(2) INFORMATION FOR SEQ ID NO:89:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:89:

```
GACGTGCAGT TGCAGGAGTC GGGACCTGGC CTGGTGAAAC CTTCTCAGTC TCTGTCCCTC      60

ACCTGCACTG TCACTGGCAA TTCAATCACC AGTGATTATG CCTGGACCTG GATCCGGCAG     120

TTTCCAGGAA ACAAACTGGA GTGGATGGGC TACATAAGGC ACATTTATGG CACTAGGTAC     180

AACCCTTCTC TCATAAGTCG AATCTCTATC ACTCGAGACA CGTCCAAGAA CCAGTTCTTC     240

CTGCAGTTGG ATTCTGTGAC TGCTGAGGAC ACAGCCACAT ATTATTGTGT AAGATATCAT     300

TACTACGGTT CGGCTTACTG GGGCCAAGGG ACTCTGGTCA CTGTCTCTGC AGCCAAAACG     360

ACACCC                                                                366
```

(2) INFORMATION FOR SEQ ID NO:90:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

| | | | | | |
|---|---|---|---|---|---|
| GATATGGTGA | TGACGCAAGA | TGAACTCTCC | AATCCTGTCA | CTTCTGGAGA | ATCAGTTTCC | 60 |
| ATCTCCTGCA | GGTCTAGTAG | GAGTCTCCTA | TATAGGGATG | GGAAGACATA | CTTGAATTGG | 120 |
| TTTCTGCAGA | GACCAGGACG | ATCTCCTCAA | CTCCTGATCT | ATTTGATGTC | CACCCGTGCA | 180 |
| TCAGGAGTCT | CAGACCGGTT | TAGTGGCAGT | GGGTCAGGAA | CAGATTTCAC | CCTGGAAATC | 240 |
| AGTAGAGTGA | AGGCTGAGGA | TGTGGGTGTG | TATTACTTTC | AACACTTTGA | AGACTATCCA | 300 |
| TTCACGTTCG | GCTCGGGGAC | AAAATTGGAG | ATAAAACGGG | CTGATGCTGC | ACCAACTGTA | 360 |
| TCCATCTT | | | | | | 368 |

(2) INFORMATION FOR SEQ ID NO:91:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

```
Thr Trp Pro Gly Glu Thr Val Thr Leu Thr Cys Arg Ser Ser Thr Gly
1               5                   10                  15

Thr Ile Thr Thr Ser Asn Tyr Ala Asn Trp Val Gln Glu Lys Pro Asp
            20                  25                  30

His Leu Phe Ser Gly Leu Ile Gly Ile Asn Asn Asn Arg Pro Pro Gly
        35                  40                  45

Val Pro Ala Arg Phe Ser Gly Ser Leu Ile Gly Asp Lys Ala Val Leu
    50                  55                  60

Thr Ile Thr Gly Ala Gln Thr Glu Asp Glu Ala Ile Tyr Phe Cys Ala
65                  70                  75                  80

Leu Trp Tyr Ser Asn His Trp Val Phe Gly Gly Thr Lys Leu Thr
                85                  90                  95

Val Leu Gly
```

(2) INFORMATION FOR SEQ ID NO:92:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:92:

```
Thr Arg Pro Gly Glu Thr Val Thr Leu Thr Cys Arg Ser Ser Ala Gly
1               5                   10                  15

Thr Ile Thr Thr Ser Asn Tyr Ala Asn Trp Val Gln Glu Lys Pro Asp
            20                  25                  30

His Leu Phe Ser Gly Leu Ile Gly Val Asn Asn Asn Arg Pro Pro Gly
        35                  40                  45

Val Pro Ala Arg Phe Ser Gly Ser Ile Ile Gly Thr Ala Ala Leu Thr
    50                  55                  60

Ile Thr Gly Ala Gln Thr Glu Asp Glu Ala Ile Tyr Phe Cys Ala Leu
65                  70                  75                  80

Trp Tyr Ser Asn His Trp Val Phe Gly Gly Gly Thr Lys Leu Thr Val
```

85                  90                  95

Leu Gly Asp (2) INFORMATION FOR SEQ ID NO:93:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

Ala Val Val Thr Gln Glu Ser Ala Leu Thr Thr Ser Pro Gly Glu Thr
1               5                   10                  15

Val Thr Leu Thr Cys Arg Ser Ser Thr Gly Thr Ile Thr Ser Asp Asn
                20                  25                  30

Tyr Ala Asn Trp Val Gln Glu Lys Pro Asp His Leu Phe Ser Gly Leu
            35                  40                  45

Ile Gly Val Asn Asn Tyr Arg Pro Pro Gly Val Pro Ala Arg Phe Ser
50                  55                  60

Gly Ser Ile Thr Gly Asp Lys Ala Val Leu Thr Ile Thr Gly Ala Gln
65                  70                  75                  80

Thr Glu Asp Glu Ala Ile Tyr Phe Cys Ala Leu Trp Tyr Ser Asn His
                85                  90                  95

Trp Val Phe Gly Gly Gly Thr Lys Leu Thr Val Leu Gly
            100                 105

(2) INFORMATION FOR SEQ ID NO:94:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

Thr Arg Ala Gly Glu Thr Val Thr Leu Thr Cys Arg Ser Ser Ser Gly
1               5                   10                  15

Thr Ile Thr Ala Asn Asn Tyr Gly Ser Trp Val Gln Glu Lys Pro Asp
                20                  25                  30

His Leu Phe Thr Gly Leu Ile Gly Val Ser Asn Asn Arg Gly Pro Gly
            35                  40                  45

Val Pro Ala Arg Phe Ser Gly Ser Ile Ile Gly Asp Lys Ala Val Leu
50                  55                  60

Thr Ile Thr Gly Gly Gln Thr Glu Asp Glu Ala Ile Tyr Phe Cys Ala
65                  70                  75                  80

Leu Trp Asn Ser Asn His Phe Val Phe Gly Gly Gly Thr Lys Leu Thr
                85                  90                  95

Val Leu Gly (2) INFORMATION FOR SEQ ID NO:95:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:95:

Asp Ile Val Met Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Arg
            20                  25                  30

Asp Gly Lys Thr Tyr Leu Asn Trp Phe Leu Gln Arg Pro Gly Arg Ser
        35                  40                  45

Pro Gln Leu Leu Ile Tyr Leu Met Ser Thr Arg Ser Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln His Phe
                85                  90                  95

Val Asp Tyr Pro Phe Thr Phe Gly Ser Gly Thr Lys Leu Glu Ile Lys
                100                 105                 110

Arg (2) INFORMATION FOR SEQ ID NO:96:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Asp Met Val Met Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Arg
            20                  25                  30

Asp Gly Lys Thr Tyr Leu Asn Trp Phe Leu Gln Arg Pro Gly Arg Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln His Phe
                85                  90                  95

Glu Asp Tyr Pro Phe Thr Phe Gly Ser Gly Thr Lys Leu Glu Ile Lys
                100                 105                 110

Arg (2) INFORMATION FOR SEQ ID NO:97:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Asp Met Val Met Thr Gln Asp Glu Leu Ser Asn Pro Val Thr Ser Gly
1               5                   10                  15

Glu Ser Val Ser Ile Ser Cys Arg Ser Ser Arg Ser Leu Leu Tyr Arg

```
                20                  25                  30
Asp Gly Lys Thr Tyr Leu Asn Trp Phe Leu Gln Arg Pro Gly Arg Ser
            35                  40                  45
Pro Gln Leu Leu Ile Tyr Leu Met Ser Thr Arg Ala Ser Gly Val Ser
        50                  55                  60
Asp Arg Phe Ser Gly Ser Gly Ser Gly Thr Asp Phe Thr Leu Glu Ile
65                  70                  75                  80
Ser Arg Val Lys Ala Glu Asp Val Gly Val Tyr Tyr Cys Gln His Phe
                85                  90                  95
Val Asp Tyr Pro Phe Thr Phe Gly Ser Gly Thr Lys Leu Glu Ile Lys
            100                 105                 110
Arg
```

(2) INFORMATION FOR SEQ ID NO:98:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Asp Ile Val Ile Thr Gln Asp Glu Leu Ser Asn Pro Val Thr Ser Gly
1               5                   10                  15
Glu Ser Val Ser Ile Ser Cys Arg Ser Ser Lys Ser Leu Leu Tyr Glu
                20                  25                  30
Asp Gly Lys Thr Tyr Leu Asn Trp Phe Leu Gln Arg Pro Gly Gln Ser
            35                  40                  45
Pro His Leu Leu Ile Tyr Leu Met Ser Thr Arg Ala Ser Gly Val Ser
        50                  55                  60
Asp Arg Phe Ser Gly Ser Gly Ser Gly Thr Asp Phe Thr Leu Glu Ile
65                  70                  75                  80
Ser Arg Val Lys Ala Glu Asp Val Gly Ala Tyr Tyr Cys Gln Gln Phe
                85                  90                  95
Val Glu Tyr Pro Phe Thr Phe Gly Ser Gly Thr Lys Leu Glu Ile Arg
            100                 105                 110
Arg
```

(2) INFORMATION FOR SEQ ID NO:99:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
Glu Leu Val Met Thr Gln Ser Pro Leu Thr Leu Ser Val Thr Ile Gly
1               5                   10                  15
Gln Pro Ala Ser Ile Ser Cys Lys Ser Ser Gln Ser Leu Leu Tyr Ser
                20                  25                  30
Asp Gly Lys Thr Tyr Leu Asn Trp Phe Phe Gln Arg Pro Gly Gln Ser
            35                  40                  45
Pro Gln Lys Arg Leu Ile Tyr Leu Val Ser Lys Leu Asp Ser Gly Val
        50                  55                  60
```

Pro Asp Arg Phe Thr Gly Ser Gly Ser Gly Lys Asp Phe Thr Leu Lys
65                  70                  75                  80

Ile Ser Arg Val Glu Ala Glu Asp Leu Gly Leu Tyr Tyr Cys Val Gln
                85                  90                  95

Gly Tyr Val Thr Phe Pro Leu Thr Phe Gly Ala Gly Thr Lys Leu Glu
                100                 105                 110

Leu Lys Arg
       115

(2) INFORMATION FOR SEQ ID NO:100:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:100:

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
                20                  25                  30

Tyr Ala Trp Thr Trp Ile Arg Gln Phe Pro Gly Asn Lys Leu Glu Trp
                35                  40                  45

Met Gly Tyr Ile Arg His Ile Tyr Gly Thr Arg Tyr Asn Pro Ser Leu
            50                  55                  60

Ile Ser Arg Ile Ser Ile Thr Arg Asp Thr Ser Lys Asn Gln Phe Phe
65                  70                  75                  80

Leu Gln Leu Asp Ser Val Thr Ala Glu Asp Thr Ala Thr Tyr Tyr Cys
                85                  90                  95

Val Arg Tyr His Tyr Tyr Gly Ser Ala Tyr Trp Gly Gln Gly Thr Leu
                100                 105                 110

Val Thr Val Ser Ala
            115

(2) INFORMATION FOR SEQ ID NO:101:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
                20                  25                  30

Tyr Ala Trp Thr Trp Ile Arg Gln Phe Pro Gly Asn Lys Leu Glu Trp
                35                  40                  45

Met Gly Tyr Ile Arg His Ile Tyr Gly Thr Arg Tyr Asn Pro Ser Leu
            50                  55                  60

Ile Ser Arg Ile Ser Ile Thr Arg Asp Thr Ser Lys Asn Gln Phe Phe
65                  70                  75                  80

Leu Gln Leu Asp Ser Val Thr Ala Glu Asp Thr Ala Thr Tyr Tyr Cys
                85                  90                  95

Val Arg Tyr His Tyr Tyr Gly Ser Ala Tyr Trp Gly Gln Gly Thr Leu
            100                 105                 110

Val Thr Val Ser Ala
            115

(2) INFORMATION FOR SEQ ID NO:102:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
                20                  25                  30

Tyr Ala Trp Thr Trp Ile Arg Lys Phe Pro Gly Asn Lys Leu Glu Trp
            35                  40                  45

Leu Gly Tyr Ile Arg His Ile Tyr Gly Thr Arg Tyr Asn Pro Ser Leu
        50                  55                  60

Ile Ser Arg Ile Ser Ile Thr Arg Asp Thr Ser Lys Asn Gln Phe Phe
65                  70                  75                  80

Leu Gln Leu Asp Ser Val Thr Ala Glu Asp Thr Ala Thr Tyr Tyr Cys
                85                  90                  95

Val Arg Tyr His Tyr Tyr Gly Ser Ala Tyr Trp Gly Gln Gly Thr Leu
            100                 105                 110

Val Thr Val Ser Ala
            115

(2) INFORMATION FOR SEQ ID NO:103:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Glu Leu Val Lys Pro Ser Gln Ser Leu Ser Leu Thr Cys Thr Val Thr
1               5                   10                  15

Gly Tyr Ser Ile Thr Ser Asp Tyr Ala Trp Asn Trp Ile Arg Gln Phe
                20                  25                  30

Pro Gly Asn Arg Leu Glu Trp Met Gly Tyr Ile Arg Tyr Ser Gly Ile
            35                  40                  45

Thr Arg Tyr Asn Pro Ser Leu Lys Ser Arg Ile Ser Ile Thr Arg Asp
        50                  55                  60

Thr Ser Lys Asn Lys Phe Phe Leu Gln Leu Asn Ser Val Thr Thr Glu
65                  70                  75                  80

Asp Thr Ala Thr Tyr Tyr Cys Val Arg Ile His Tyr Tyr Gly Tyr Gly
                85                  90                  95

Asn Trp Gly Gln Gly Thr Thr Leu Thr Gly Leu Pro
            100                 105

(2) INFORMATION FOR SEQ ID NO:104:

(i) SEQUENCE CHARACTERISTICS:
    (A) LENGTH: 110 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:104:

Ser Gly Pro Glu Leu Val Lys Pro Gly Ala Ser Val Lys Leu Ser Cys
1               5                   10                  15

Lys Ala Ser Gly Tyr Pro Phe Thr Asp Tyr Asn Met Tyr Trp Val Lys
                20                  25                  30

Gln Ser His Gly Lys Ser Leu Glu Trp Ile Gly Tyr Ile Asp Pro Ser
            35                  40                  45

Asn Gly Gly Ile Phe Tyr Asn Gln Lys Phe Lys Gly Arg Ala Thr Leu
50                  55                  60

Thr Val Asp Lys Ser Ser Asn Thr Ala Phe Met His Leu Asn Ser Leu
65                  70                  75                  80

Thr Ser Glu Asp Ser Ala Val Tyr Tyr Cys Ala Arg Gly Gly Gly Leu
                85                  90                  95

Phe Ala Tyr Trp Gly Gln Gly Thr Leu Val Thr Val Ser Glu
                100                 105                 110

(2) INFORMATION FOR SEQ ID NO:105:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:105:

Glu Ile His Leu Gln Gln Ser Gly Pro Glu Leu Val Lys Pro Gly Ala
1               5                   10                  15

Ser Val Lys Leu Ser Cys Lys Ala Ser Gly Tyr Ser Phe Thr Asp Tyr
                20                  25                  30

Asn Met Tyr Trp Val Lys Gln Ser His Gly Lys Ser Leu Glu Trp Ile
            35                  40                  45

Gly Tyr Ile Asp Pro His Asn Gly Gly Ile Phe Tyr Asn Gln Lys Phe
50                  55                  60

Lys Gly Arg Ala Thr Leu Thr Val Asp Lys Ser Ser Asn Thr Ala Phe
65                  70                  75                  80

Met His Leu Asn Ser Leu Thr Ser Glu Asp Ser Ala Val Tyr Tyr Cys
                85                  90                  95

Ala Arg Gly Gly Gly Leu Phe Ala Tyr Trp Gly Arg Gly Thr Leu Val
                100                 105                 110

Thr Val Ser Ala
            115

(2) INFORMATION FOR SEQ ID NO:106:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:106:

Glu Val Gln Leu Gln Glu Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Asn His Gly Glu Ser Leu Glu Trp Ile
        35                  40                  45

Ala Tyr Ile Asp Pro Ser Asn Gly Asp Thr Phe Tyr Asn Gln Lys Phe
50                  55                  60

Gln Gly Lys Ala Thr Val Thr Leu Asp Lys Ser Ser Ser Thr Ala Phe
65                  70                  75                  80

Met His Leu Asn Ser Leu Thr Ser Glu Asp Ser Ala Val Tyr Tyr Cys
            85                  90                  95

Ala Arg Gly Gly Gly Leu Phe Ala Phe Trp Gly Gln Gly Thr Leu Val
            100                 105                 110

Thr Val Ser Ala
            115

(2) INFORMATION FOR SEQ ID NO:107:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Val Gln Leu Leu Glu Ser Gly Ala Glu Leu Val Met Pro Gly Ala Ser
1               5                   10                  15

Val Lys Met Ser Cys Lys Ala Ser Gly Tyr Thr Phe Thr Asp His Trp
            20                  25                  30

Met Trp Val Lys Gln Arg Pro Gly Gln Gly Leu Glu Trp Ile Gly Thr
        35                  40                  45

Ile Asp Leu Ser Asp Thr Tyr Thr Gly Tyr Asn Gln Asn Phe Lys Gly
50                  55                  60

Arg Ala Thr Leu Thr Leu Asp Glu Ser Ser Asn Thr Ala Tyr Met Gln
65                  70                  75                  80

Leu Ser Ser Leu Thr Ser Glu Asp Ser Ala Val Tyr Tyr Cys Ser Arg
            85                  90                  95

Arg Gly Phe Asp Tyr Trp Gly Gln Gly Thr Thr Leu Thr Val Ser Ser
            100                 105                 110

(2) INFORMATION FOR SEQ ID NO:108:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:108:

Val Gln Leu Leu Glu Ser Gly Ala Glu Leu Val Lys Pro Gly Ala Ser
1               5                   10                  15

Val Glu Leu Ser Cys Arg Thr Ser Gly Tyr Thr Phe Thr Thr Tyr Tyr
            20                  25                  30

Ile Tyr Trp Val Lys Gln Arg Pro Gly Gln Gly Leu Glu Trp Ile Gly
        35                  40                  45

```
Gly Met Asn Pro Gly Asn Gly Val Thr Tyr Phe Asn Glu Lys Phe Lys
    50                  55                  60

Asn Arg Ala Thr Leu Thr Val Asp Arg Ser Ser Ser Ile Ala Tyr Met
65              70                  75                  80

Gln Leu Ser Ser Leu Thr Ser Glu Asp Ser Ala Val Tyr Tyr Cys Thr
                85                  90                  95

Arg Val Gly Asn Leu Phe Ala Tyr Trp Gly Arg Gly Thr Leu Val Thr
            100                 105                 110

Val Ser Ala
        115
```